US012751828B2

(12) United States Patent
Clarke et al.

(10) Patent No.: US 12,751,828 B2
(45) Date of Patent: Oct. 6, 2026

(54) HIP IMPLANT ASSEMBLY, SYSTEM AND METHOD OF USE

(71) Applicant: Michael Clarke, Manlius, NY (US)

(72) Inventors: Michael Clarke, Manlius, NY (US); Alexander Clarke, Manlius, NY (US)

(73) Assignee: CERAMOX LLC, Manlius, NY (US)

( * ) Notice: Subject to any disclaimer, the term of this patent is extended or adjusted under 35 U.S.C. 154(b) by 911 days.

(21) Appl. No.: 17/968,426

(22) Filed: Oct. 18, 2022

(65) Prior Publication Data

US 2024/0122716 A1 Apr. 18, 2024

(51) Int. Cl.
*A61F 2/34* (2006.01)
*A61F 2/30* (2006.01)

(52) U.S. Cl.
CPC ....... *A61F 2/34* (2013.01); *A61F 2002/30113* (2013.01); *A61F 2002/3092* (2013.01); *A61F 2002/3093* (2013.01)

(58) Field of Classification Search
CPC ........................................................ A61F 2/34
See application file for complete search history.

(56) References Cited

U.S. PATENT DOCUMENTS 4,566,138 A 1/1986 Lewis et al.
4,936,856 A 6/1990 Keller
5,226,917 A 7/1993 Schryver
5,360,452 A 11/1994 Engelhardt et al.
5,571,198 A 11/1996 Drucker et al.
5,702,475 A 12/1997 Zahedi
5,755,806 A 5/1998 Stalcup et al.
5,925,077 A 7/1999 Wiliamson et al.
6,045,583 A 4/2000 Gross et al.
6,537,321 B1 3/2003 Horber
6,572,655 B1 6/2003 Johnson
(Continued)

FOREIGN PATENT DOCUMENTS

EP 0687452 A1 12/1995
FR 2638963 A1 5/1990
WO 2011107829 A1 9/2011

OTHER PUBLICATIONS

Ries, M.D. et al.; Reflection InterFit, Porous-Coated Acetabular Component; Acetabular Bone Strains Produced by Oversized Press-Fit Cup; Scientific Exhibition Presented at the 63rd Annual Meeting of the AAOS, 1996.

(Continued)

*Primary Examiner* — Brian A Dukert
(74) *Attorney, Agent, or Firm* — Barclay Damon LLP

(57) ABSTRACT

A medical implant assembly includes a body and at least one support removably coupled to the body. The body has an outer surface, a cavity defined by an inner surface, a rim surrounding a cavity opening with a plurality of bores extending from the rim to the outer surface and one or more openings extending between the inner surface and the outer surface. The at least one support includes a first end structured to frictionally fit within one of the plurality of bores and an opposing second end positioned away from the body and structured to be secured to a host bone tissue. At least one of: (i) the at least one support; and (ii) the body, are structured to allow or promote at least one of: (i) bone ingrowth; and (ii) bone ongrowth.

41 Claims, 58 Drawing Sheets

(56) References Cited

U.S. PATENT DOCUMENTS

| | | | | |
|---|---|---|---|---|
| 8,211,184 | B2 | 7/2012 | Ries | |
| 9,192,478 | B2 * | 11/2015 | Weeden | A61F 2/34 |
| 9,427,321 | B2 | 8/2016 | Termanini | |
| 10,456,262 | B2 * | 10/2019 | Mistry | A61F 2/34 |
| 10,595,911 | B1 | 3/2020 | Horton et al. | |
| 2002/0147499 | A1 | 10/2002 | Shea et al. | |
| 2005/0288793 | A1 | 12/2005 | Dong | |
| 2007/0142921 | A1 | 6/2007 | Lewis et al. | |
| 2007/0162147 | A1 | 7/2007 | Lewis et al. | |
| 2008/0172130 | A1 * | 7/2008 | Macara | A61F 2/34 623/22.36 |
| 2010/0256771 | A1 | 10/2010 | Roberts et al. | |
| 2012/0101590 | A1 | 4/2012 | Preuss | |
| 2018/0193156 | A1 | 7/2018 | Zajac | |
| 2020/0155212 | A1 | 5/2020 | Hopkins | |

OTHER PUBLICATIONS

International Searching Authority; International Search Report and Written Opinion; International Application No. PCT/US23/35383; Date of Mailing: Apr. 8, 2024; 11 pages.

International Preliminary Examining Authority; International Preliminary Report on Patentability; International Application No. PCT/US2023/035383; Date of Mailing: Feb. 27, 2025; 43 pages.

* cited by examiner

FIG. 27B
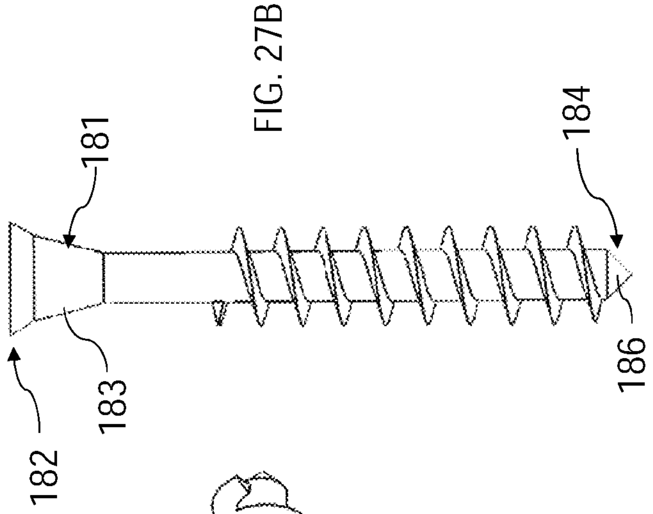
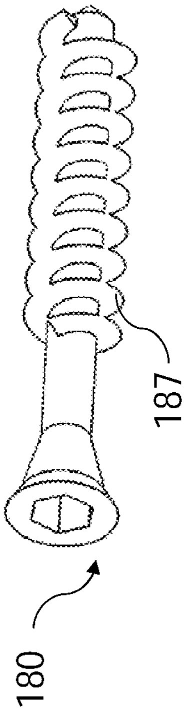
FIG. 27A
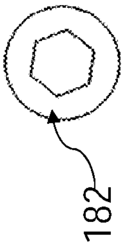
FIG. 27C

HIP IMPLANT ASSEMBLY, SYSTEM AND METHOD OF USE

FIELD OF TECHNOLOGY

The present invention generally relates to the field of medical prosthetics and more specifically, to a hip implant system to be primarily used in revision hip replacement surgery. The hip implant system includes a positioning (or templating) device and a medical implant assembly having a body with a plurality of removably coupled supports. The system is easily customizable for each patient and provides improved fixation to host bone tissue but, without necessarily requiring substantial direct fixation of the body of the medical implant to the host bone tissue.

BACKGROUND

Hip replacement surgery is a common and accepted form of treatment around the world for many conditions that affect the hip joint. This process generally involves the implantation of a prosthetic device or implant, such as a prosthetic hip or hip implant, typically comprised of metal alloys, ceramics and/or plastics that take the place of either a portion of the native hip joint or alternatively, the entire hip joint. Unfortunately, these prosthetic devices can fail over time requiring a subsequent replacement surgery commonly known as a "revision" surgery or procedure.

Many revision procedures often require the use of specialized implants that are not normally used in primary or non-revision procedures. One difficulty in revision hip surgery on the acetabular (pelvic) side is obtaining fixation to the bone after the bone has been compromised by either osteolysis (bone loss) and/or necrosis (bone death). The overall success of the prosthetic device typically requires the stable placement of the prosthetic device relative to the host bone tissue. Long-term stability and success is achieved by stable fixation which allows for bone growth into and/or onto the implant depending on the surface characteristics of that implant. Fixation is promoted by maximizing the area of contact between the implant and the host bone tissue.

Unfortunately, failure of prosthetic devices such as those implanted in the hip is frequently accompanied by loss of bone at and/or around the area around the implant by osteolysis and/or osteonecrosis. The prosthetic devices and implants that are re-implanted during a revision procedure frequently suffer from a lack of stability relative to the host bone, which leads to insufficient bone growth into or onto the revision implant due to micro- or macro-motion. Other prosthetic devices currently used in revision procedures are typically designed to maximize the approximation of the central body or bodies of the implant to the residual host bone in order to enable bone ongrowth or ingrowth. Other implanted devices include projections or spacers configured to provide a space between the host bone tissue and the implant that can be occupied by acrylic bone cement which creates a mechanical interlock and is not reliant on bone ingrowth or ongrowth. Some prosthetic devices include projections that are integrally formed as part of the prosthetic device itself or the implant. These features limit the ability of a single prosthetic device or implant to be customized for each patient and are designed such that there is significant potential for fretting at the contact surface.

Still other prosthetic devices and implants used in revision procedures include implants that are meant to be in direct contact with the host bone tissue and are coupled using a plurality of extensions, supports or anchors that project at various angles from the prosthetic device or implant. Such devices also suffer from stability issues as they are not suited for compressive loads, especially where bone loss is present. Consequently, the lifespan of prosthetic devices used for revision procedures is diminished. In other more extreme cases, a custom prosthetic device and/or implant must be made. These latter devices, which are typically based on a computer generated three dimensional CT scan model, can take weeks or even months to complete and at a very large cost.

The foregoing are just some of the problems related to current prosthetic devices and implants used in hip revision surgery. Correspondingly, there is a need to develop a system and/or device suitable for revision or replacement surgical procedures that is configurable to a patient, that can be stably placed, and has minimal long-term complications.

BRIEF DESCRIPTION

In accordance with one aspect, a hip implant assembly includes a hip implant assembly that comprises a body configured for fixation to the pelvis of a patient. The body has a suitable shape, such as hemi-spherical, elliptical, bilobed, toroidal, or sub-hemispheric and has a plurality of openings, cavities and/or bores traversing the body. A plurality of supports are attached via the plurality of openings and/or bores that enhance the surface area for bone ingrowth and/or bone ongrowth in addition to enhancing the stability of the hip implant assembly relative to the host bone. The plurality of supports are attached to the body in a way that minimizes micromotion, fretting and thus fretting corrosion. The body further is structured to accept an insert of a prosthetic hip that engages the femoral component (a part sphere or similar is usual) of the prosthetic hip. The body may include a concave or other surface that is suitably shaped to engage the insert of a prosthetic hip that engages the femoral component. The insert is usually formed from a metal alloy, ceramic, plastic or combination(s) thereof and employs a mechanism that allows mechanical fixation to the concavity or other suitably shaped internal surface of the body.

According to another aspect, the hip implant assembly includes a body and one or more supports removably coupled to the body. The body includes an outer surface, a cavity having an inner surface and a plurality of inner openings extending between the inner surface and the outer surface. The body further includes a rim defining an opening of the cavity and a plurality of bores extending between the rim and the outer surface. The one or more supports each include a first end having a tapered surface that is structured to enable a friction fit within one of the plurality of bores, and an opposing second end positioned away from the body and structured to be secured to a host bone tissue. The one or more supports are structured to at least partially hold the body away from the host bone tissue. The one or more supports and the body are also structured for at least one of: (i) bone ingrowth; and (ii) bone ongrowth.

According to at least one embodiment, at least one of the plurality of bores includes a first diameter and a second diameter that is different from the first diameter. The one or more supports can have a circular cross-section. In an embodiment, the second end of the one or more supports comprises a frustoconical tapered surface. In an embodiment, the first end of the one or more support is structured to receive a fastener. In a further embodiment of the hip implant assembly, the cavity is structured to receive an insert of a prosthetic hip. In an embodiment, the second end of the one or more supports includes a threaded surface. In another embodiment, the hip implant assembly further includes at least one securing member that has a first end structured to be removably coupled to the body and a second end. The second end of the at least one securing member defines one or more openings dimensioned to accept one or more fasteners to couple the at least one securing member to the host bone tissue such that the host bone tissue is positioned away from the body. In another embodiment, the one or more supports includes a shoulder. In still another embodiment, at least one of the inner openings includes a tapered surface structured to enable a friction-fit with the one or more body supports. In a further embodiment, the one or more supports of the hip implant assembly has a non-polygonal cross-section.

According to another aspect, a medical implant assembly includes a body and at least one support removably coupled to the body. The body includes an outer surface, a cavity defined by an inner surface, a rim surrounding a cavity opening and having a plurality of bores extending from the rim to the outer surface. The body further includes one or more openings extending between the inner surface and the outer surface. The at least one support includes a first end structured to frictionally fit within one of the plurality of bores and an opposing second end positioned away from the body and structured to be secured to a host bone tissue. At least one of the at least one support or the body are structured to promote and/or allow bone ingrowth and/or bone ongrowth.

According to at least one embodiment of the medical implant assembly, the cavity is eccentrically positioned in relation to the rim. In a further embodiment, the at least one support has a circular cross-section. In an embodiment, the opposing second end of the at least one support includes a frustoconical tapered surface. In another embodiment of the medical implant assembly, the at least one support is structured to at least partially hold the body away from the host bone tissue. In an embodiment, the first end of the at least one support is structured to receive a fastener to couple the at least one support to the body. In another embodiment, the cavity is structured to receive an insert of a prosthetic hip. In an embodiment, the opposing second end of the at least one support includes a threaded surface. In an embodiment, the medical implant assembly further includes at least one securing member having a first end configured to be removably coupled to the body and a second end defining one or more openings dimensioned to accept at least one fastener to couple the at least one securing member to the host bone tissue such that the host bone tissue is positioned away from the body. In an embodiment, the first end of the at least one securing member is inwardly reflexed in relation to the opposing second end of the securing member. In a further embodiment of the medical implant assembly, the at least one support includes a shoulder. In an embodiment, the body further defines a plurality of channels extending from the rim to the outer surface.

According to at least one other embodiment of the medical implant assembly, the at least one support includes a first tapered portion and a second tapered portion such that the first tapered portion has an increasing diameter from the first end of the at least one support to a circumferential apex. The second tapered portion of the at least one support includes a decreasing diameter from the circumferential apex to the opposing second end of the at least one support. In another embodiment, at least some of the plurality of bores and the plurality of channels extend along parallel axes. In still another embodiment, at least some of the one or more openings extending between the inner surface and the outer surface extend along intersecting axes. In yet a further embodiment, the first end of the at least one support includes a non-polygonal cross-section, such as a discorectangle.

According to another aspect, a method of manufacturing a hip implant assembly includes structuring a body to include an outer surface, a rim defining an opening to a formed cavity, a plurality of bores extending from the rim to the outer surface, an inner surface defining the formed cavity and one or more inner openings extending between the inner surface and the outer surface. One or more supports are structured to removable couple to the body. The one or more supports are further structured to include a first end that frictionally fits within one of the plurality of bores, a second end positioned away from the body and secures to a host bone tissue and a portion structured to allow and/or promote bone ingrowth and/or bone ongrowth. In another embodiment, the one or more supports may further include a biochemical coating that enhances natural bone formation.

According to a further aspect, a medical implant system includes a templating device and a medical implant assembly. The templating device includes a body structured to be positioned in a surgical site and to guide a medical instrument for preparing the surgical site. The medical implant assembly includes a body and at least one support removably coupled to the body. The body of the medical implant assembly includes an outer surface, a cavity defined by an inner surface and a rim surrounding a cavity opening and having a plurality of bores extending from the rim to the outer surface. The body further includes one or more openings extending between the inner surface and the outer surface. The at least one support includes a first end structured to frictionally fit within one of the plurality of bores and an opposing second end positioned away from the body and structured to be secured to a host bone tissue within the surgical site. At least the at least one support and/or the body of the medical implant assembly are configured for bone ingrowth and/or bone ongrowth.

An advantage provided by the herein described implant system is the ability to be stably implanted in the body without any or substantially any direct contact to host bone tissue of the body. Another advantage is that the implant system is configured for bone ingrowth and/or ongrowth at the supports as well as the body, thus increasing the surface area for fixation in order to provide a more stable fixation with an increased rate of long-term success. Another advantage is that the body can be configured to receive a larger insert, which increases the stability of the prosthetic hip implant reducing the risk of disengagement of the ball from the socket (dislocation). A further advantage is that the implant system is able to be customized to each patient in a fast and cost-efficient manner.

These and other features and advantages will be readily apparent from the following Detailed Description, which should be read in conjunction with the accompanying drawings.

BRIEF DESCRIPTION OF THE DRAWINGS

A more particular description of the briefly summarized above may be had by reference to the embodiments, some of which are illustrated in the accompanying drawings. It is to be noted, however, that the appended drawings illustrate only typical embodiments of this invention and are therefore not to be considered limiting of its scope, for the invention may admit to other equally effective embodiments. Thus, for further understanding of the nature of the objects of the invention, references can be made to the following detailed description, read in connection with the drawings in which:

FIG. 27A illustrates a perspective side view of an embodiment of a compression bone screw;

FIG. 27B illustrates a side view of the compression bone screw of FIG. 27A;

FIG. 27C illustrates a top view of the compression bone screw of FIGS. 27A and 27B;

DETAILED DESCRIPTION

The following description relates to various embodiments of an improved medical implant system and more specifically a hip implant system used in hip revision surgery. It will be readily apparent that these embodiments are merely examples and that numerous variations and modifications are possible that embody the inventive aspects discussed herein. Although the foregoing description is limited to applications of hip replacement and revision surgeries, the inventive concepts described herein are also applicable to other types of joint replacement surgery and prosthetic implant procedures. In addition, several terms are used throughout this description to describe salient features of the invention in conjunction with the accompanying figures. These terms, which may include, “first”, “second”, “inner”, “outer”, “upper”, “lower”, and the like are not intended to overly limit the scope of the invention, unless so specifically indicated. The terms “about” or “approximately” as used herein may refer to a range of 80%-125% of the claimed or disclosed value. With regard to the drawings, their purpose is to depict salient features of the medical implant system and are not specifically provided to scale.

Figure 3:
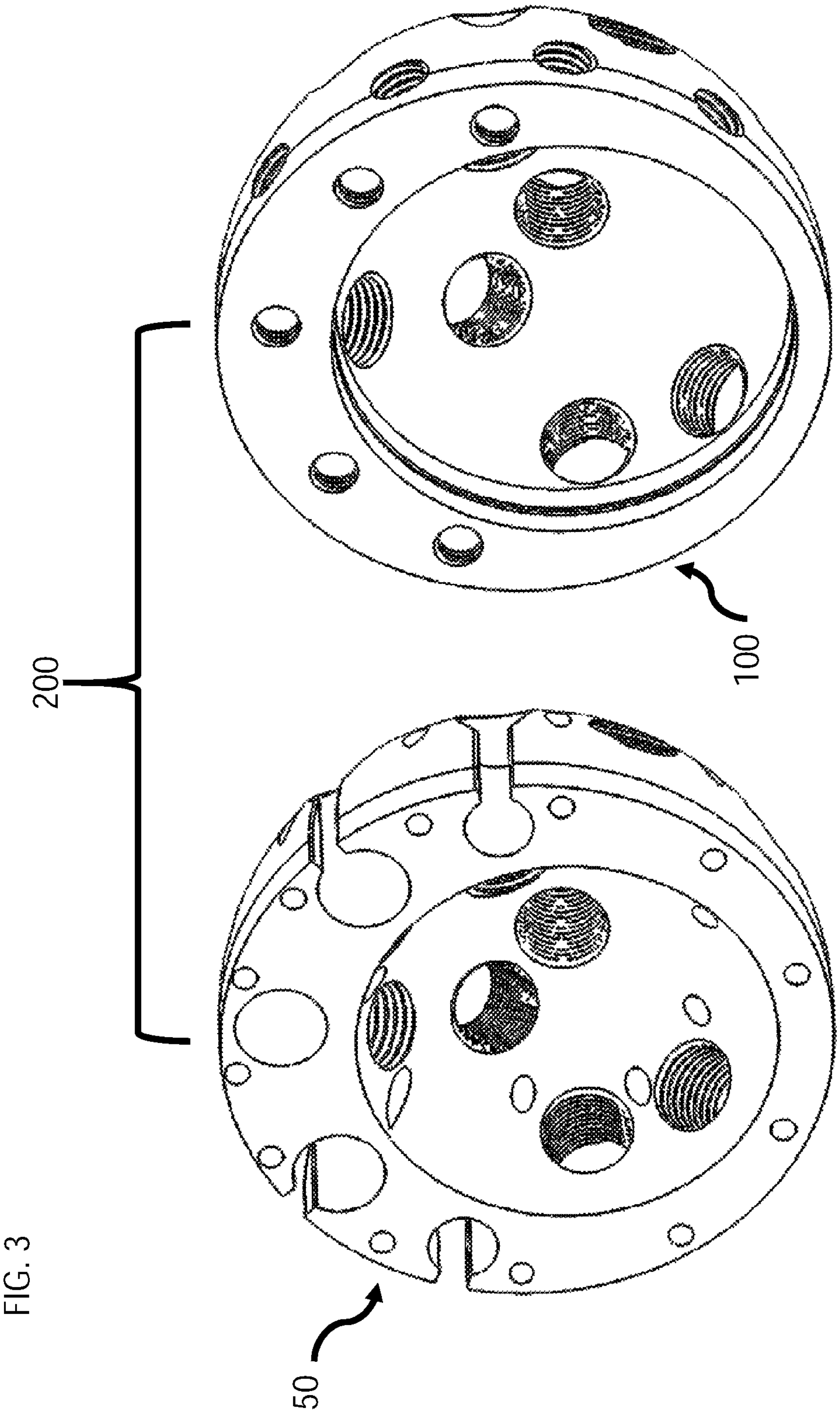
FIG. 3 illustrates a perspective view of a medical implant system including a positioning (templating) device and the body of an unassembled medical implant.

Disclosed herein and shown specifically in FIG. 3, is a medical implant system or implant system 100 comprised of metal or metal alloy (such as titanium, titanium alloy, cobalt chromium or stainless steel) and a medical positioning device or positioning device 50 which can be comprised of metal, plastic or other suitable implant or non-implant material. Together, the devices comprise a medical implant system or implant system 200. In general, the disclosed implant system 200 includes a positioning or templating device 50 and a medical implant assembly 100. In the embodiments described, the medical implant system 200 is a hip implant system that interacts with the femoral component 9 (FIG. 1) of a prosthetic hip 1 (FIG. 1), however other embodiments may be used in conjunction with other types of prosthetic devices that are implanted in a mammalian body. Several components of the medical implant assembly 100 have surface features, bores or a coating that allows and/or promotes bone ingrowth and/or ongrowth, which improves the long term stability and success of the medical implant assembly 100.

Figure 1:
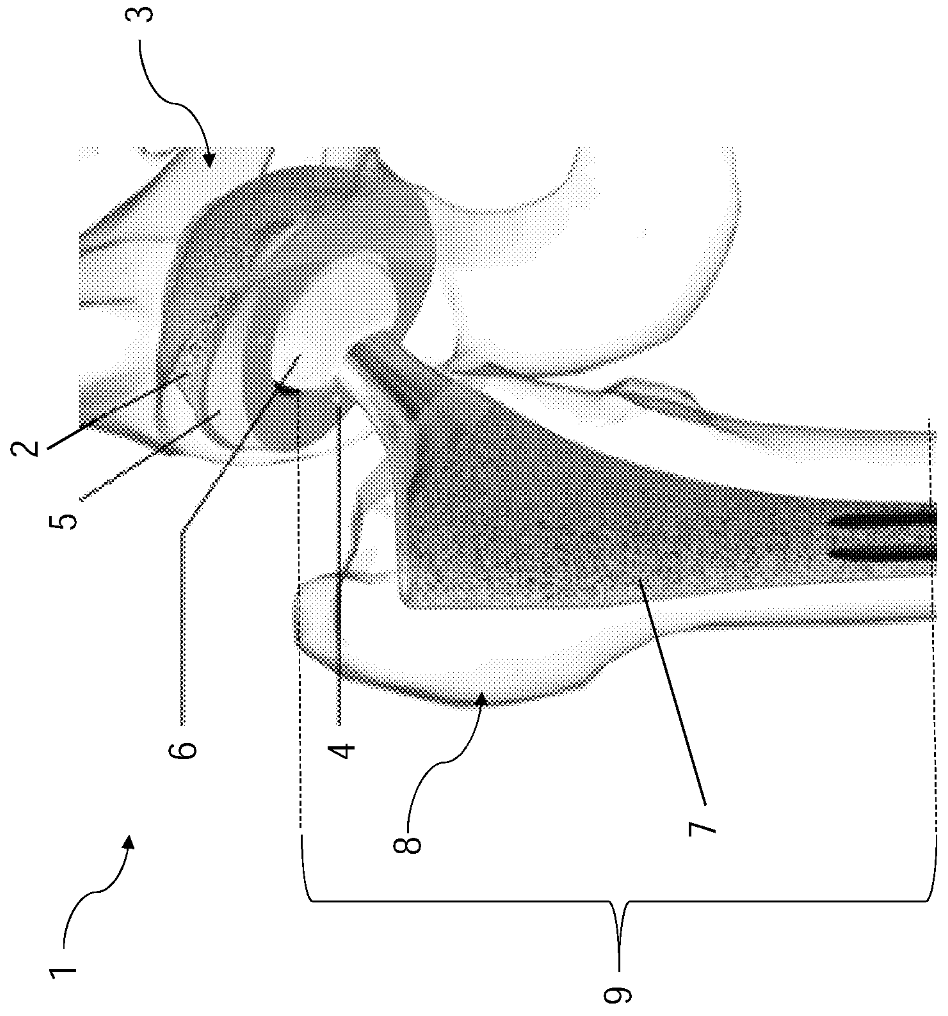
FIG. 1 illustrates a section view of an embodiment of a prosthetic hip implanted in bone tissue, where the bone tissue is shown as being transparent.

Referring to FIG. 1, a typical prosthetic hip 1 generally comprises a shell 2 that is fixed or otherwise secured directly to host bone tissue 3 often using fasteners such as screws (not shown). A bearing liner or insert 4 having a typically convex surface 5 is positioned and secured within the shell 2. A femoral component 9, which includes a typically spherical head or ball 6 that is positioned within the insert 4 and connected to a stem 7, extends into and is secured to the femur bone 8 of an individual's leg. The head 6 is capable of pivoting relative to the insert 4 as the individual moves their leg. Over time the insert 4 can wear away, which leads to an overall need to replace the prosthetic hip 1. It is desired to use an insert 4 as large as possible in order to help increase the stability of the prosthetic hip 1 from dislocation where the spherical head 6 can disengage from the bearing liner 4, resulting in a dislocation that requires urgent surgical reduction. As can be seen, most of the shell 2 is in direct contact with the host bone tissue 3, which enables stable fixation by the surgeon and improved long term stability as bone ongrowth or ingrowth occurs on the shell 2 over time.

Figure 2:
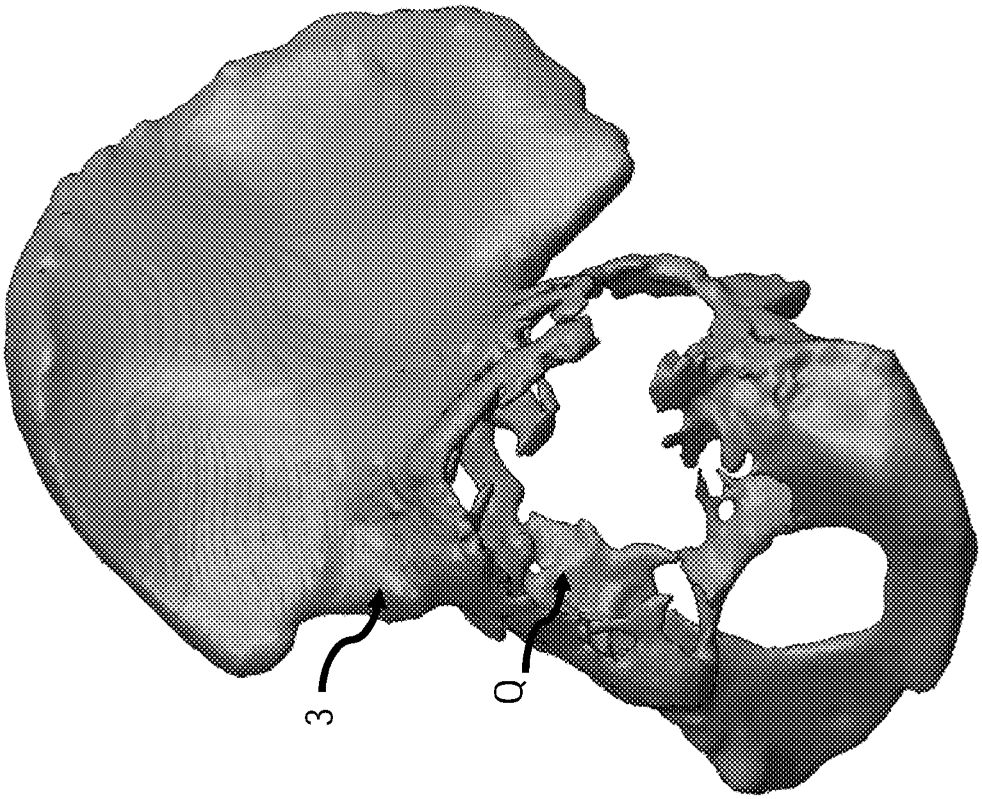
FIG. 2 illustrates a perspective front view of an embodiment of host bone tissue that exhibits significant bone loss in and around a surgical site.

However, in many cases the host bone tissue 3 may be too damaged due to osteolysis or necrosis (bone loss or bone death) to use the prosthetic hip 1 shown in FIG. 1. An example of damaged host bone tissue 3 is shown in FIG. 2. Here, the host bone tissue 3, in this case hip bone tissue, has experienced severe damage or degradation, especially in area Q, where the shell 2 of the prosthetic hip 1 from FIG. 1 would be placed. As shown, there is little to no host bone tissue 3 (see FIGS. 1, 2, 39-41, 43A and 43B) in area Q or a surgical site. This absence of host bone tissue will make it difficult for the surgeon to create a stable fixation of the prosthetic hip 1, which will be detrimental to the long term stability and overall success of the medical implant.

Figure 4:
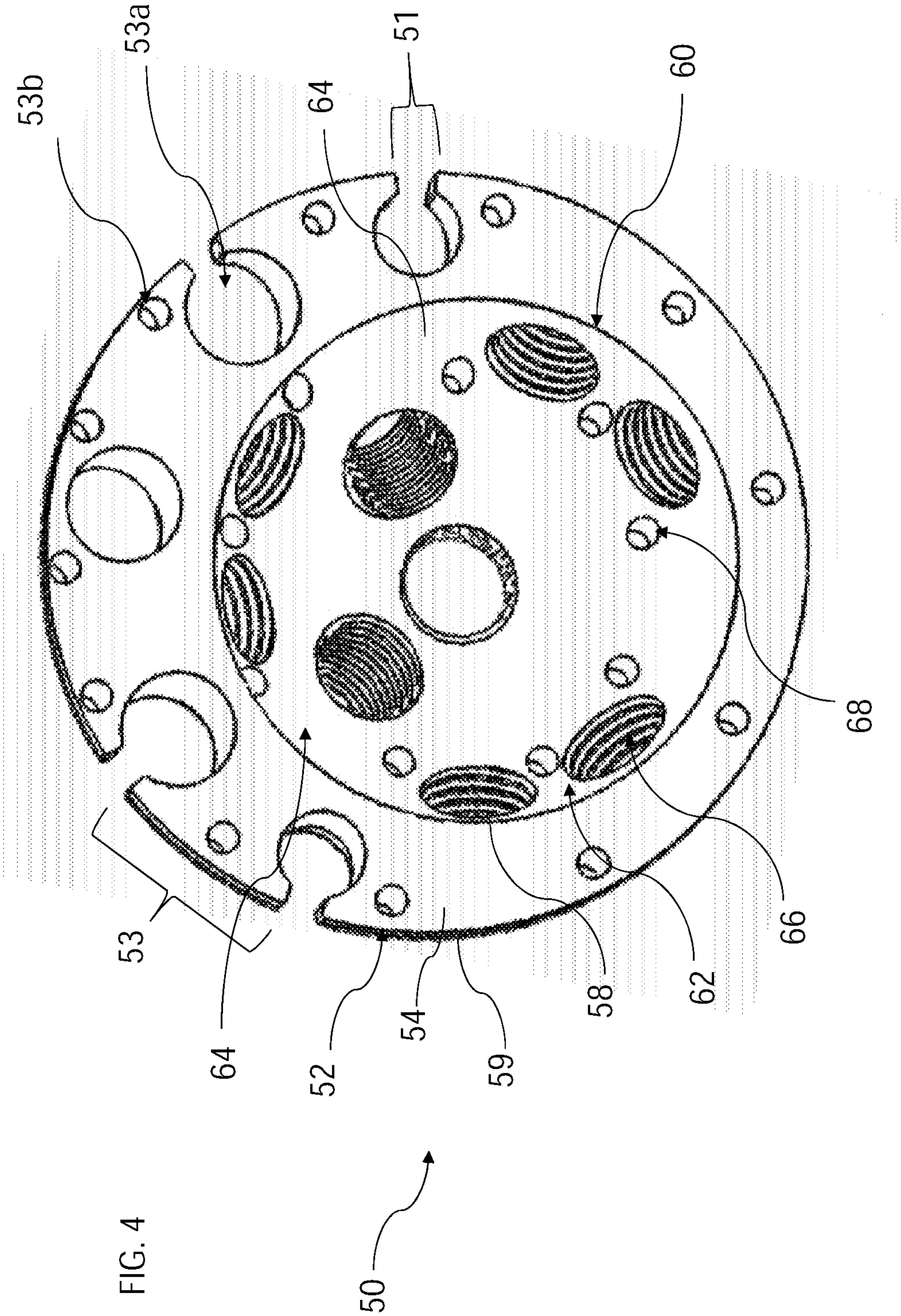
FIG. 4 illustrates a top view of an embodiment of a positioning (templating) device of the medical implant system.
Figure 5:
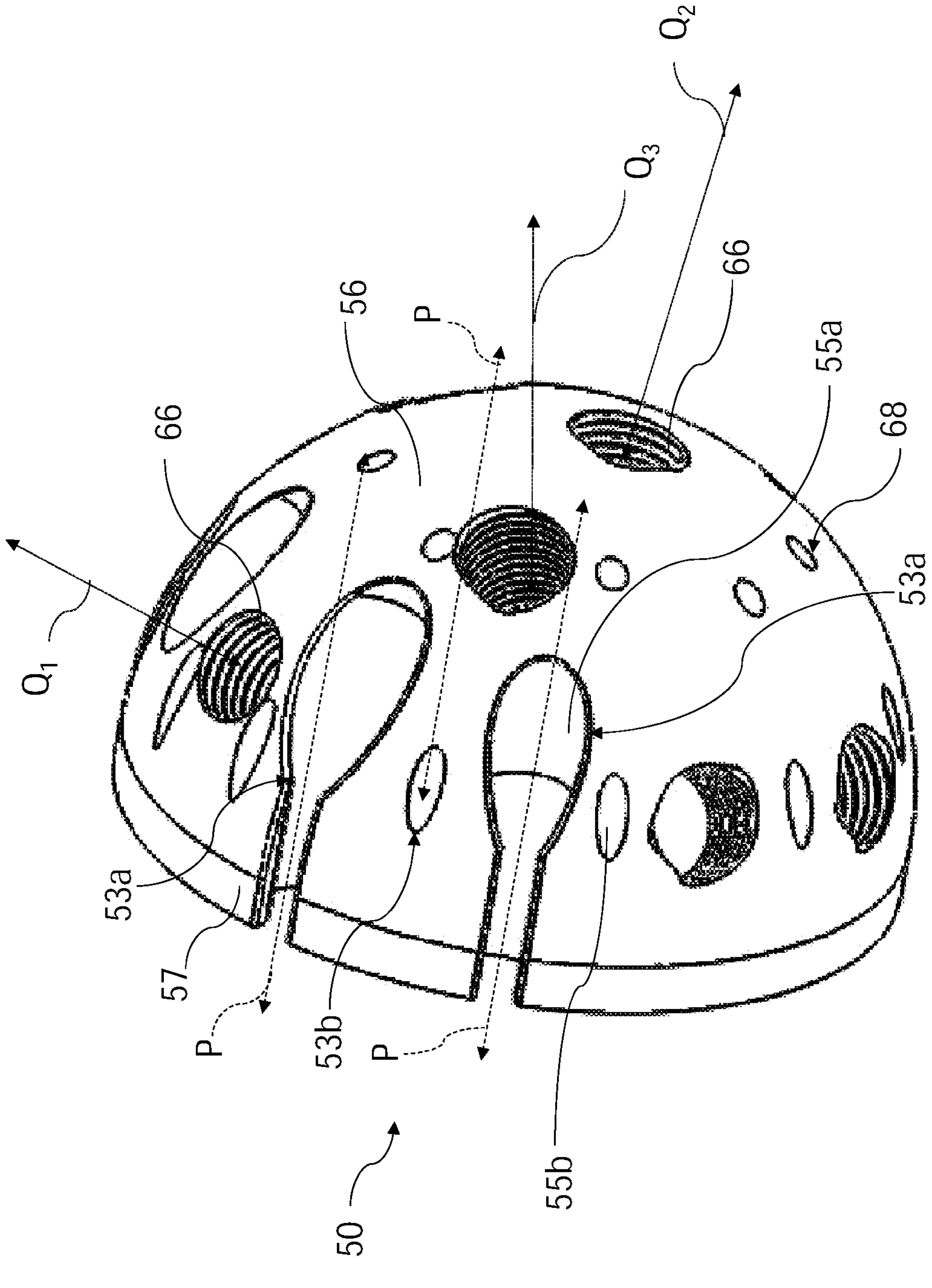
FIG. 5 illustrates a side view of the embodiment of the positioning device of FIGS. 3 and 4.

Turning now to FIGS. 3-6B, an embodiment of a positioning or templating device 50 of the medical implant system 200 is shown. The positioning device 50 has a generally hemispherical structure 52 with a rim surface 54 or rim that is generally planar in addition to an outer convex surface 56. The rim surface 54 defines an outer edge 59 that is substantially circular or elliptical in shape, and an inner edge 58 that is substantially circular in shape. A plurality of channels 53*a*, and bores 53*b* are defined on the positioning device 50, each being formed in the rim surface 54 and in which each channel 53*a* and bore 53*b* are at least partially surrounded by an inner surface 55*a*, 55*b*, respectively, that terminate at the outer convex surface 56. As shown, the inner surface 55*a* of each of the plurality of channels 53*a* does not completely surround the channels 53*a* resulting in a gap section 51. As a result, at least a portion of the outer edge 59 appears to be broken or discontinuous wherein the outer edge 59 is comprised of a plurality of arcs 53 circumferentially separated by a portion of the inner surface 55*a* of the channels 53*a*. In other embodiments there is no gap section 51 present in any of the channels 53*a* and the outer edge 59 is continuous. The plurality of channels 53*a* and some of the plurality of bores 53*b* extend entirely through the rim surface 54 to the outer convex surface 56 along parallel axes P, as shown in FIG. 5. In an embodiment, a peripheral transition surface 57 is defined between the outer edge 59 of the rim surface 54 and the outer convex surface 56. In some embodiments, the transition surface 57 may alternatively define one or more surface features and/or may extend radially from the outer convex surface 56 to aid in positioning the positioning device 50 within the surgical site.

Figure 6A:
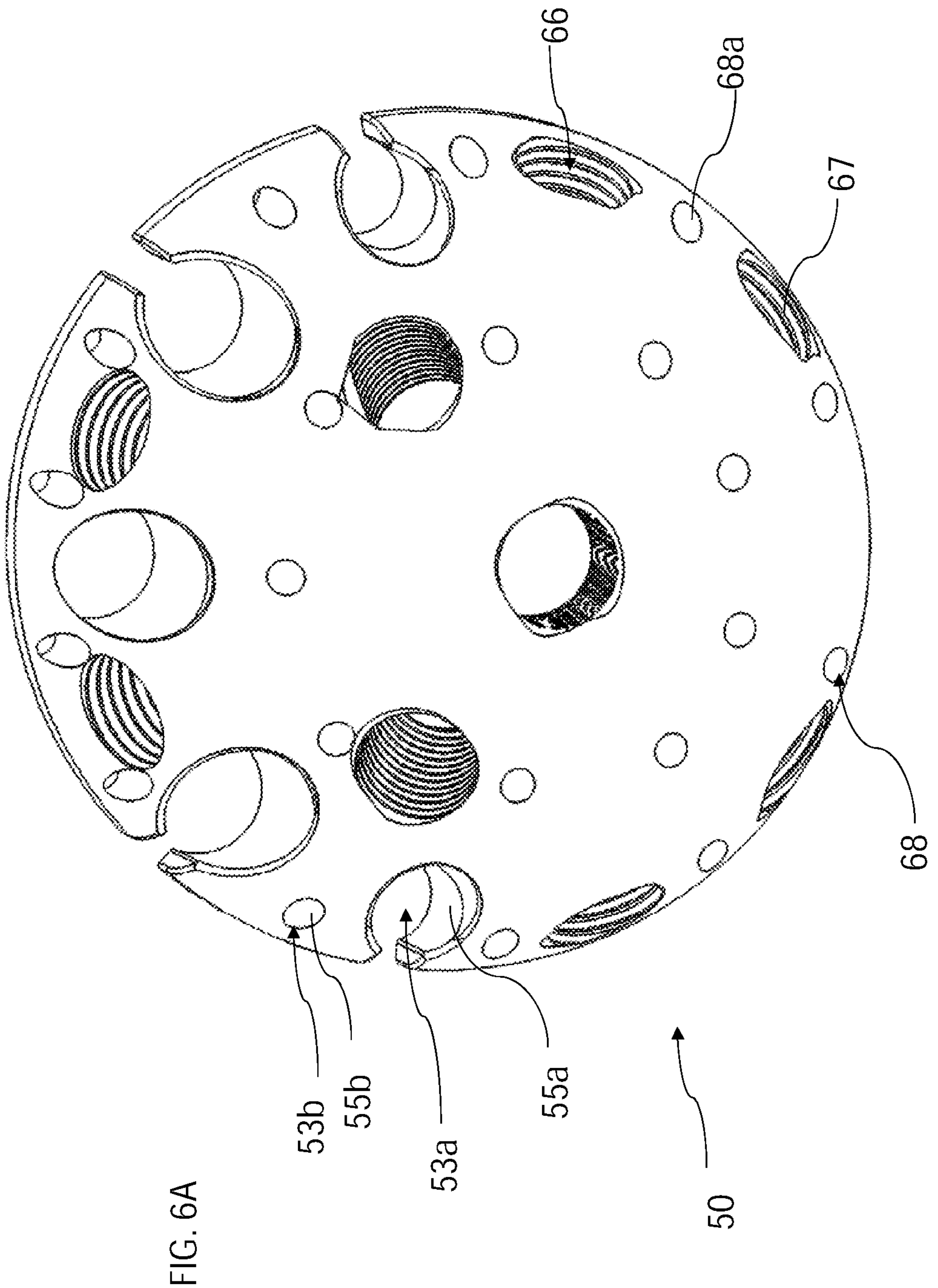
FIG. 6A illustrates a rear view of the embodiment of the positioning device of FIGS. 3-5.
Figure 6B:
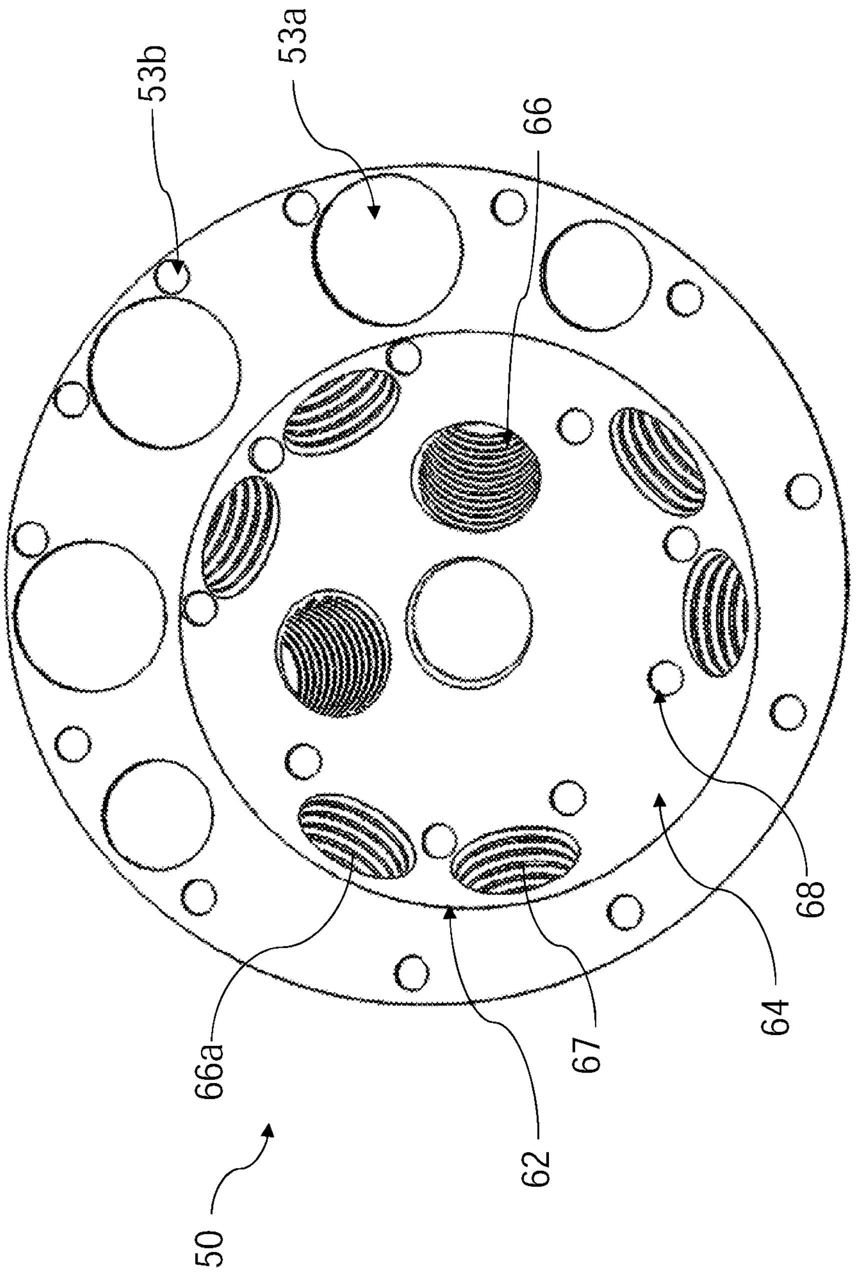
FIG. 6B illustrates a top view of an embodiment of the positioning device.
Figure 7B:
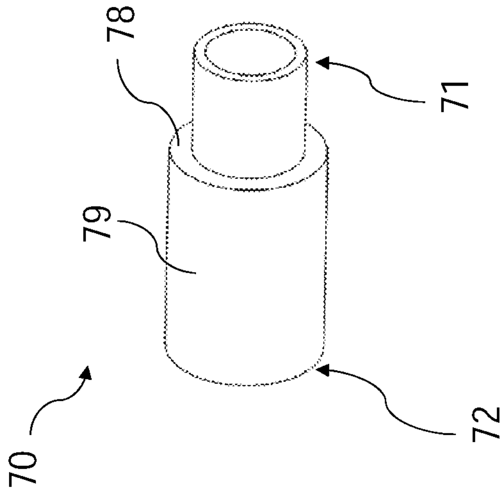
FIG. 7B illustrates a side perspective view of the guide member of FIG. 7A.
Figure 7A:
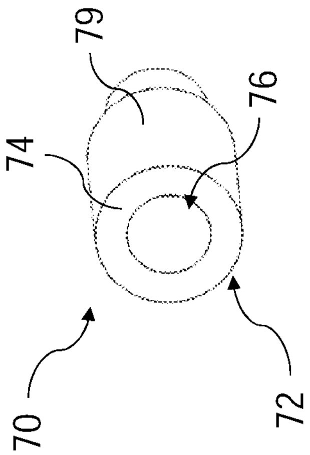
FIG. 7A illustrates a perspective end view of an embodiment of a guide member (bushing) structured to aid in bone tissue preparation.
Figure 8A:
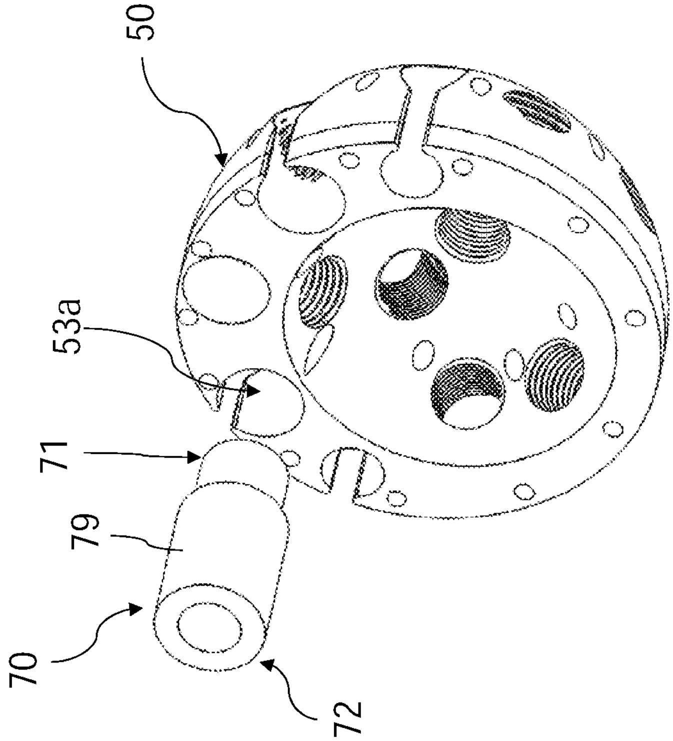
FIG. 8A illustrates a perspective view of an embodiment of the body of the positioning device relative to the guide member of FIGS. 7A and 7B.
Figure 8B:
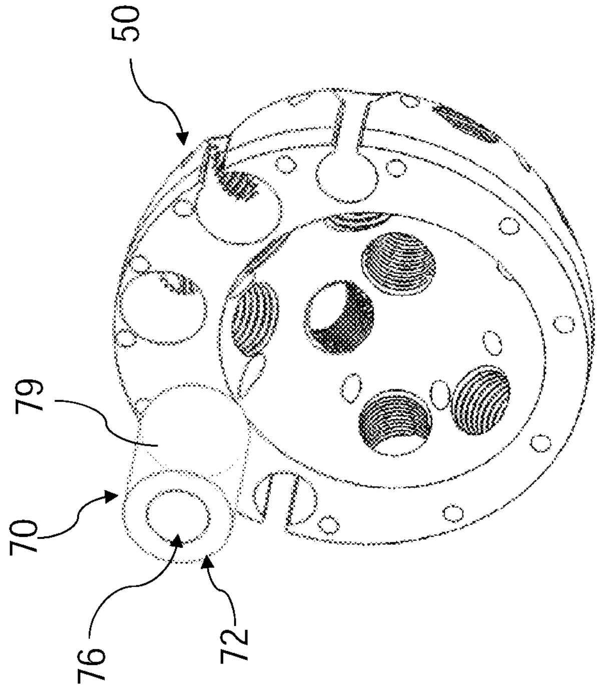
FIG. 8B illustrates a perspective view of the embodiment of FIG. 8A with the guide member inserted into the body of the hip positioning device.

As best shown in FIG. 4 and according to this embodiment, the inner edge 58 of the positioning device 50 defines a circular or substantially circular opening 60 extending into a cavity 62 defined by an inner concave surface 64. The opening 60 and cavity 62 are eccentrically offset in relation to a center axis of the positioning device 50 and more specifically the outer convex surface 56. This eccentric offset enables the size of the cavity 62 to be maximized. Alternatively, the opening 60 and cavity 62 can be centrally aligned, but the maximal diameter of the supports coupling with the implant body bores (55*a* and 113 of FIG. 10A) will be reduced. Referring specifically to FIGS. 6A and 6B, the inner concave surface 64 further includes a plurality of spaced inner openings or bores 66, 68 having an interior surface 66*a*, 68*a* and which extend from the inner concave surface 64 to the outer convex surface 56. According to this specific embodiment, the plurality of bores 66 may extend along intersecting axes $Q_1'$, $Q_2'$, $Q_3'$, . . . $Q_n'$ as shown in FIG. 5. The bores 66, 68 and 53*b* may extend along parallel axes or may extend along non-parallel axes. As shown in the illustrated embodiments, the bores 66, 68 and 53*b* have a circular cross-section. Alternatively, however, the cross sections of one or more of the bores 53*b* and bores 66 may comprise other suitable shapes. As shown, one or more of the inner openings or bores 66 have inner surface features 67 such as threads, however such inner surface features 67 may not be required in some embodiments.

The positioning or templating device 50 can be structured to accept or be compatible with an embodiment of one or more guide members 70 or guides as shown in FIGS. 7A-8B. According to at least one version, the guide member 70 a first end 71 and an opposing second end 72. More specifically, the guide member 70 is defined by a body having a distal cylindrical portion 71 that is sized to be fitted within one or more of the channels 53*a* and an adjacent proximal cylindrical portion 79, extending to the second end 72. The outer diameter of the distal cylindrical portion 71 is smaller than that of the proximal cylindrical portion 79, wherein a portion of the proximal cylindrical portion 79 forms a shoulder 78 configured and sized to act as a mechanical stop. According to this embodiment, the second end 72 of the guide member 70 includes a guide interface 74 that is structured to engage or contact a piece of medical equipment and a guide channel 76 extending through the entire guide member 70 that partially accepts a portion of the medical equipment (not shown), such as a drill, mill, reamer or threading tool. The shoulder 78 prevents over-insertion of the guide member 70 relative to the positioning device 50. Overall, the guide member 70 further aids in the stabilization of the medical equipment used during the process of preparing the host bone tissue 3 (FIGS. 1, 2, 39-41, 43A and 43B) for accepting the medical implant. The preparation process may include any process to alter and/or sculpt the host bone tissue 3 (FIGS. 1, 2, 39-41, 43A and 43B) such that the medical implant can be securely seated and secured. Any number of guide members 70 may be used during the templating process as one or more of the guide members 70 may be structured to function with one or more different pieces of medical equipment.

Figure 9B:
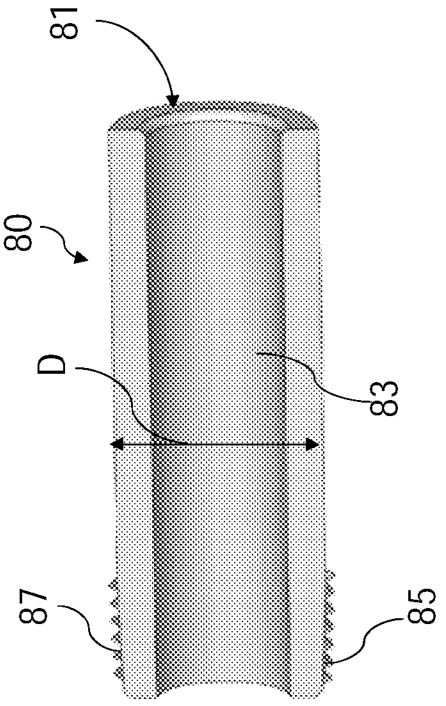
FIG. 9B illustrates the side view of FIG. 9A, shown in section.
Figure 9A:
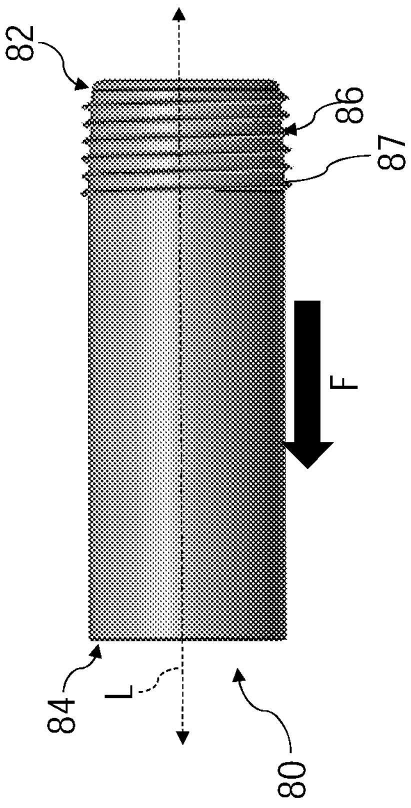
FIG. 9A illustrates a side view of an embodiment of a guide member for the threaded bores of the cavity of the body.
Figure 9C:
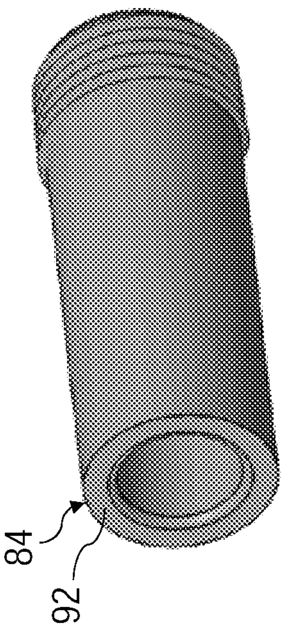
FIG. 9C illustrates the side perspective view of the guide member of FIGS. 9A-B.
Figure 9D:
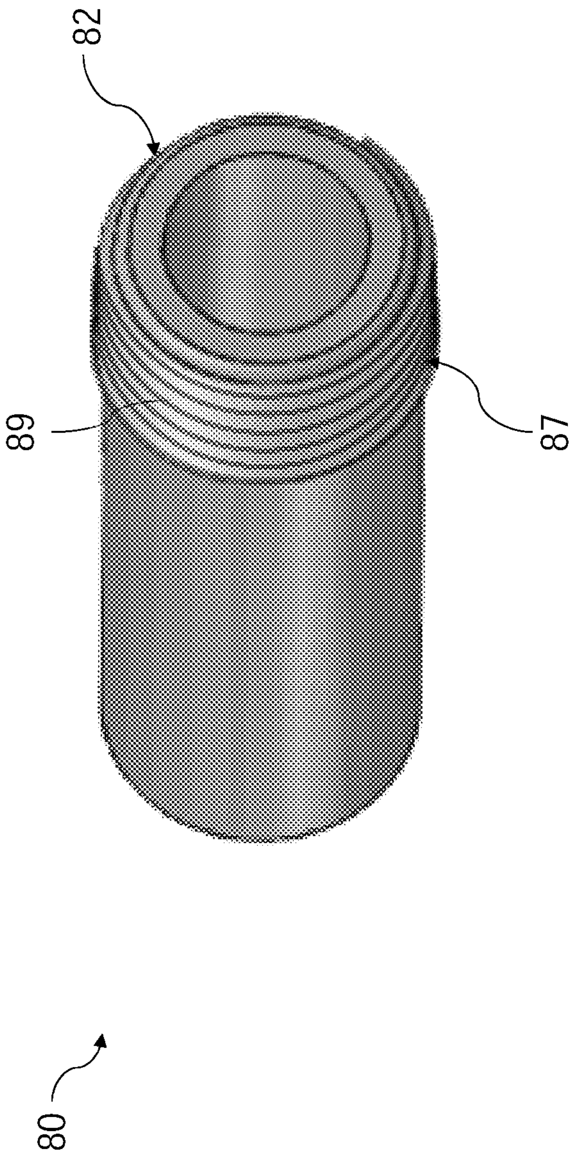
FIG. 9D illustrates the side perspective view of the guide member of FIGS. 9C, taken 180 degrees therefrom.
Figure 9E:
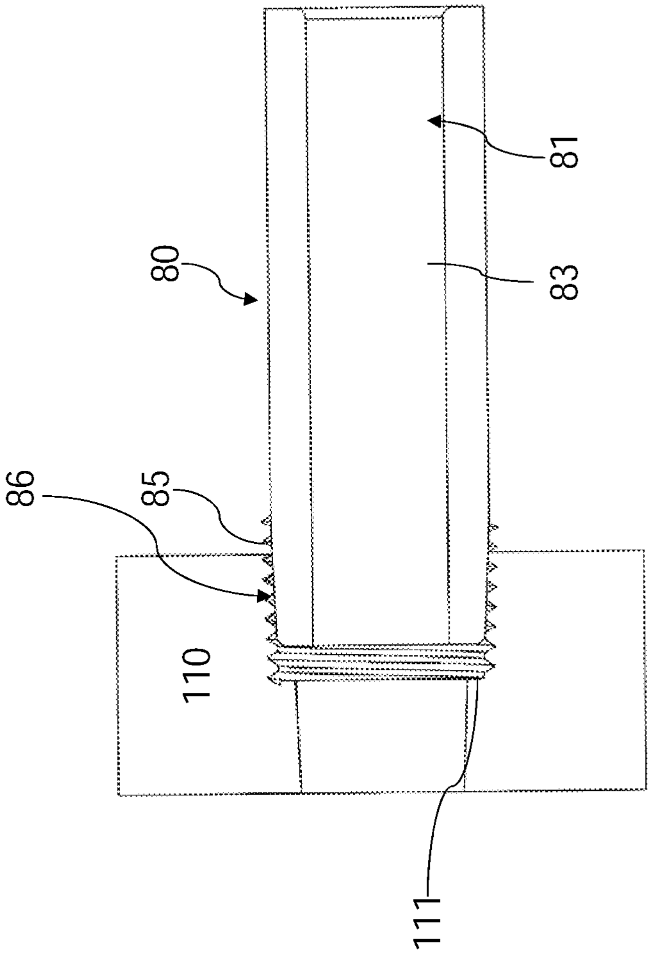
FIG. 9E illustrates a cross sectional view of the guide member of FIGS. 9A-D coupling to an embodiment of a body of the medical implant assembly.
Figure 9G:
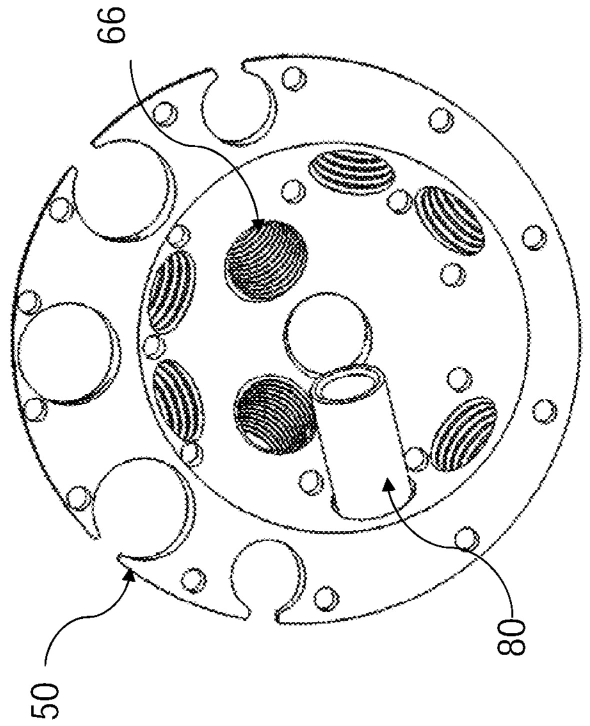
FIG. 9G illustrates the guide member of FIGS. 9A-E coupled with the positioning device.
Figure 9F:
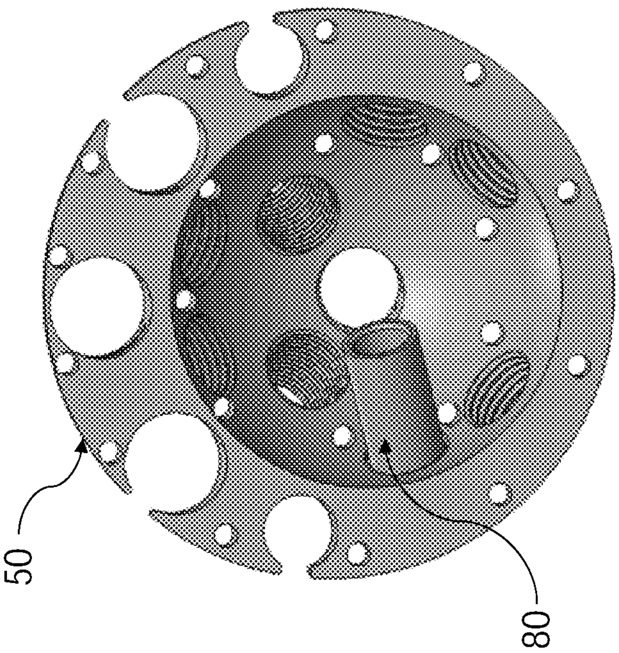
FIG. 9F illustrates the guide member of FIGS. 9A-E coupled with the positioning device.
Figure 9H:
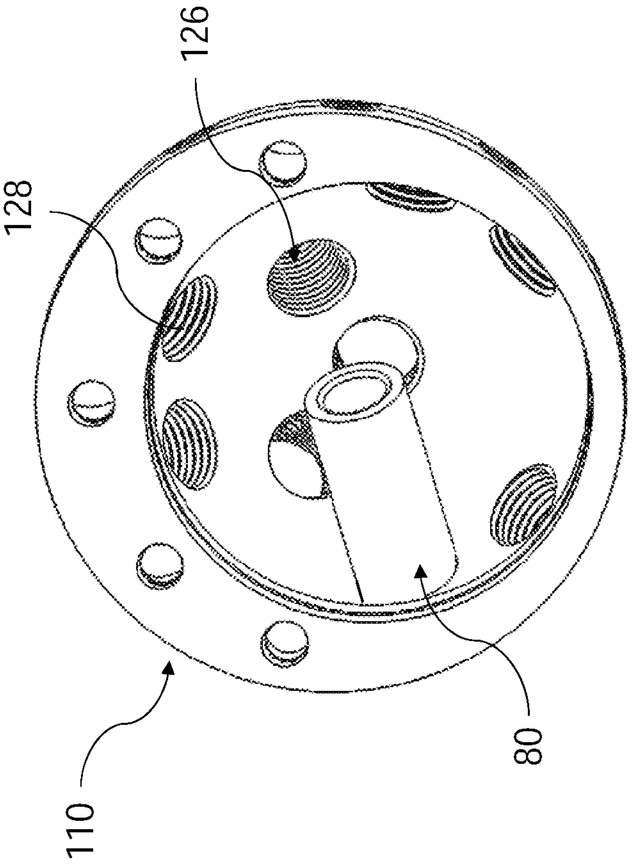
FIG. 9H illustrates the guide member of FIGS. 9A-E coupled with the body of the implant assembly.

Now referring to FIGS. 9A-H, a guide member 80 made in accordance with another exemplary embodiment is herein described that can be used in the implant assembly 200. For purposes of this discussion, a single guide member 80 is discussed. It will be apparent, however, that one or more of the features described in relation to the guide member 80 may be included in one or more of the various embodiments of guide members described herein. More specifically, the guide member 80 has a substantially circular cross-section and extends along a guide axis L extending through a first end 82 and an opposing second end 84. The first end 82 comprises a body interface portion 86 and the second end 84 comprises an engagement portion for engagement with a bone preparation tool (not shown), such as a drill or mill or threaded tool. As shown, the diameter D of the guide member 80 is substantially constant along a longitudinal guide axis L. The body interface portion 86 includes one or more engagement surfaces 87 that can form a mechanical fit (see FIG. 9E) or a friction fit with the interior surface of the bore 66 of the templating device 50 shown in FIGS. 9F and 9G and the interior surface of the inner bore 126 of the body 110 shown in FIG. 9H. As shown in FIGS. 9A-C, the body interface portion 86 includes a plurality of surface features, such as external threads 85. As alternatively shown in FIG. 9D, however, the engagement surface 87 of the guide member 80 can be a tapered surface 89. The first end 82 defines an axial through opening 81 defined by an annular interior surface 83. As noted, the second end 84 of the guide member 80 is configured to engage a bone tissue preparation tool (not shown) such as a drill, mill or threading device. More specifically, the second end 84 of the guide member 80 includes a second end surface 92 that can be planar, rounded, pointed, or any configuration suitable to engaging a bone preparation tool.

Figure 10A:
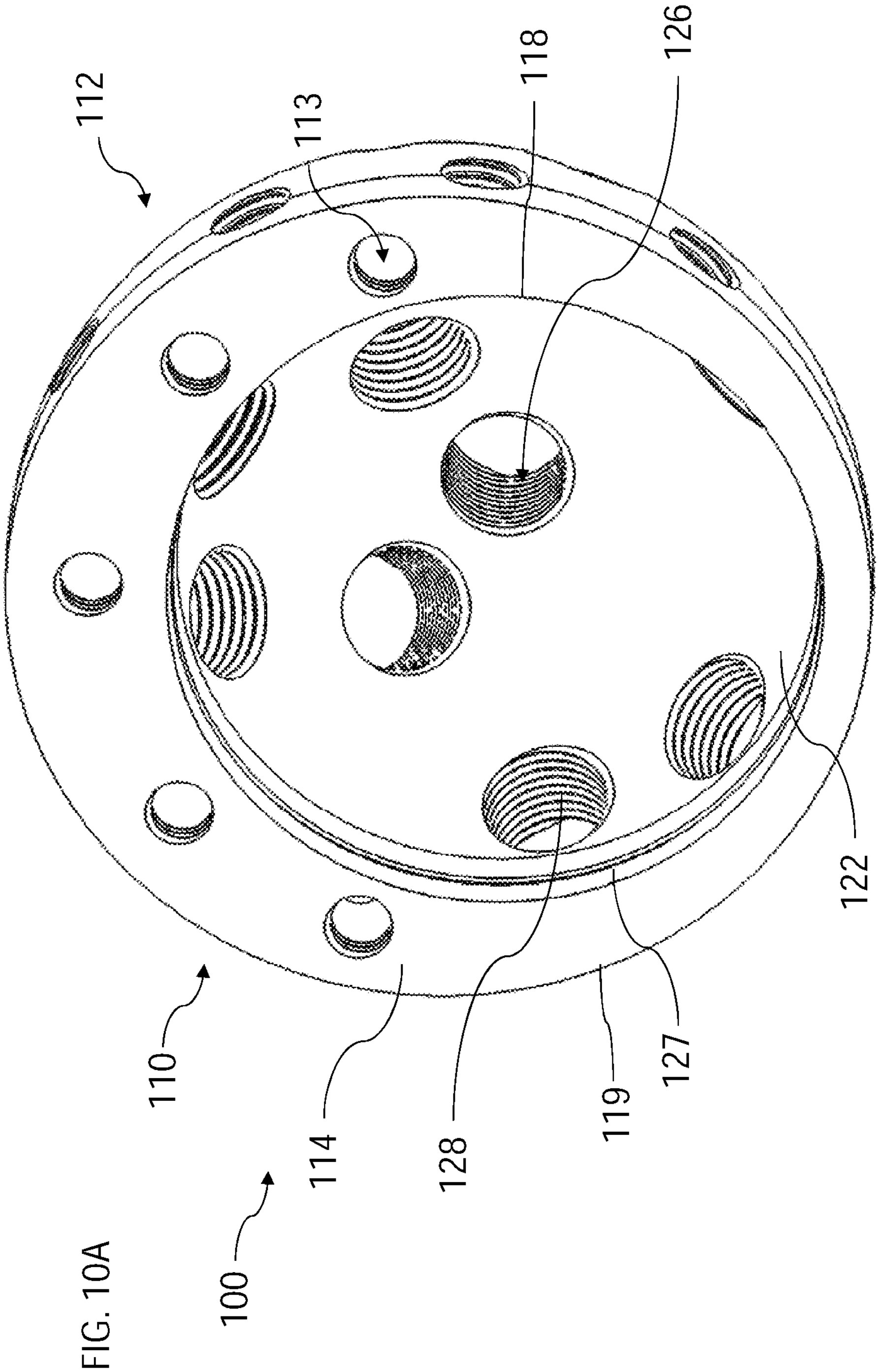
FIG. 10A illustrates a top perspective view of an embodiment of the body of the hip implant assembly.
Figure 10B:
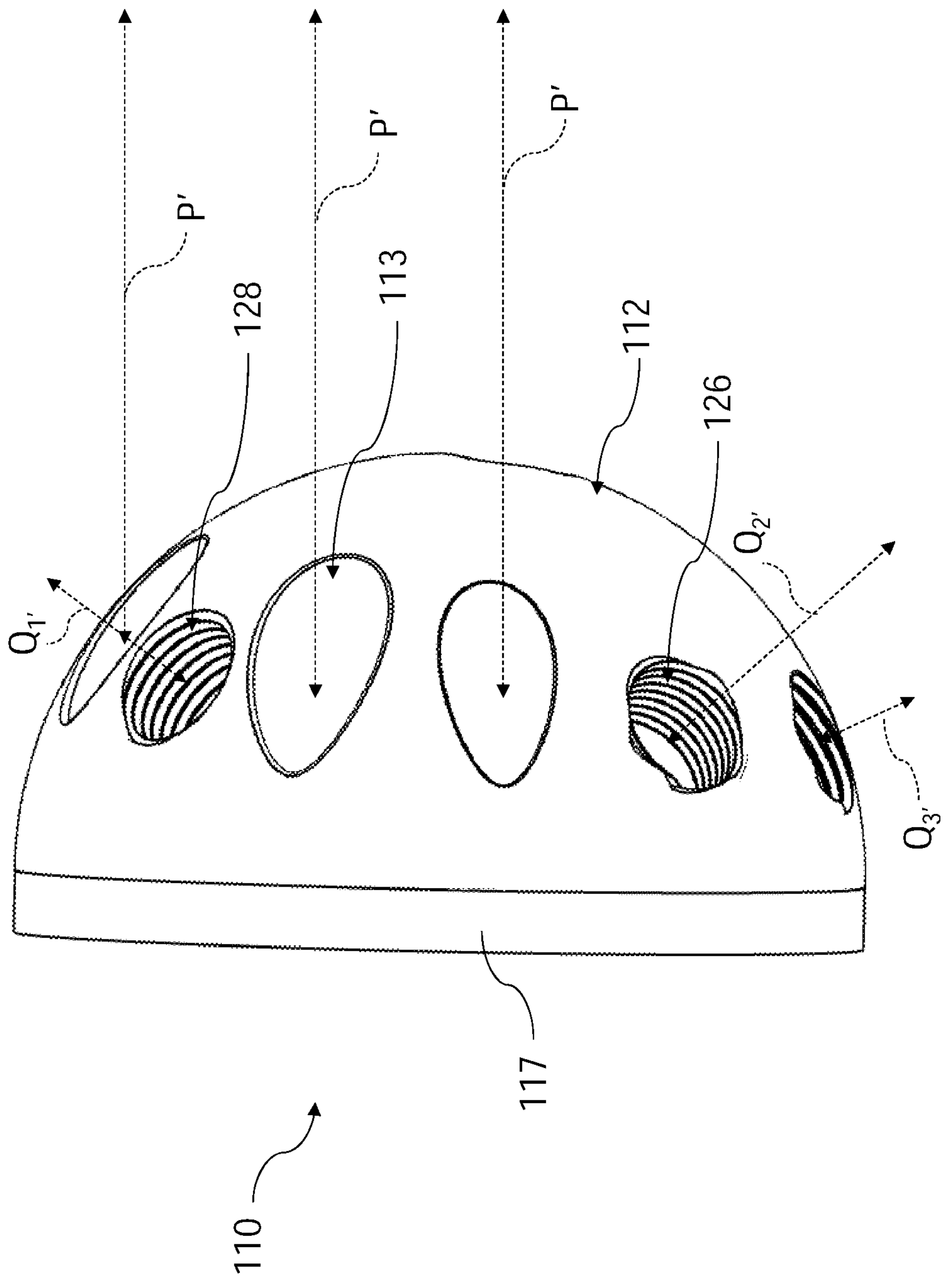
FIG. 10B illustrates a side perspective view of an embodiment of the body of the hip implant assembly of FIG. 10A.
Figure 11:
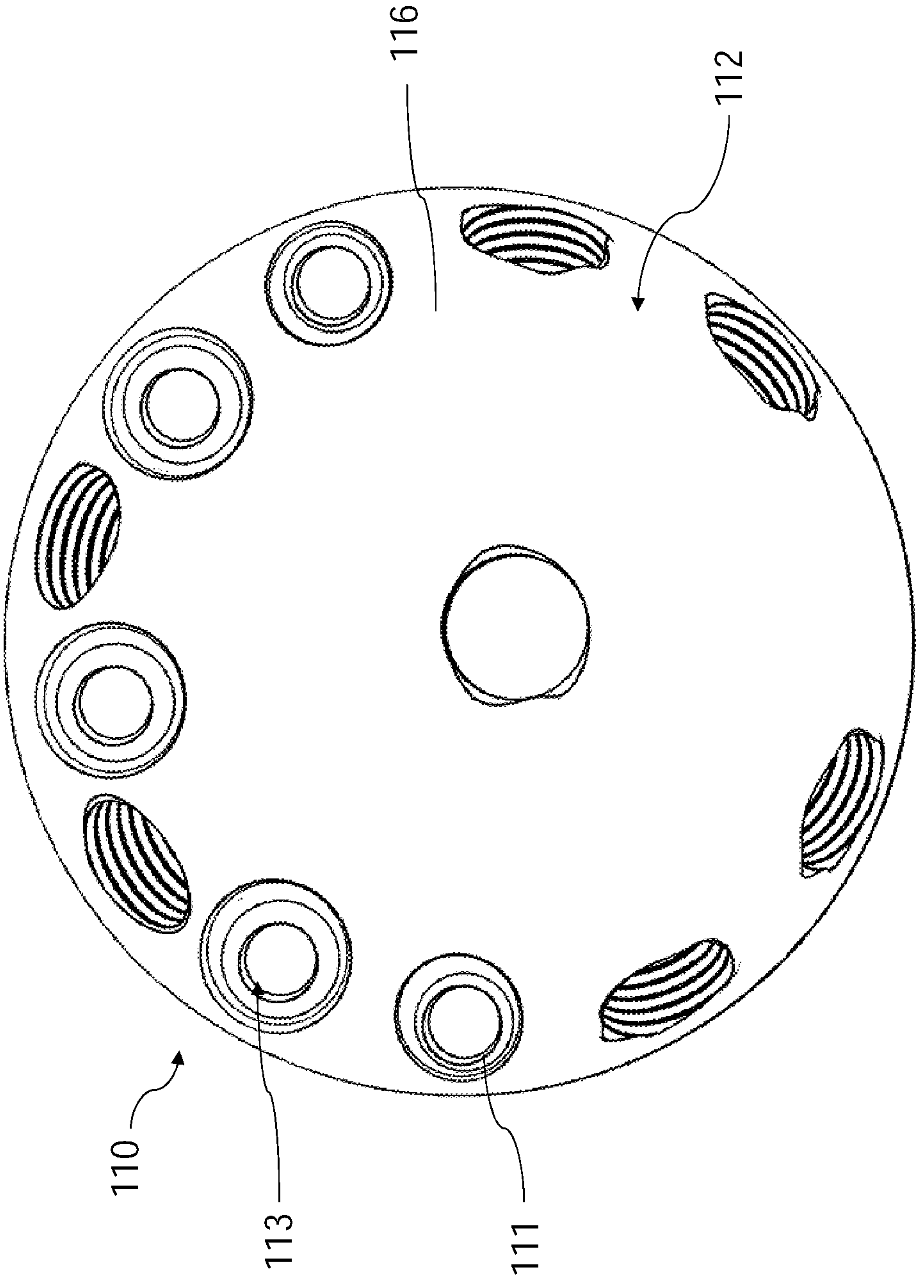
FIG. 11 illustrates a rear plan view of the body of the hip implant assembly of FIGS. 9 and 10.

Referring to FIGS. 10A-11, an embodiment of a medical implant assembly 100 includes a shell or body 110 having a generally hemispherical structure 112 that includes a rim surface 114 or rim with an outer edge 119, and an outer surface 116, which as according to this embodiment is a convex surface and in which the rim surface 114 is substantially planar. In an embodiment, a peripheral transition surface 117, FIG. 10A-B, is located between the outer edge 119 and the outer convex surface 116. In some embodiments, however, the transition surface 117 may alternatively define one or more surface features and/or may extend radially from the outer convex surface 116. The outer edge 119 may be circular or elliptical in shape wherein an inner edge 118 of the rim surface 114 is circular. A plurality of bores 113, each defined by an inner surface 115 (FIG. 15), are disposed about a portion of the periphery of the body 110 and extend from the rim surface 114 to the outer convex surface 116 along parallel or approximately axes P' as best shown in FIG. 10B. Referring specifically to FIG. 11, the plurality of bores 113 each include an inner lip 111 (FIG. 9E) that aids in securing a corresponding support 140 (FIGS. 12-14) within the bore 113, however, other embodiments do not necessarily include an inner lip 111.

Figure 15:
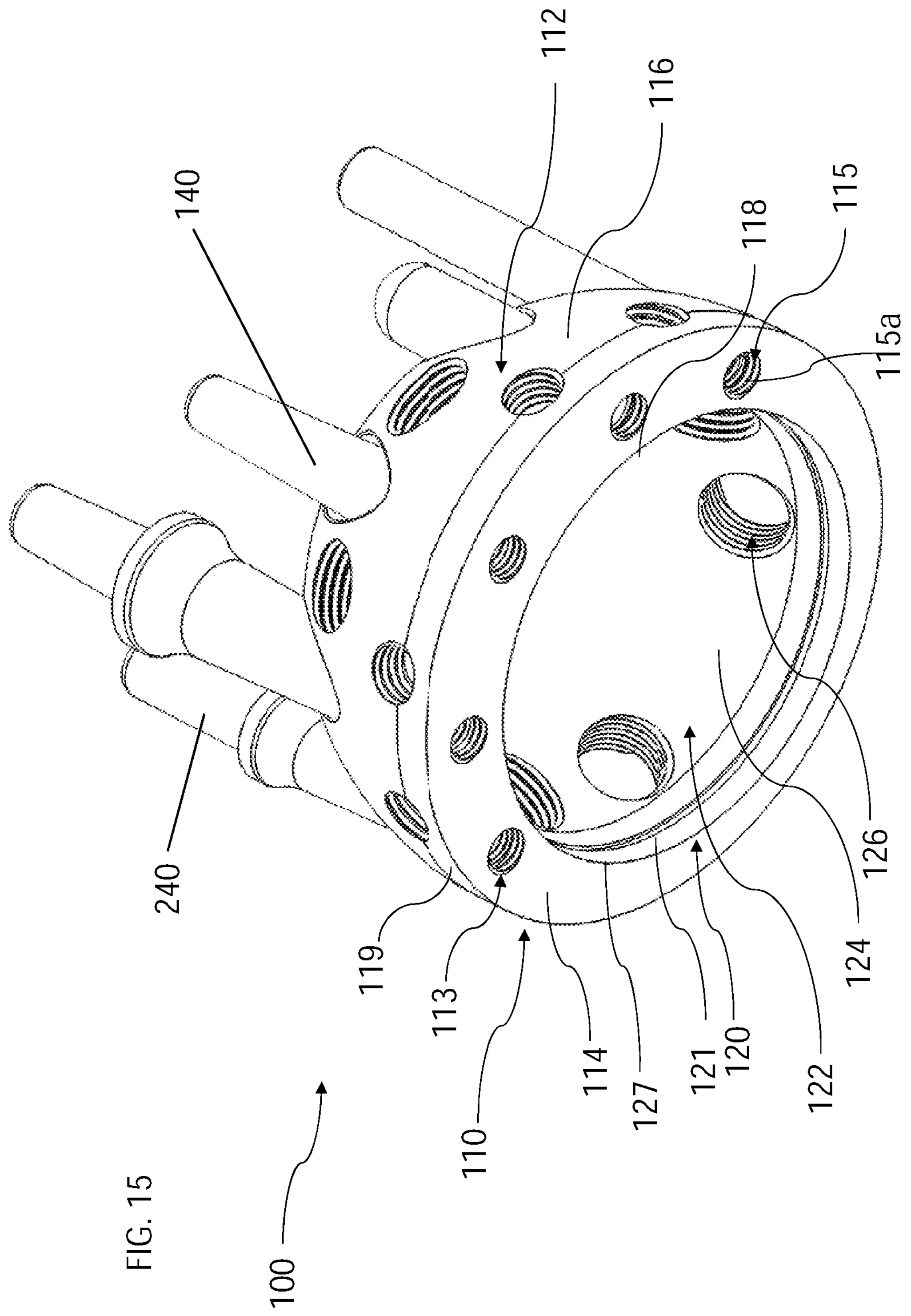
FIG. 15 illustrates a perspective view of an embodiment of the body of the medical implant assembly of FIGS. 10A-11 coupled to several embodiments of supports, including those depicted in FIGS. 12-13.
Figure 32:
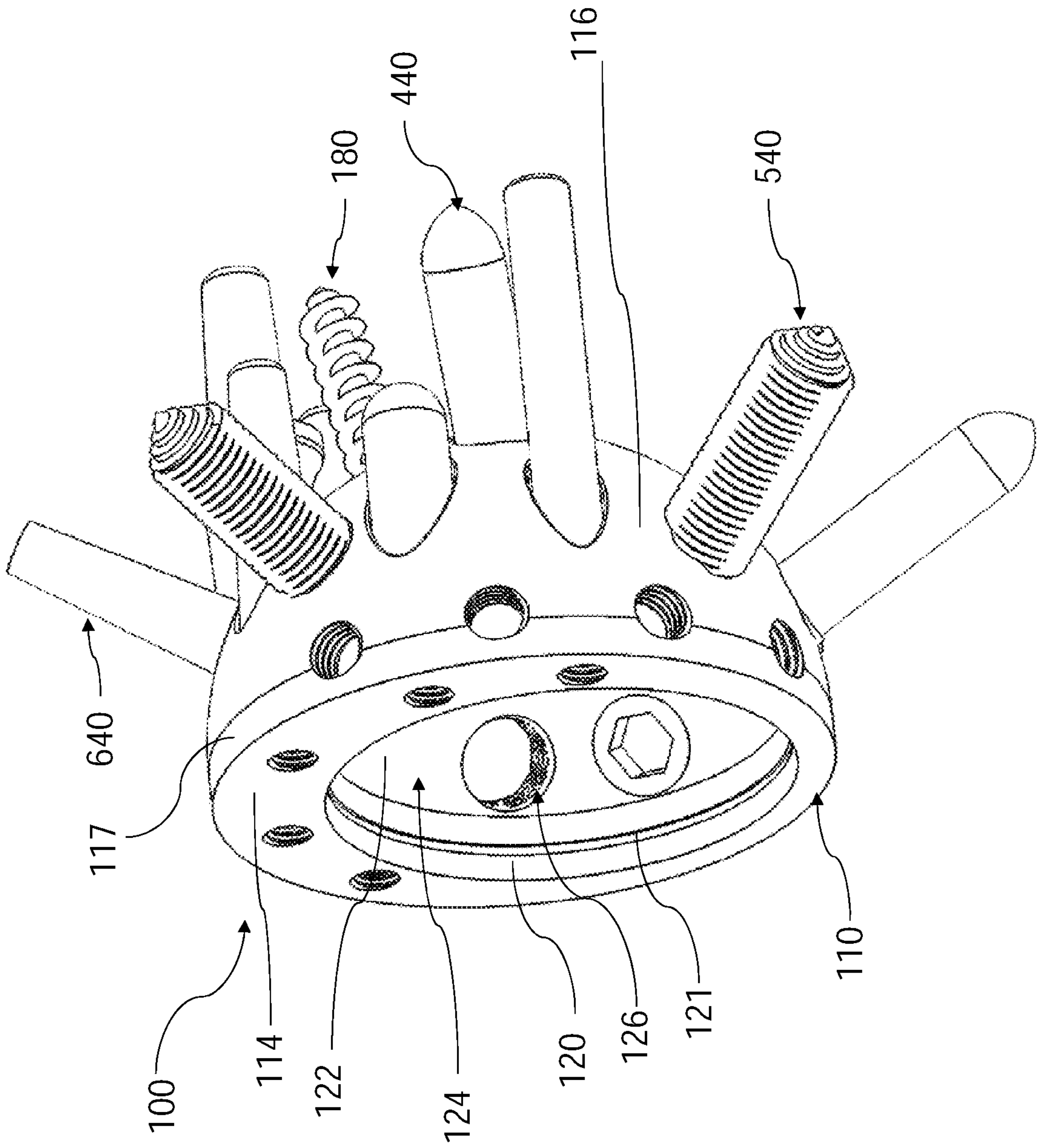
FIG. 32 illustrates a side perspective view of the body of the medical implant assembly with several support members attached through internal and external openings.
Figure 33B:
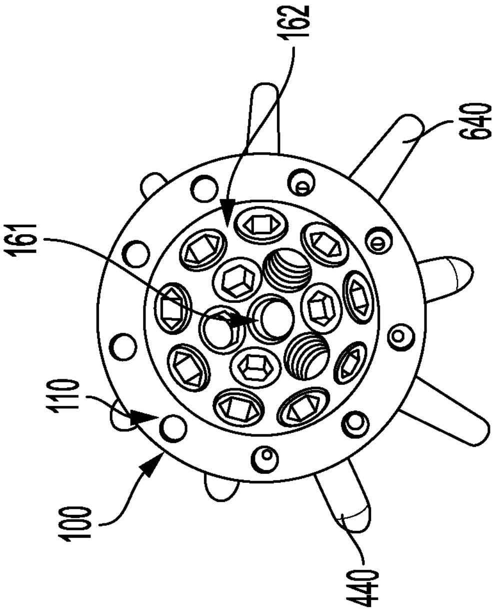
FIG. 33B illustrates a top perspective view of the embodiment of FIG. 33A.
Figure 33A:
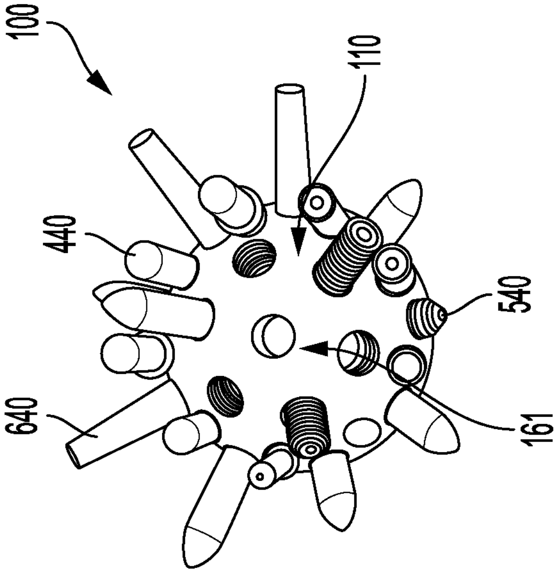
FIG. 33A illustrates a bottom perspective view of an embodiment of the medical implant assembly showing a plurality of different embodiments of supports coupled to the body.
Figure 33C:
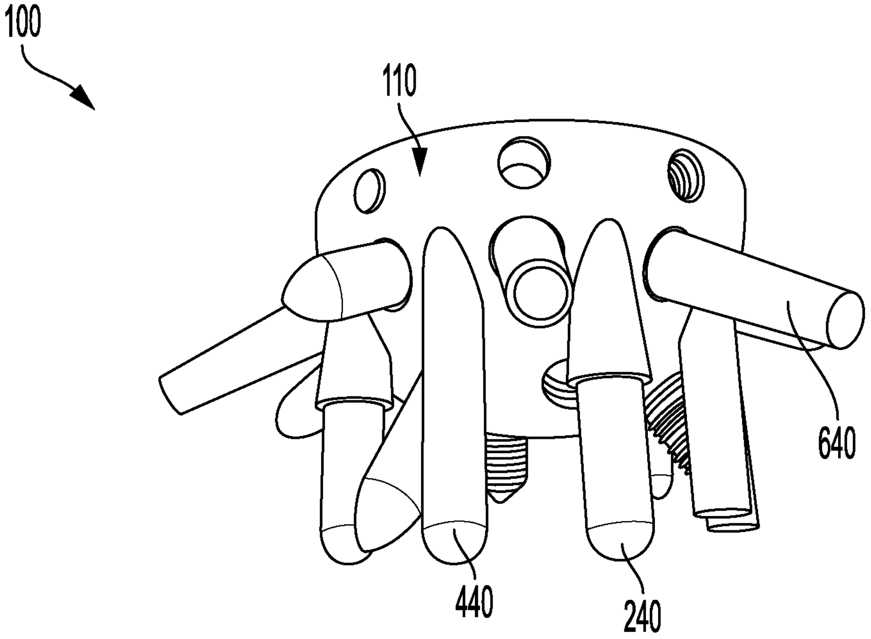
FIG. 33C illustrates a side perspective view of the embodiments of FIGS. 33A and 33B.

With further reference to FIGS. 10A, 11 and 15, the inner edge 118 of the rim surface 114 defines a substantially circular opening 120 (FIGS. 15 and 32) extending into a cavity 122 defined by an interior surface 124 (FIGS. 15 and 32), which according to this embodiment is a concave surface. As shown, the cavity 122 is eccentrically aligned (off-center) relative to the outer edge 119 and more specifically a center axis of the body 110. This eccentric alignment enables the cavity 122 (FIGS. 15 and 32) to be larger in diameter while still allowing room for the plurality of bores 113 along a wider section of the rim surface where bone is most likely to be present in the damaged host bone tissue 3 or host tissue. The larger cavity 122 can therefore accept a larger insert 4 (see FIG. 1), which increases the overall stability of the prosthetic hip 1 and therefore reduces the risk of disengagement or dislocation of the ball 6 from the insert 4 (see FIG. 1). In another alternative embodiment, the cavity 122 can be centrally aligned in relation to the outer edge 119 and the center axis of the body 110. In an embodiment, an inner circumferential surface 127 extends between the inner edge 118 of the rim surface 114 and the interior concave surface 124. In the embodiment of the body 110 shown, the inner circumferential surface 127 defines one or more surface features 121 (FIGS. 15 and 32) that can aid in the attachment or positioning of the insert 4 (see FIG. 1) of the prosthetic hip 1 (see FIG. 1). For example, the one or more surface features 121 (FIGS. 15 and 32) may include a circumferential groove (not shown) that is configured to accept a complementary circumferential ridge (not shown) of the insert 4, FIG. 1, to enable a snap-fit engagement. Other embodiments of the body 110 may not include the one or more surface features 121, but may instead include an additional tapered surface that is configured to engage a tapered surface (not shown) of the insert 4, FIG. 1. Other interfacing features or configurations between the body 110 and the insert 4, FIG. 1, will be readily apparent.

The interior concave surface 124 of the body 110 includes a plurality of spaced apart inner bores or inner openings 126 that are defined by an interior surface 128. Each of the plurality of inner bores 126 extends entirely through the body 110 between the interior concave surface 124 and the outer convex surface 116. Unlike the plurality of bores 113, the plurality of inner bores 126 extend along intersecting or non-parallel axes $Q_1'$, $Q_2'$, $Q_3'$, . . . $Q_n'$ as shown in FIG. 10B. Other embodiments of the body 110 may include a plurality of inner bores 126 in which two or more of the inner bores 126 extend along parallel axes. As shown in the illustrated embodiments, the bores 113 and the inner bore 126 are defined by a circular cross-section. However and in other embodiments, one or more of the bores 113 and inner openings 126 may have other suitable cross-sections (e.g., elliptical, oval, etc.) as illustrated, for example, in FIGS. 35A-38.

Figure 12:
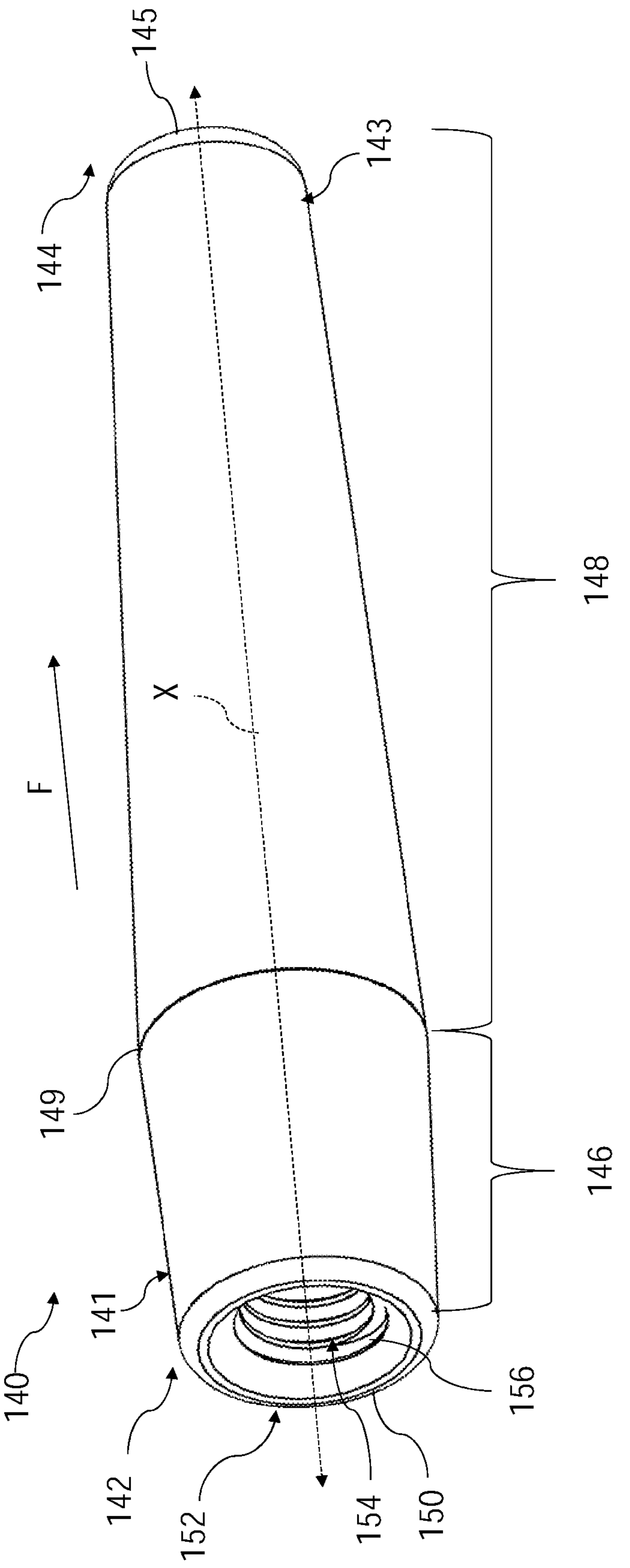
FIG. 12 illustrates a perspective side view of an embodiment of a support of the medical implant assembly.
Figure 13:
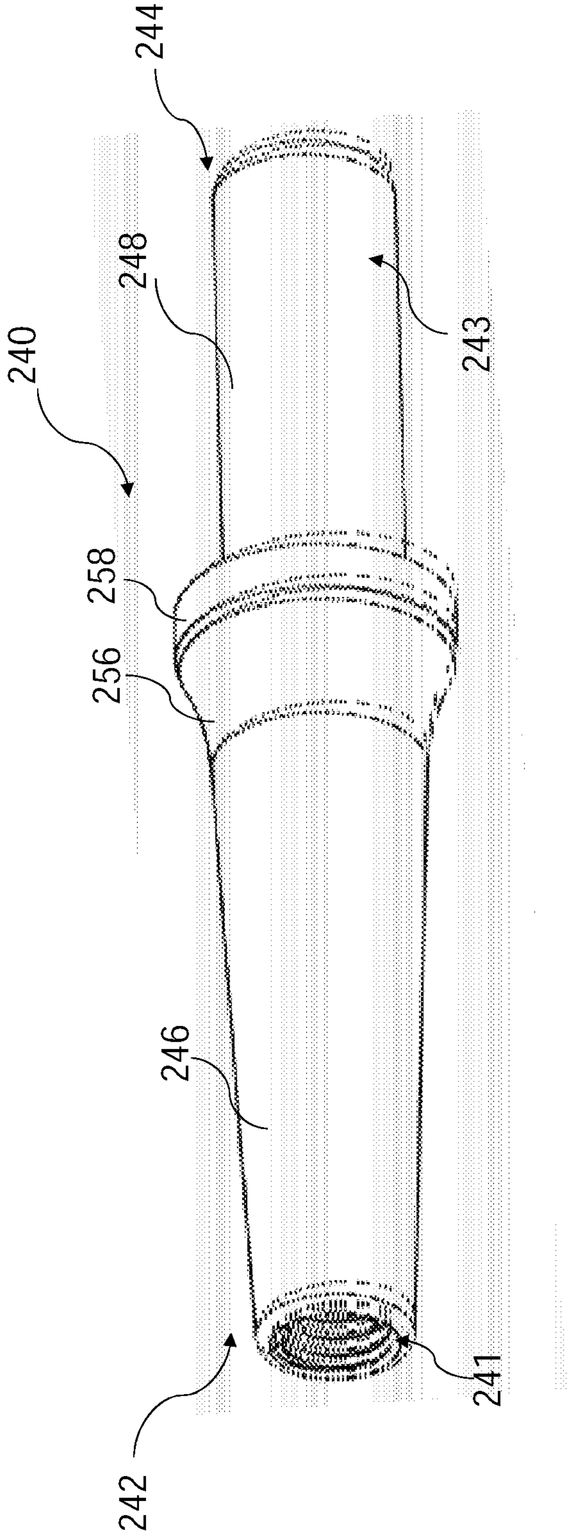
FIG. 13 illustrates a perspective side view of another embodiment of a support of the medical implant assembly.
Figure 14:
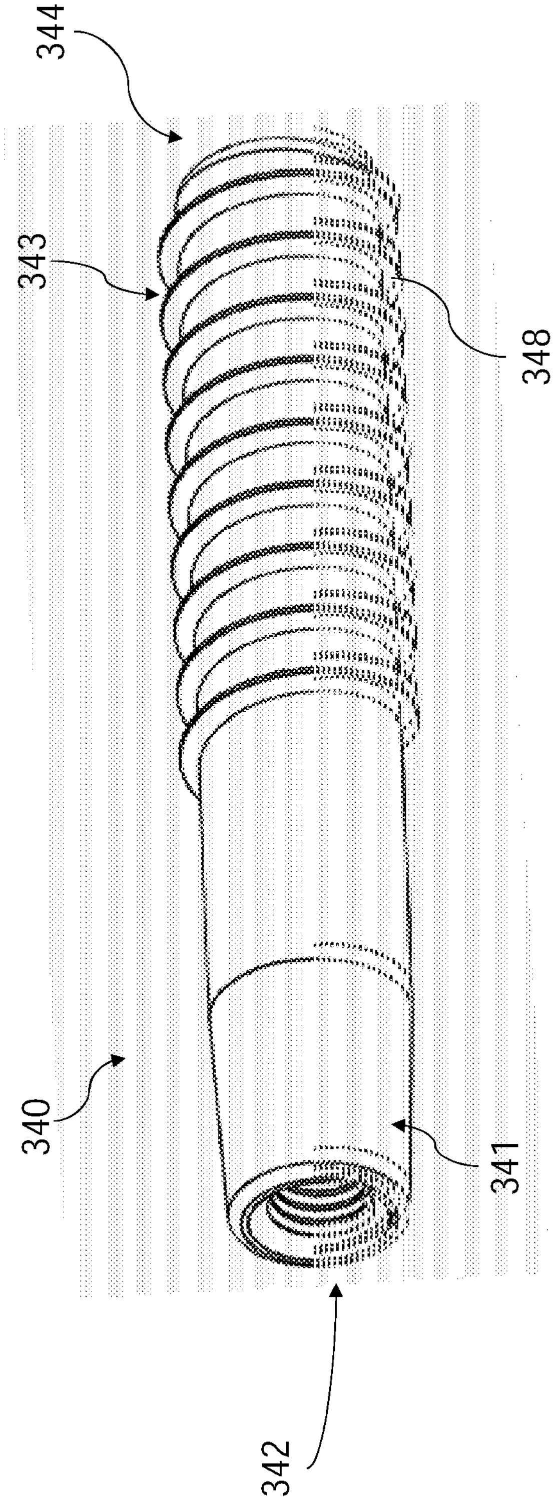
FIG. 14 illustrates a perspective side view of another embodiment of a support of the medical implant assembly.

It will be understood that other embodiments of the body 110 may have different configurations than those described above. For example, at least one version of the body 110 can be envisioned in which the rim surface 114 includes a plurality of bores and/or channels disposed in spaced relation entirely around its circumference. The overall size of the rim surface 114 and the number of bores and/or bores defined therein depends on the size of the body 110, which ultimately depends on the patient receiving the medical implant assembly 100. For example, when a larger body 110 is used, there may be sufficient room for bores to be defined all around the rim surface while still providing a large cavity 122 to accommodate as large an insert 4 (see FIG. 1) as possible. As shown in FIGS. 12-14, one or more body extensions or supports 140 are removably coupled to the body 110 as received by the corresponding bores 113 and inner bores 126. The one or more supports 140 are configured to engage the host bone tissue 3 (see FIGS. 1, 2, 39-41, 43A and 43B), and provide support and stability to the body 110 while bone ingrowth and ongrowth occurs. The use of one or more supports can make it unnecessary for the body 110 of the disclosed medical implant assembly 100 to be in substantial direct contact with the host bone tissue 3 (see (FIGS. 1, 2, 39-41, 43A and 43B). As shown in the various embodiments, the body 110 is dimensioned to receive the insert 4 (see FIG. 1) of the prosthetic hip 1 (see FIG. 1). As shown in FIGS. 12-14 and 21A-C, the one or more supports 140, 240, 340 can have a variety of shapes and sizes depending on the characteristics of each surgical site and the preferences of the surgeon. As to those depicted, the supports 140 are defined by extending elongate bodies having a cylindrical or substantially cylindrical configuration, each extending along parallel axes P' (FIG. 10B) and fasteners or the like having outer threaded surfaces extending along axes Q (FIG. 5). As previously mentioned with regard to hip revision cases, the host bone tissue 3 (see FIGS. 1, 2, 39-41, 43A and 43B) is often compromised over time by osteolysis or necrosis. Consequently, there may not be enough healthy host bone tissue in contact with the body 110 to properly secure a prosthetic hip 1 (see FIG. 1) using a prior art shell 2 (see FIG. 1). Accordingly, the disclosed medical implant assembly 100 of the medical implant system 200 comprises one or more supports 140 that act to support and stabilize the body 110 without substantial direct contact between the body 110 and the host bone tissue 3 (see FIGS. 1, 2, 39-41, 43A and 43B). The one or more supports 140 are coupled to the body 110 through the bores 113 extending through the eccentric side of the rim surface 114. This latter area of the body 110 possesses the most body material and therefore creates an incredibly strong and rigid friction fit, which can be further strengthened using a fastener or the like that also prevents disengagement of the support. This strong and rigid connection is able to fully support the body 110 substantially away from host bone tissue 3 (see FIGS. 1, 2, 39-41, 43A and 43B).

Several embodiments of supports 140, 240, 340 will now be discussed to illustrate various configurations in accordance with aspects of the invention, as well as a non-exclusive number of methods for coupling one or more of the supports to the body 110 of the implant assembly 100 and 200. It should be noted that the following represents exemplary embodiments and does not represent an exhaustive list of support designs that are possible or envisioned. Many of the supports disclosed comprise finishes, features or coatings to allow and/or promote bone ingrowth and/or ongrowth in order to more permanently fix the implant 100 to the host bone tissue (see FIGS. 1, 2, 39-41, 43A and 43B).

Referring to FIG. 12, an embodiment of a support 140 is defined by an elongate member that has a substantially circular cross-section and extends along a support axis X extending through a first end 142 to an opposing second end 144. The first end 142 comprises a body engagement portion 141 that includes a first frustoconical or tapered portion 146 and the second end 144 comprises a host tissue engagement portion 143 that includes a second frustoconical or tapered portion 148 that meets the first frustoconical portion 146 at a circumferential apex 149. Accordingly, the tapering outer diameter of the support increases between the first end 142 and the circumferential apex 149 and decreases between the circumferential apex 149 and the second end 144. According to this embodiment, the first frustoconical portion 146 provides a tapered outer surface that can form a friction fit with the interior surface of the bore 113 of the body 110. In other embodiments, however, the diameter of the support cross-section can decrease between the first end 142 and the second end 144 such that the support 140 has at least one tapered end.

Figure 18:
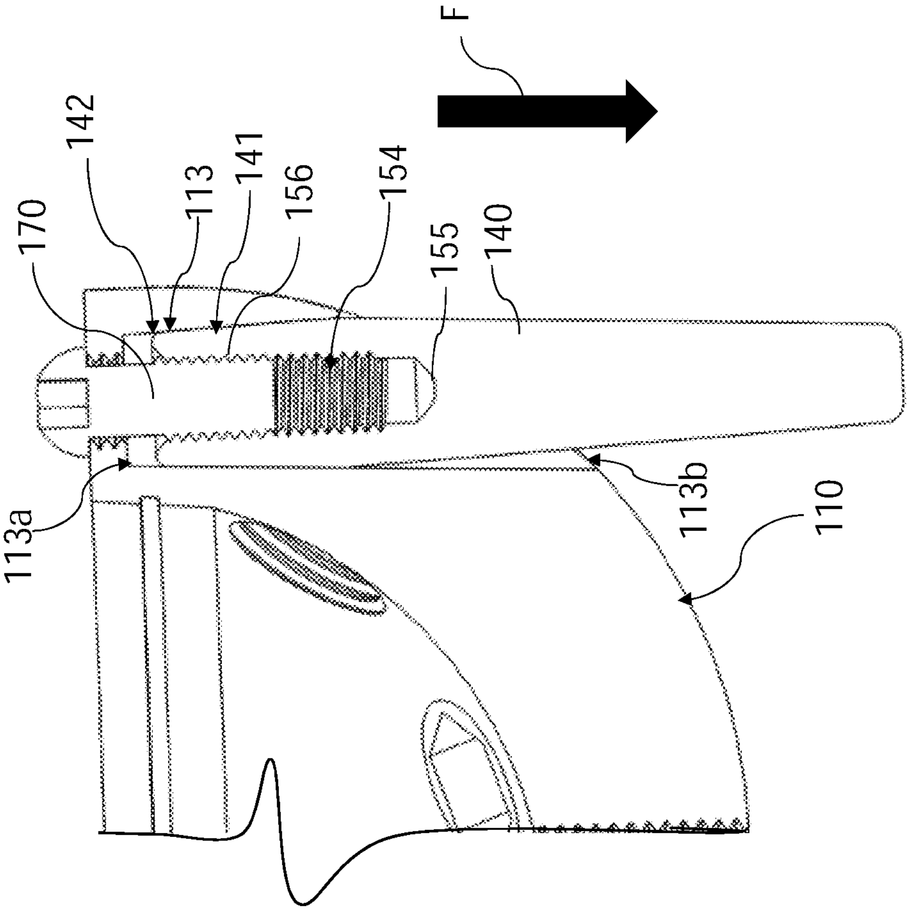
FIG. 18 illustrates a sectional side view of an embodiment of the body of the medical implant assembly with a fastener coupled to an embodiment of a support.
Figure 19:
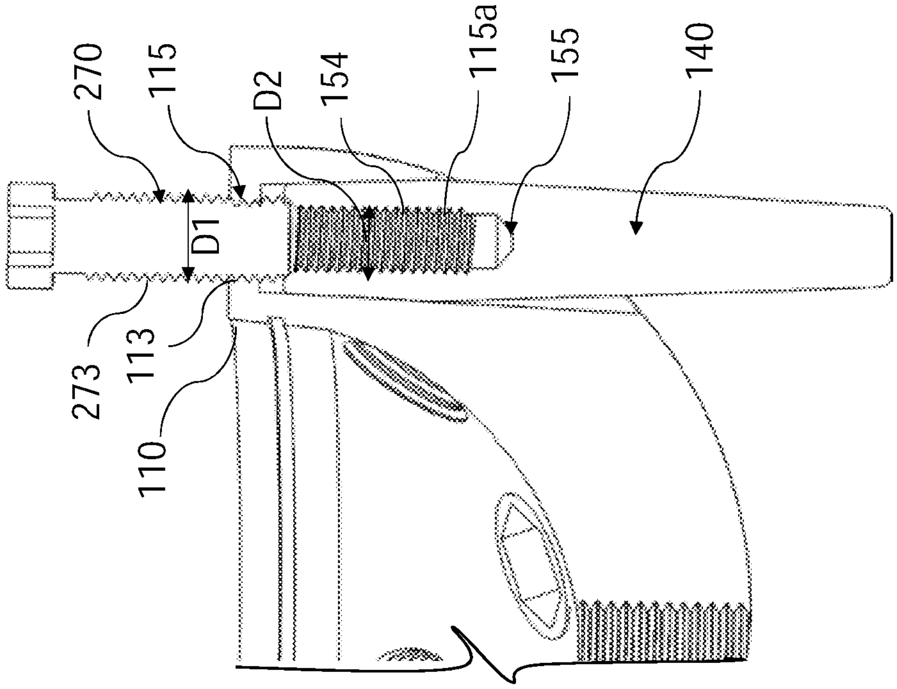
FIG. 19 illustrates a sectional side view of an embodiment of the body of the medical implant assembly with a distraction bolt engaged in the body at a first position.
Figure 34B:
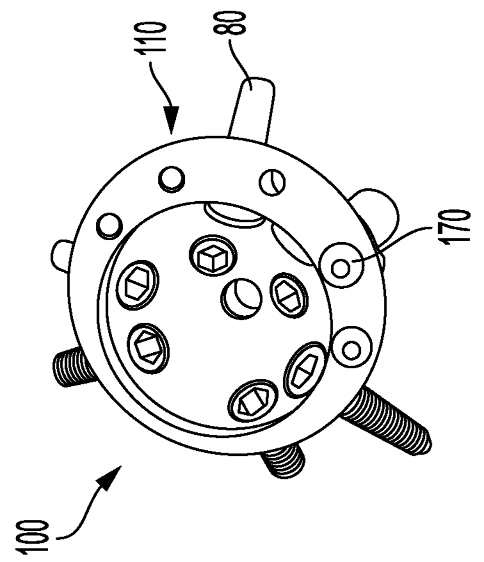
FIG. 34B illustrates a top perspective view of the embodiment of FIG. 34A.
Figure 34A:
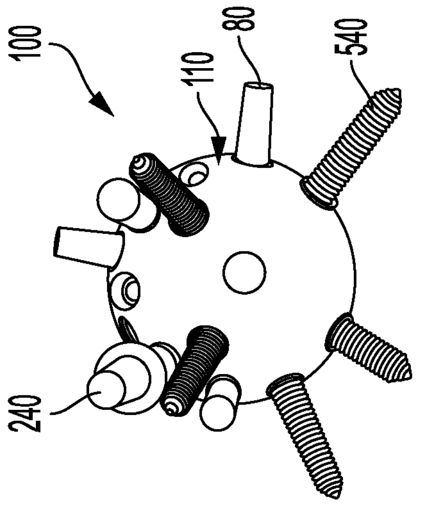
FIG. 34A illustrates a bottom perspective view of another embodiment of the medical implant assembly showing a plurality of different embodiments of supports coupled to the body.
Figure 34C:
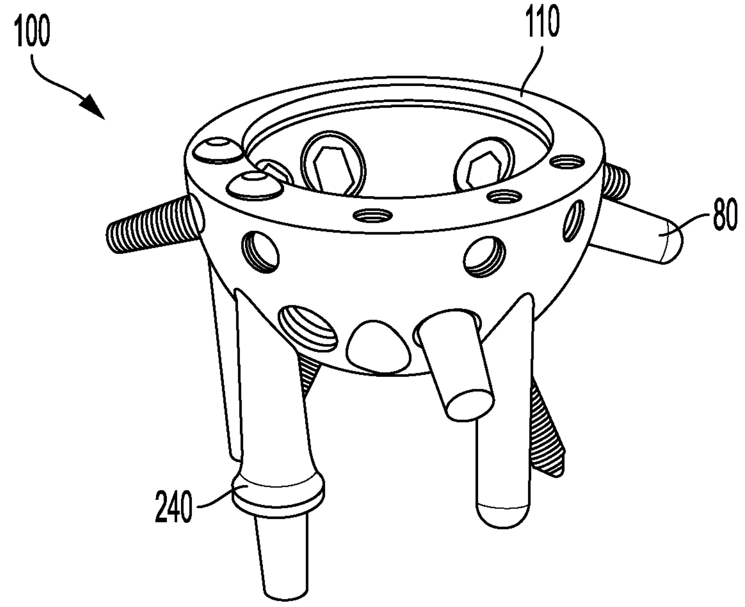
FIG. 34C illustrates a side perspective view of the embodiments of FIGS. 34A and 34B.

The first end 142 includes a first end surface 150 that defines an opening 152 into a cavity 154 surrounded by an annular inner surface 156 and having a cavity bottom 155 (FIG. 19). As shown, the annular inner surface 156 includes a plurality of surface features, such as internal threads extending at least a portion into the cavity 154, that are configured to interact with a fastener, such as a screw to further secure the support 140 to the body 110 through the bore 113. Various types of fasteners can be used for this interaction including, but not limited to fasteners 170 such as compression screws (see FIGS. 17, 18 and 34B) or other types of fasteners 170, such as other medical grade screws (see FIG. 18). Embodiments of the supports may be formed or treated to allow and/or promote bone ingrowth or bone ongrowth. For the purposes of the following discussion, a support that is configured to allow bone ingrowth and/or ongrowth includes one or more surfaces on which the bone tissue can grow into or onto. This configuration may include the use of a smooth or preferably roughened surface, porous surface, or beaded surface created by accepted methods already in use such as machining, grit blasting, casting, additive manufacturing, forging, plasma spraying, powder metallurgy and the like. In addition and also for the purposes of the following discussion, a support that is configured to promote bone ingrowth and/or ongrowth includes one or more surfaces that enhance natural bone formation, a process known as osteoinduction. Osteoinduction may be achieved for example by the inherent nature of the support or more commonly by coating at least a portion of the supports with a material that promotes or enhances the natural bone formation.

Still referring to FIG. 12, the second end 144 of the support 140 is configured to engage and be secured to the host bone tissue 3 (see FIGS. 1, 2, 39-41, 43A and 43B), for example pelvic bone tissue, in order to support and stabilize the body 110 against radial and longitudinal forces. The second end 144 of the support 140 includes a second end surface 145 that can be planar, rounded, pointed, or any configuration suitable for engaging with and embedding into the host bone tissue 3 (see FIGS. 1, 2, 39-41, 43A and 43B). This engaging and embedding, as previously discussed, is accomplished in situ because the force F acting along or parallel to the support axis X that is exerted during placement of the medical implant assembly 100 and when an individual stands up this acts to compress the tapered end(s) of the support 140 in order to provide a more secure connection of the support 140 to the body 110 and to the host bone tissue 3 (see FIGS. 1, 2, 39-41, 43A and 43B). The compression forces the first end 142 into a secure friction fit within a corresponding bore 113. This strong connection between the support 140 and the body 110 inhibits abrasion between the body 110 and the support 140 and further inhibits loosening of the connection over time. In addition, the support 140 may be textured or may comprise a plurality of pores, other surface features, or coatings to promote and/or allow bone ingrowth and/or ongrowth in order to more permanently secure the medical implant assembly 100 during its lifetime.

Another embodiment of a support 240 is shown in FIG. 13, which is defined by an elongate body having a tapered first end 242 comprising a body engagement portion 241 and an opposing second end 244 having a host tissue engagement portion 243. The body engagement portion 241 according to this embodiment includes a first frustoconical portion 246 extending from the first end 242 that outwardly tapers to an intermediate or second frustoconical portion 256, the latter portion further outwardly tapering to a shoulder 258. The host tissue engagement portion 243 is defined by a cylindrical or tubular portion 248 having a constant diameter. In the embodiment shown, the cylindrical or tubular portion 248 is separated from the second frustoconical portion 256 by the shoulder 258, which provides a positive mechanical stop for the support 240. More specifically and in cases where the host bone tissue is exceptionally weak, the shoulder 258 inhibits over insertion or over penetration of the support 240 into the host bone tissue 3 (see FIGS. 1, 2, 39-41, 43A and 43B), which would decrease the stability of the body 110. This decreased stability could cause a premature failure of the overall medical implant assembly 100 and the prosthetic hip 1 (see FIG. 1).

Another embodiment of a support 340 is shown in FIG. 14 and is defined by an elongate member that includes a tapered first end 342 having a body engagement portion 341, which is similar to the first frustoconical section 246, FIG. 13, of the support 240, FIG. 13. An opposing second end 344 includes a host tissue engagement portion 343 having a plurality of surface features 348, such as external threads, to aid in anchoring the second end 344 of the support 340 to the host bone tissue 3 (see FIGS. 1, 2, 39-41, 43A and 43B). In this embodiment, the support 340 is placed in the host bone tissue 3 (see FIGS. 1, 2, 39-41, 43A and 43B) after preparation of a pilot hole, and is attached to the body 110 during insertion rather than pre-assembled as is done for the other previously described supports 140, 240.

Other embodiments of the supports, such as 140, 240, 340 are envisioned that comprise at least some or all of the features discussed. For example, a multitude of shapes, diameters and lengths can be selected for the supports, such as 140, 240, 340 based on the surgeon's preference, the location and quality of host bone, as well as other factors. The designed features of the supports 140, 240, 340 enable stable support of the body 110 of the implant assembly without being substantially directly opposed to or in contact with the host bone tissue 3 (see FIGS. 1, 2, 39-41, 43A and 43B). This stable support is accomplished because the supports 140, 240, 340 can withstand both forces that compress the at least one tapered end, as well as axial forces encountered in any of a 360 degree direction. Furthermore, the ability of the supports 140, 240, 340, the fasteners (not shown), and the body 110 to promote and/or allow bone ingrowth and/or ongrowth increases the chances of long-term fixation and success of the medical implant assembly 200. The area of intended bone ingrowth or ongrowth to the supports may be modified and not include the entirety of the bone tissue apposition portions (such as isolated pads of features designed for bone ingrowth or ongrowth).

Figure 16:
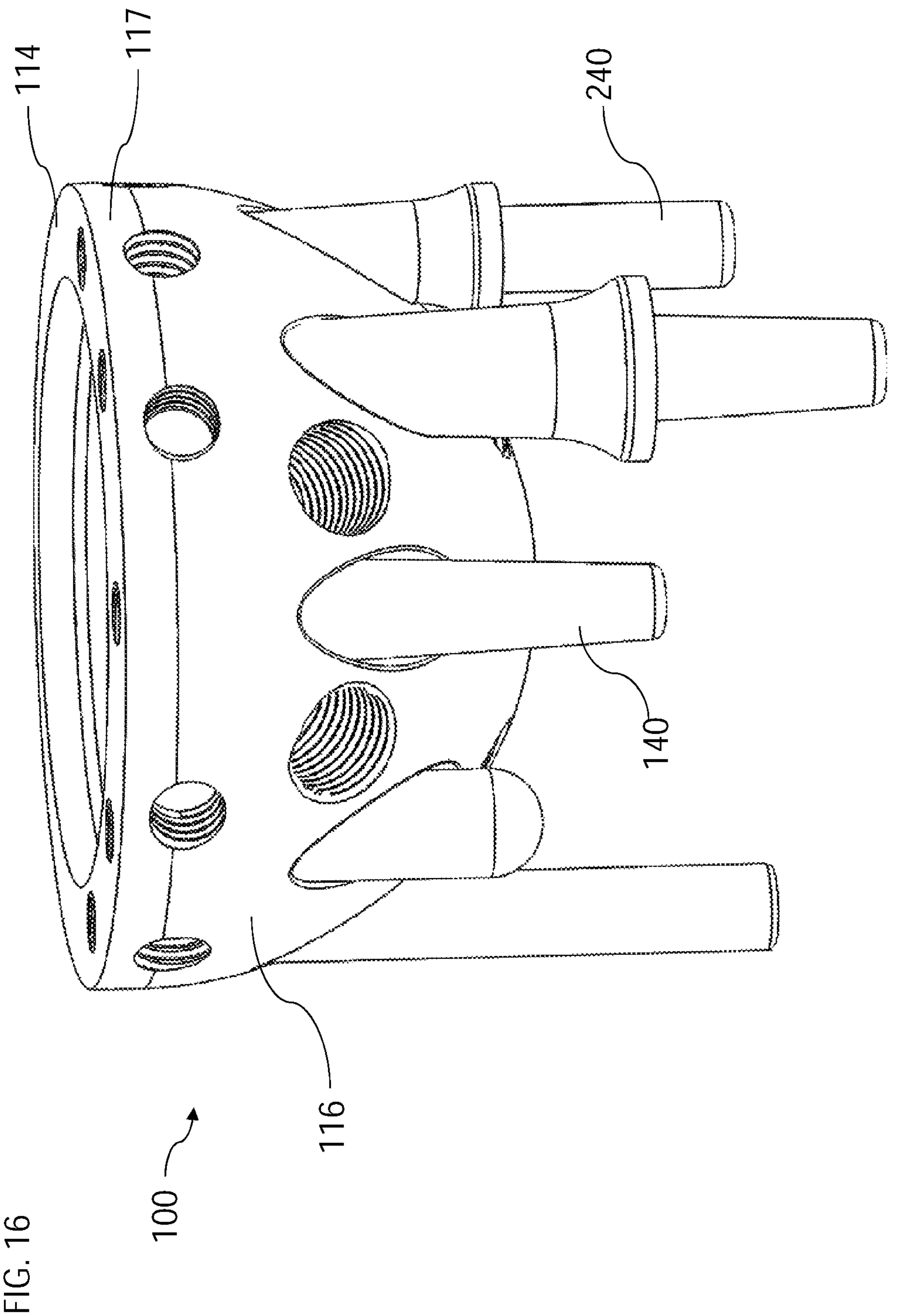
FIG. 16 illustrates a side perspective view of the embodiment of the medical implant assembly of FIG. 15.
Figure 17:
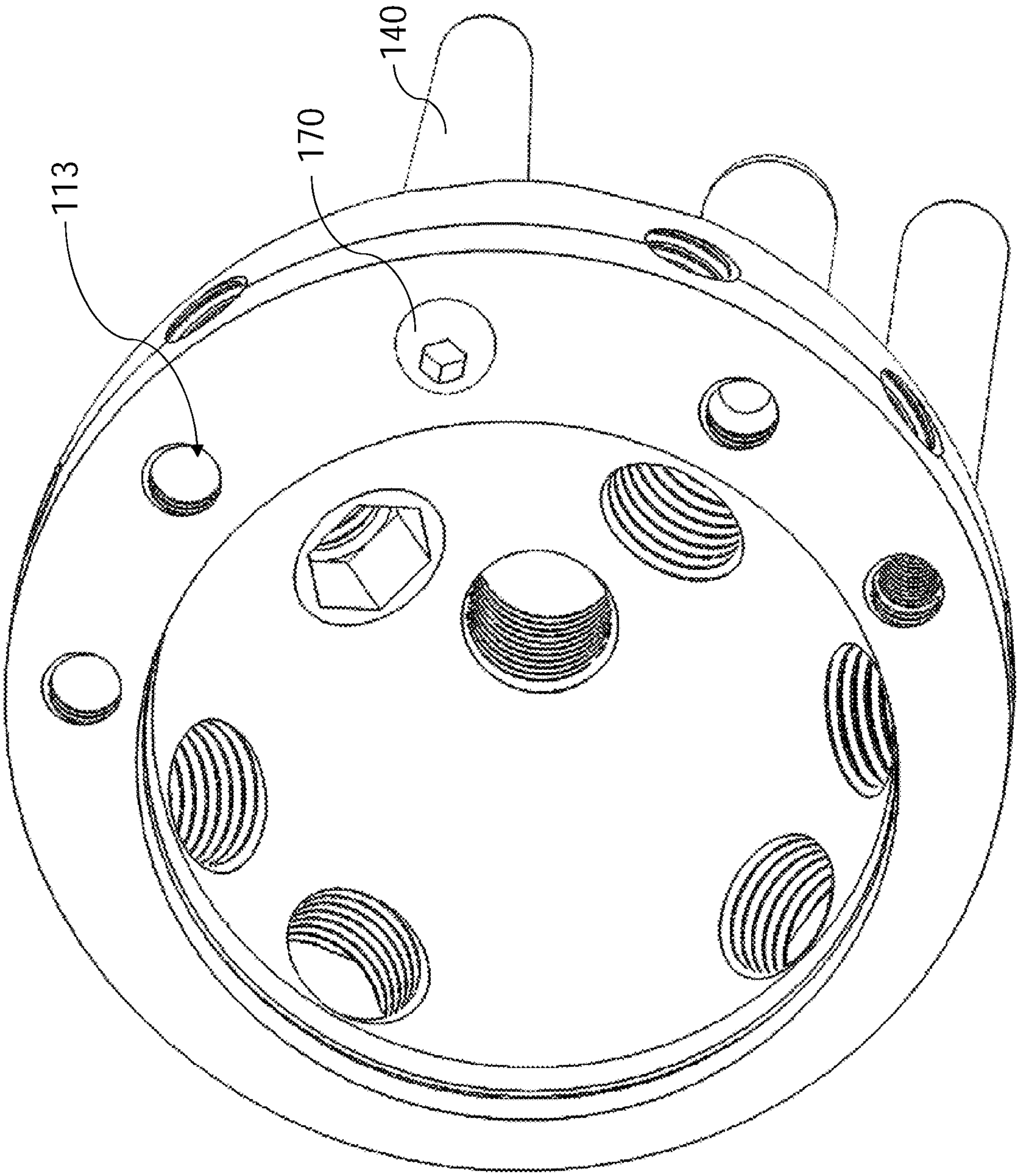
FIG. 17 illustrates a top perspective view of an embodiment of an assembled hip implant assembly of FIGS. 15 and 16.

FIGS. 15-17 illustrate an embodiment of an implant assembly 100 with the body 110 having a plurality of different mounted supports 140, 240 and also including a number of other support designs that have not been previously described. One exemplary method of coupling any of the supports 140, 240, 340 will now be discussed with reference to FIGS. 12 and 18-20 and one of the previously described support designs, namely a support 140. According to this method, the first end 142 of the support 140 is inserted into the bore 113 of the body 110 until the body engagement portion 141 of the support 140 creates a friction-fit with the body 110 and/or until the support 140 cannot be inserted any further. As can be seen, the first end 113*a* of the bore 113 (the end closest to the rim 114) has a diameter that is smaller than the opposing second end 113*b* of the bore 113 so as to create a taper. According to this embodiment and as shown in FIG. 18, a fastener 170, such as a screw, is then inserted through the bore opening 113 in the body 110 and into the cavity 154 (surrounded by the annular inner surface 156) of the support 140. The fastener 170 may be driven to the base 155 (FIGS. 18 and 19) of the cavity 154 or may only partially occupy the cavity 154, which is preferred so as to maintain a compressive force rather than bottoming out in the cavity 154. The fastener 170, as shown, has a complementary external thread pattern to that of the annular inner surface 156 such that rotation of the fastener 170 acts to advance the fastener 170 into the cavity 154 to further secure the support 140 to the body 110. In order to decouple the support 140 from the body 110, the fastener 170 can be backed out of the cavity 154 of the support 140. The support 140 may then be removed from the body 110 while understanding that there may be a friction fit of a substantial nature generated between the 2 frustoconical surfaces in contact.

Figure 20:
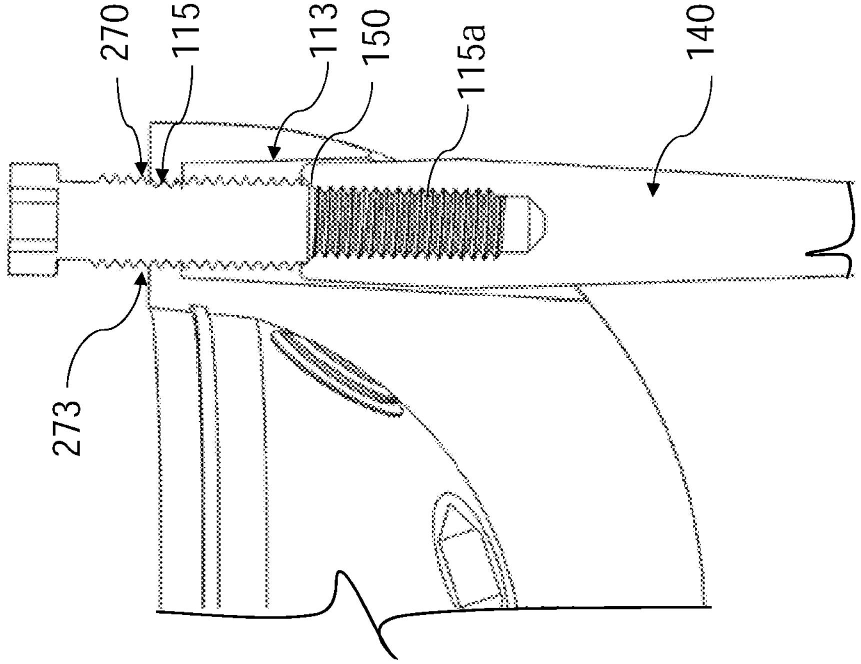
FIG. 20 illustrates a sectional side view of the embodiment of FIG. 19 with the distraction bolt engaged at a second position.

In another embodiment shown in FIGS. 19 and 20, the support 140 can be alternatively decoupled from the body 110 using a different fastener 270 (such as a larger screw) having a diameter (D1) external thread 273 that engages and is complementary to the internal threads 115*a* (FIGS. 15, 19, 20) of the inner surface 115 of the bore 113 of the body 110 but is large enough to not engage nor enter the diameter (D2) of the cavity 154 of the support 140, thus providing a decoupling force. The fastener 270 is inserted into the bore 113 and rotated to drive the fastener 270 to abut the first end surface 150 of the support 140. Continued driving of the fastener 270 acts to push the support 140 out of the bore 113 and decouple the fastener 270 from the body 110 of the medical implant assembly 100.

Figure 21B:
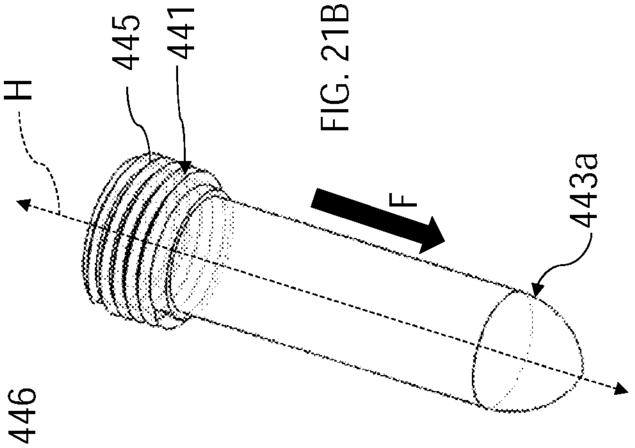
FIG. 21B illustrates a perspective side view of the support of FIG. 21A.
Figure 21A:
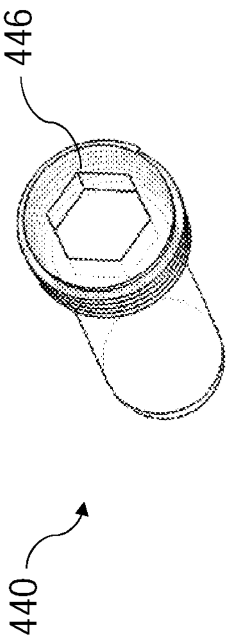
FIG. 21A illustrates a perspective top view of an embodiment of a support of the medical implant assembly.
Figure 21C:
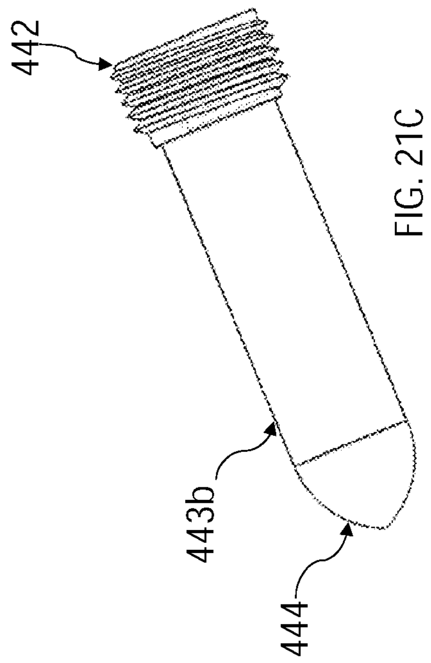
FIG. 21C illustrates a side view of the support of FIGS. 21A and 21B.

Additional embodiments of supports shown in FIGS. 21A-23C are configured to couple to the body 110 via the inner bores 126 (see FIG. 15). Referring specifically to FIGS. 21A-C, a support 440 is an elongate member that extends along a support axis H extending between a first end 442 and an opposing second end 444. The first end 442 includes a body engagement portion 441 and the second end 444 includes a host tissue engagement portions 443*a* and 443*b*. The body engagement portion 441 includes a body engagement interface 445, which may define a plurality of surface features such as a set of external threads. The first end 442 of the support 440 may further include a tool interface 446, such as a socket, that is structured to cooperate with a tool (not shown) to aid in coupling and decoupling of the support 440 to the body 110. The body engagement interface 445 is structured to interact with the body 110 to securely couple the first end 442 of the support 440 to the body 110. As shown, the secure coupling is achieved using complementary threaded surfaces which may be tapered or parallel.

The host tissue engagement portion 443 of the support 440 includes a rounded or tapered second end 444 that is structured to engage the host bone tissue 3 (see FIGS. 1, 2, 39-41, 43A and 43B) and develop a strong friction fit as a result of a force F acting in a direction along or substantially parallel to the support axis H. The host tissue engagement portion may be configured to promote and/or allow bone ingrowth or ongrowth on the entire surface on only on a portion of the host tissue engagement surface.

Figure 22A:
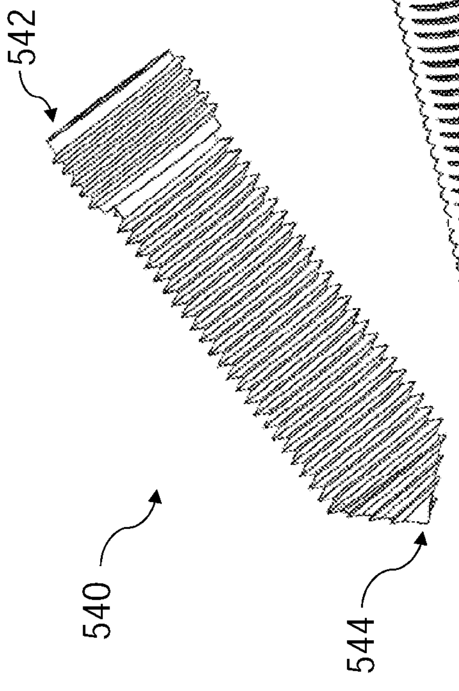
FIG. 22A illustrates a side view of another embodiment of a support of the medical implant assembly.
Figure 22B:
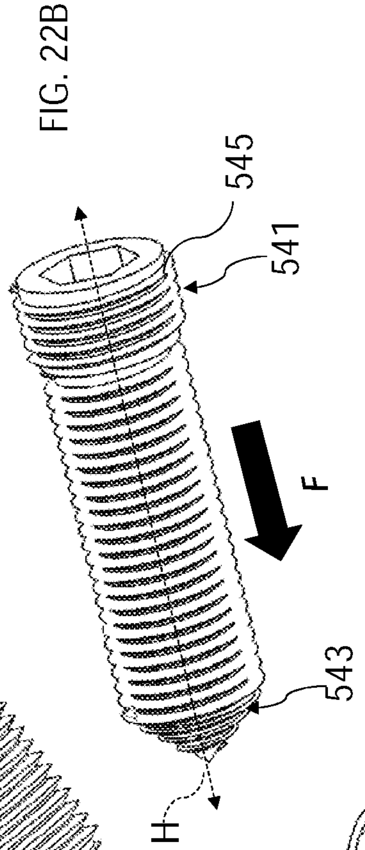
FIG. 22B illustrates a perspective side view of the support of FIG. 22A.
Figure 22C:
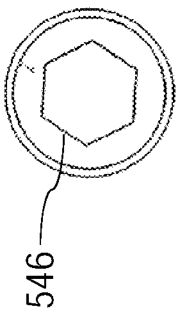
FIG. 22C illustrate a top view of the support of FIGS. 22A and 22B.

Turning to FIGS. 22A-C, another embodiment of a support 540 is shown that extends along a support axis H between a first end 542 and an opposing second end 544 As in the prior embodiment, the support 540 is defined by an elongate member having a substantially cylindrical cross section in which the first end 542 of the support 540 includes a body engagement portion 541 and the second end 544 includes a host tissue engagement portion 543. According to this embodiment, the body engagement portion 541 has a body engagement interface 545, which may define a plurality of surface features, such as external threads that are disposed over the entire body engagement portion 541, as well as at least a portion of the host tissue engagement portion 543. The first end 542 of the support 540 may further include a tool interface 546, such as a socket, that is structured to cooperate with a tool (not shown) to aid in coupling an decoupling of the support 540 to the body 110. The body engagement interface 545 is structured to interact with the body 110 to securely couple the first end 542 of the support 540 to the body 110. As shown, the secure coupling is achieved using complementary threaded surfaces.

The host tissue engagement portion 543 of the support 540 includes a rounded or tapered second end 544 that is structured to engage the host tissue 3 (see FIGS. 1, 2, 39-41, 43A and 43B) and develop a strong friction fit as a result of a force F acting in a direction along or substantially parallel to the support axis H. In this embodiment, the entire exterior surface of the support 540 includes a plurality of surface features, such as external threads, to further assist in forming a secure connection to the host bone tissue 3 (see FIGS. 1, 2, 39-41, 43A and 43B).

Figure 23B:
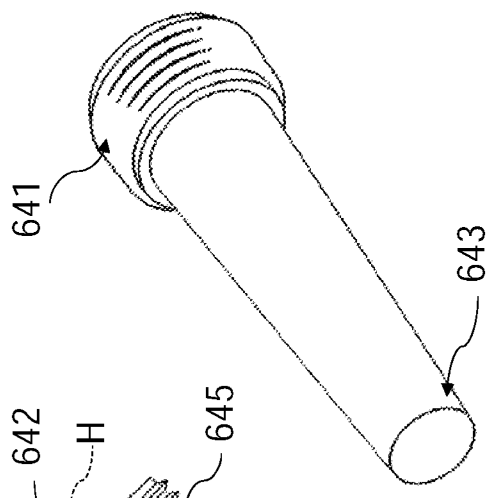
FIG. 23B illustrates a perspective bottom view of the support of FIG. 23A.
Figure 23C:
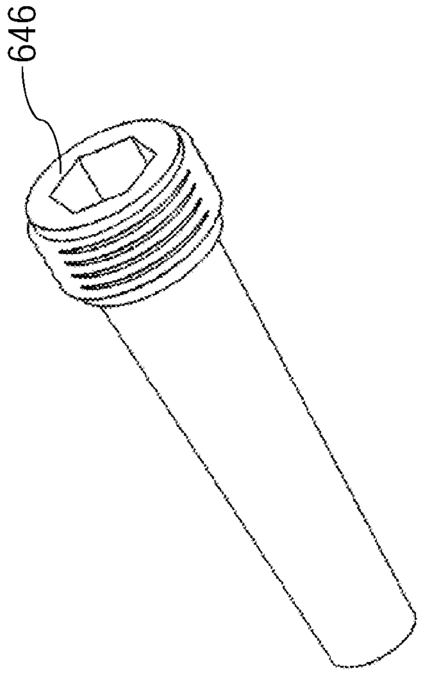
FIG. 23C illustrates a perspective top view of the embodiment of FIGS. 23A and 23B.
Figure 23A:
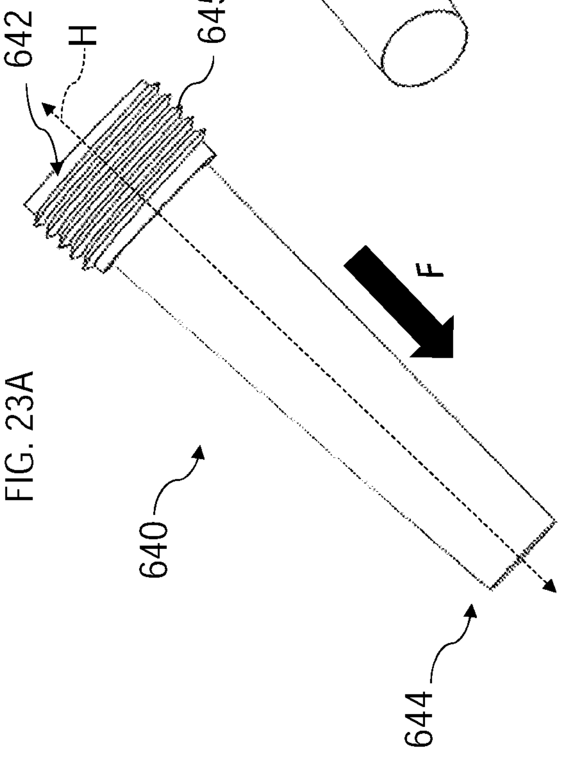
FIG. 23A illustrates a side view of another embodiment of a support of the medical implant assembly.

Referring now to FIGS. 23A-C, a support 640 made in accordance with another exemplary embodiment is shown. The support 640 is defined by an elongate member that extends along a support axis H extending between a first end 642 and an opposing second end 644. The first end 642 includes a body engagement portion 641 and the second end 644 includes a host tissue engagement portion 643 made with a configuration that outwardly tapers from the second end 644. The body engagement portion 641 has a body engagement interface 645, which may define a plurality of surface features such as, for example, a set of external threads. The first end 642 of the support 640 may further include a tool interface 646, such as a socket, that is structured to cooperate with a tool (not shown) to aid in coupling an decoupling of the support 640 to the body 110. The body engagement interface 645 is structured to interact with the body 110 in order to securely couple the first end 642 of the support 640 to the body 110. As shown, secure coupling is achieved using complementary threaded surfaces. According to this embodiment, the host tissue engagement portion 643 of the support 640 includes a rounded or tapered second end 644 that is structured to engage the host bone tissue 3 (see FIGS. 1, 2, 39-41, 43A and 43B) and develop a strong friction fit as a result of a force F acting in a direction along or substantially parallel to the support axis H.

Figure 24:
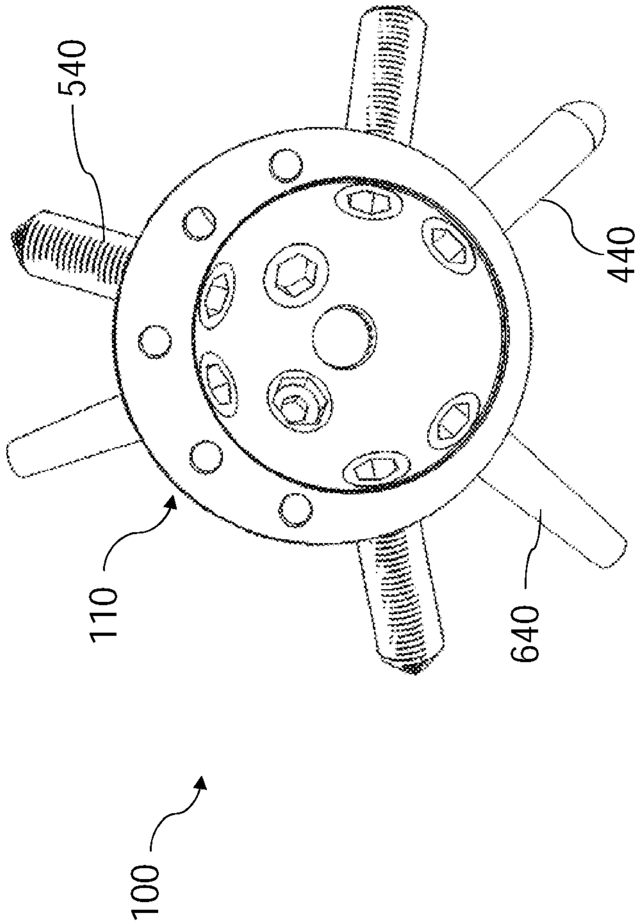
FIG. 24 illustrates a top view of an embodiment of the body of the medical implant assembly having a plurality of different embodiments of supports coupled to the body.
Figure 25:
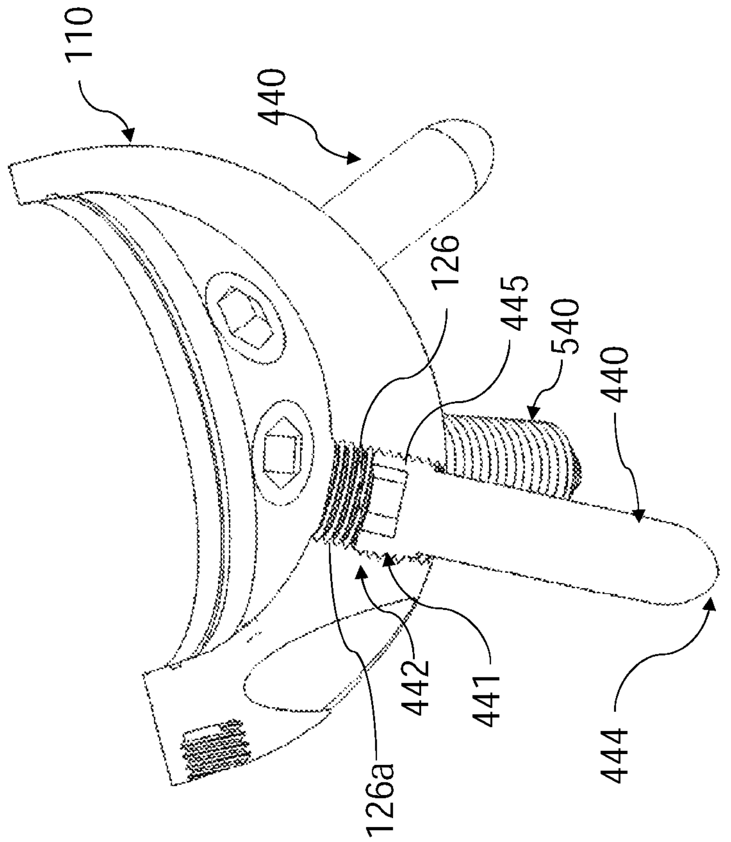
FIG. 25 illustrates a side sectional view of the embodiment of the support of FIGS. 21A-C coupled to an embodiment of the body of the medical implant assembly.
Figures 26A, 26B:
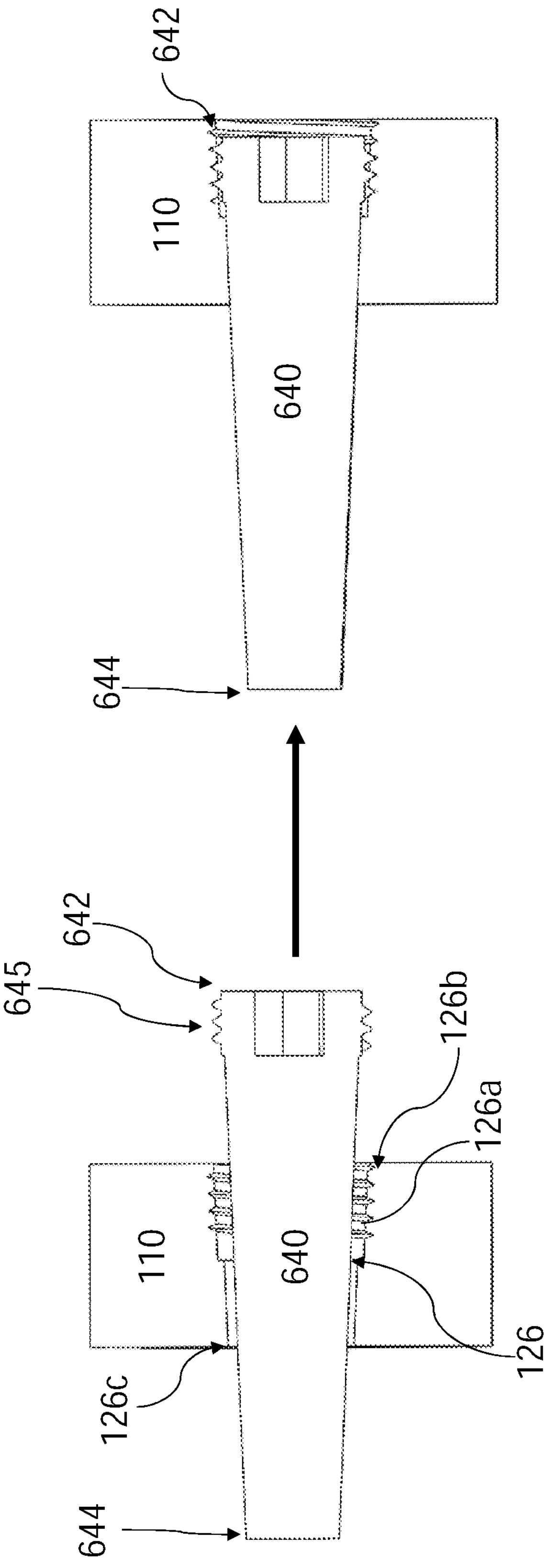
FIG. 26A illustrates a sectional view of the embodiment of the support from FIGS. 23A-C and a portion of a body of the medical implant assembly showing the support at a stage of being coupled to the body.
FIG. 26B illustrates a sectional view of the embodiment of FIG. 26A at another stage of being coupled to the body.
Figure 28B:
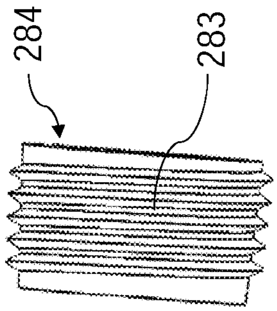
FIG. 28B illustrates a side view of the adapter of FIG. 28A.
Figure 28D:
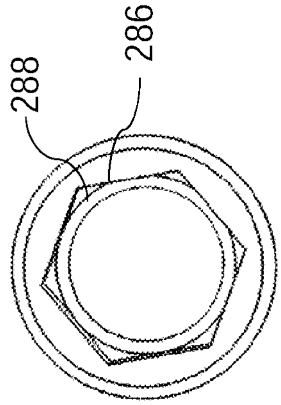
FIG. 28D illustrates a top view of the adapter of FIGS. 28A-C.
Figure 28A:
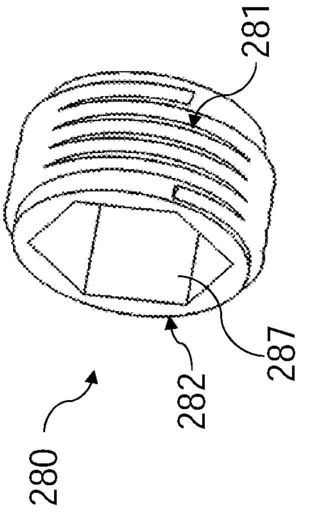
FIG. 28A illustrates a perspective side view of an embodiment of an adapter configured to be coupled to the body of the medical implant assembly.
Figure 28C:
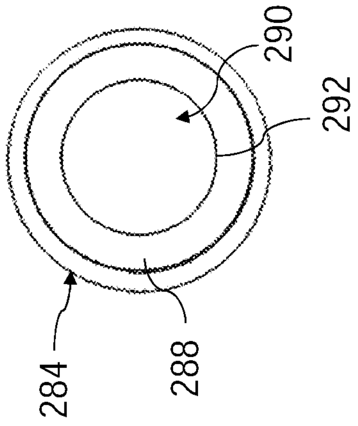
FIG. 28C illustrates a bottom view of the adapter of FIGS. 28A and 28B.

FIGS. 24 and 25 illustrates an example of a body 110 of the medical implant assembly 100 having various supports 440, 540, 640 coupled to the body 110 via the inner openings 126. By way of example, the coupling of one of the supports 640 shown in FIGS. 23A-23C will be described with reference to FIGS. 26A and 26B. The support 640 may be coupled to the body 110 by inserting the first end 642 with the body engagement portion 641 into the inner opening 126 of the body 110. According to this embodiment, the inner opening is tapered such that the diameter at the first end 126*b* defined by the interior surface 124 is larger than the diameter at the opposing second end 126*c* defined by the exterior surface 116. The body engagement interface 645 of the body engagement portion 641 interacts with surface features 126*a* in the inner opening 126, such as internal threads, which may be parallel or tapered. Rotation of the support 640 about its center axis acts to couple the support 640 to the body 110 and, in some embodiments, adjust the position of the support 640 relative to the body 110. In some embodiments it is also possible to insert the second end 444, 544, 644 of the support 440, 540, 640 through the inner opening 126. The first end 442, 542, 642 with the body engagement portion 441, 541, 641 then couples to the body 110 in a similar manner as previously described.

It is also possible to further attach the body 110 to the host bone tissue 3 (see FIGS. 1, 2, 39-41, 43A and 43B) using a fastener 180, such as a compression bone screw shown in FIGS. 27A-C. Such compression screws are known in the art and have been used for decades in various medical procedures. Each fastener 180 generally includes a first end 182 and an opposing second end 184. The first end 182 includes an engagement interface 181 that has a tapered surface 183 extending to the shank of the compression screw and in which the opposite second end 184 includes an end point 186 and a plurality of threads 187 that securely engage with the host bone tissue 3 (see FIGS. 1, 2, 39-41, 43A and 43B). One or more fasteners 180 can be used in addition to any of the supports previously disclosed in order to secure the body 110 to the host bone tissue 3 (see FIGS. 1, 2, 39-41, 43A and 43B).

Referring to FIGS. 28A-30, the fastener 180, such as a compression bone screw, is shown being used along with an adapter 280 to provide one or more additional options for the surgeon to fix the body 110 to the host bone tissue 3 (see FIGS. 1, 2, 39-41, 43A and 43B). FIGS. 28A-D show an exemplary embodiment of an adapter 280. The adapter 280 is defined by an elongate body having a generally cylindrical shape including an outer surface 283 extending between a first end 282 and an opposing second end 284. The outer surface 283 may include a plurality of surface features 281, such as a set of external threads. The first end 282 defines a first end opening 286 that extends into an axial through cavity 290 bounded by a socket 287 and that is structured to at least partially accept a tool (not shown) to aid in coupling the adapter 280 to an inner opening 126 of the body 110. The second end 284 of the adapter 280 has an annular shoulder 288 that surrounds a second end opening 292 extending to the axial through cavity 290.

Figure 29A:
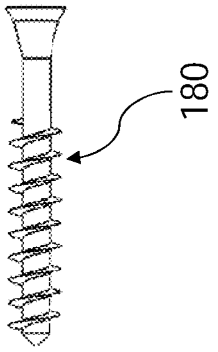
FIG. 29A illustrates a side view of an embodiment of a compression bone screw of FIGS. 27A-C.
Figure 29B:
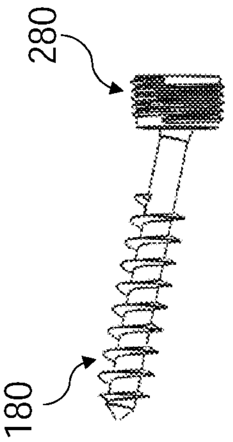
FIG. 29B illustrates a side view of the compression bone screw of FIG. 29A inserted into the adapter of FIGS. 28A-D.
Figure 29C:
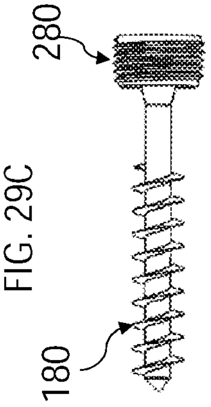
FIG. 29C illustrates a side view of the compression bone screw of FIG. 29A inserted into the adapter of FIGS. 28A-D.
Figure 29D:
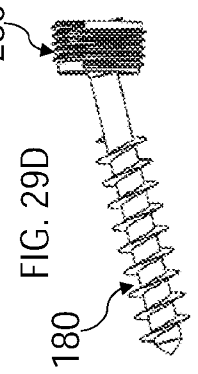
FIG. 29D illustrates a side view of the compression bone screw of FIG. 29A inserted into the adapter of FIGS. 28A-D.
Figure 30:
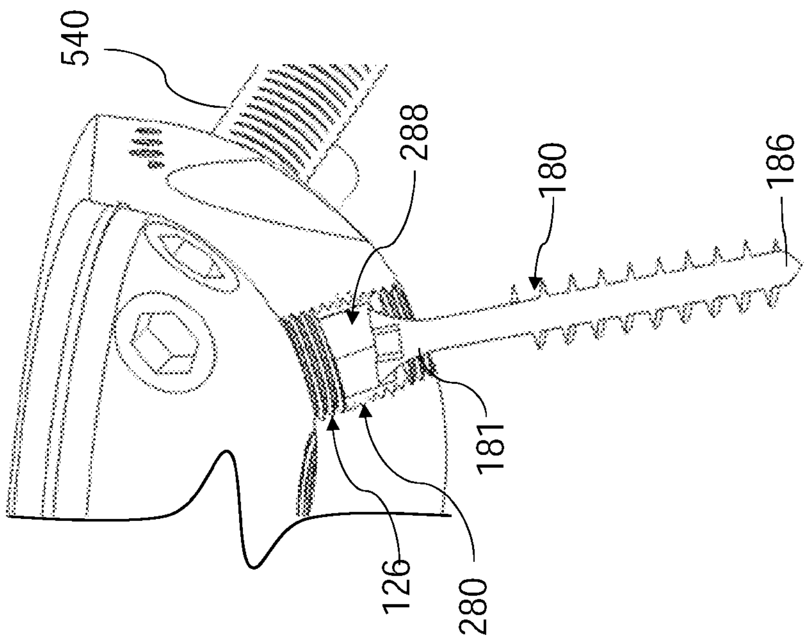
FIG. 30 illustrates a sectional side view of the adapter of FIGS. 28A-D and bone screw of FIG. 29A coupled through an inner opening to an embodiment of the body of the medical implant assembly.
Figure 31:
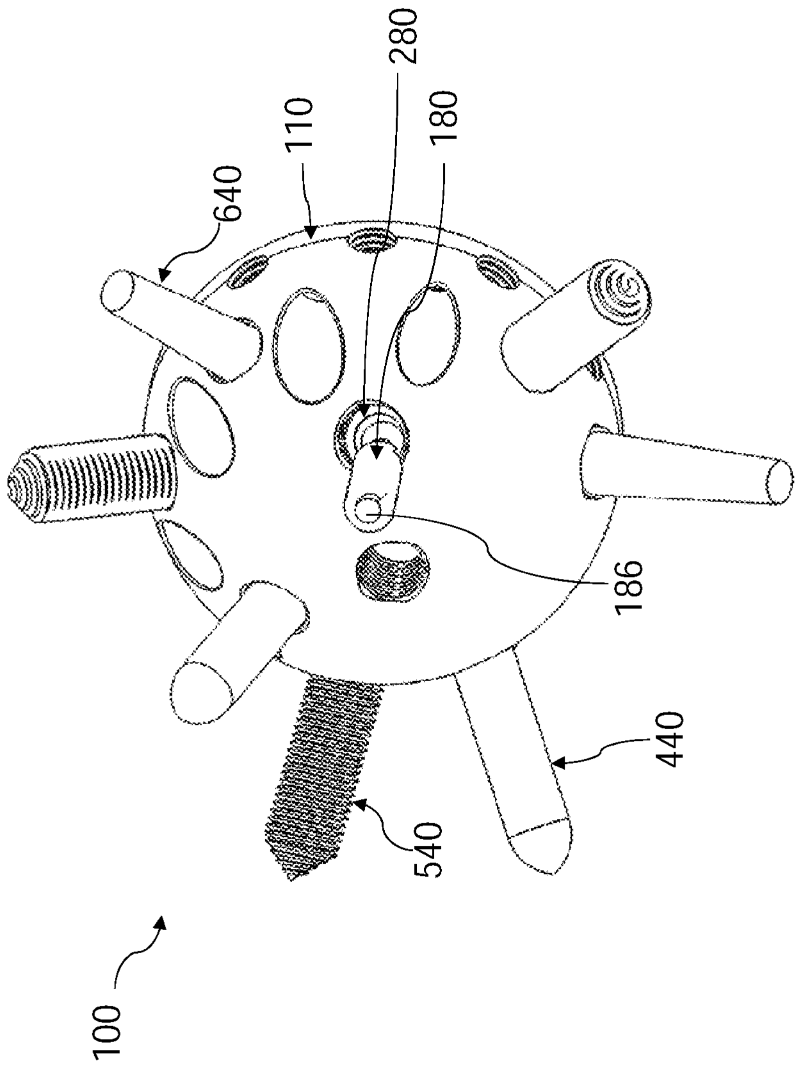
FIG. 31 illustrates a bottom perspective view of the body of the medical implant assembly with several support members attached through internal openings.

FIG. 29A shows the fastener 180, such as a compression screw, from FIGS. 27A-C alone, and FIGS. 29B-D show the fastener 180 in combination with the adapter 280 of FIG. 28A-D as mated. FIGS. 30 and 31 show the fastener 180 in combination with the adapter 280 as connected to the body 110 of the medical implant assembly 100. As can be seen and when the fastener 180 is inserted through the cavity 290 of the adapter 280, the fastener 180 is able to pivot or tilt relative to the adapter 280 prior to engagement with the host bone tissue 3 (see FIGS. 1, 2, 39-41, 43A and 43B). As shown in FIG. 30, the adapter 280 is coupled to the body 110 via an inner opening 126. The second end 184 of the fastener 180 is inserted through the first opening 286 and then the second opening 292 of the adapter 280. The annular shoulder 288 catches the engagement interface 181 of the fastener 180 and prevents the fastener 180 from passing through the second opening 292. However, the fastener 180 is able to swivel relative to the adapter 280 and the body 110, which provides the surgeon a degree of flexibility when positioning and securing the body 110 of the medical implant assembly 100 to the host bone tissue 3 (see FIGS. 1, 2, 39-41, 43A and 43B).

FIGS. 32-34C illustrate additional exemplary embodiments of the body 110 with a variety of different supports/fasteners 180, 240, 440, 540, 640 coupled to the body 110 and extending along many different planes. As can be seen, the medical implant assembly 100 is capable of being secured to and against host bone tissue 3 (see FIGS. 1, 2, 39-41, 43A and 43B) from many different directions using a variety of different types of supports depending on the needs of a specific surgical case. In this manner, the medical implant assembly 100 can be easily and inexpensively customized for each patient's unique condition in order to provide axial and radial stability.

Figures 35A, 35B, 35C, 35D:
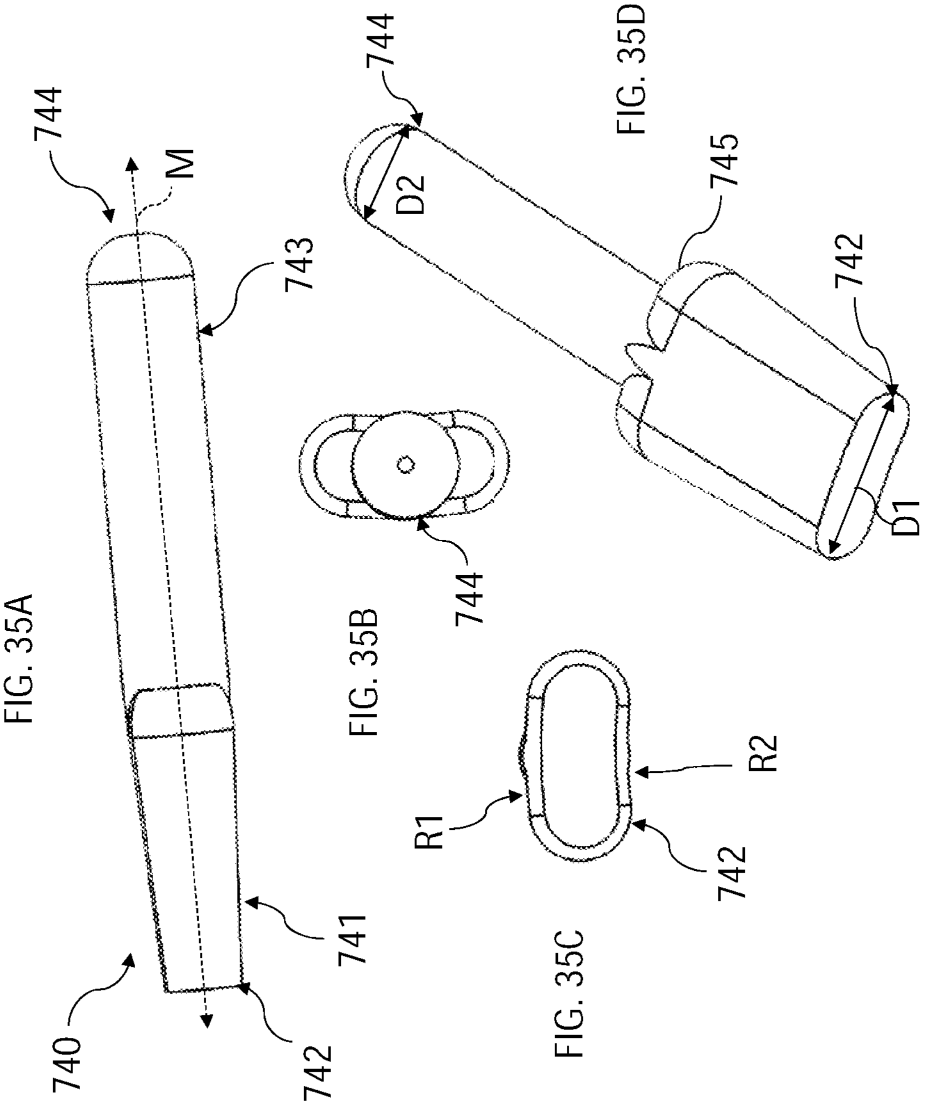
FIG. 35A illustrates side view of another embodiment of a support.
FIG. 35B illustrates a bottom view of the support of FIG. 35A.
FIG. 35C illustrates a top view of the support of FIGS. 35A and 35B.
FIG. 35D illustrates a side perspective view of the support of FIGS. 35A-C.

The embodiments of supports previously discussed all comprise a circular cross-section along a support axis. It will be understood, however, that other variants are possible. For example, FIGS. 35A-37E illustrate other embodiments of supports 740, 840, 940 that include an ovular, elliptical, discorectangular or other non-polygonal cross-section at one end of the support and a circular cross-section at the other opposite end. These embodiments may include several of the same structural features as described in previous embodiments that are configured to function in a similar manner. For example, support 740, which is illustrated in FIGS. 35A-D, is an elongate member that extends along a support axis M between a first end 742 and an opposing second end 744. Similar to previous designs discussed, the first end 742 includes a body engagement portion 741 and the second end 744 includes a host tissue engagement portion 743. As shown in FIGS. 35C and 35D, the body engagement portion 741 is defined by a cross section that is generally similar to a geometric stadium or discorectangle with a first diameter D1 along the major dimension of the cross section. However, the longer edges are defined by lines that have radii R1 and R2 which may be equal or dissimilar. The host tissue engagement portion 743 includes a cylindrical cross section, shown in FIGS. 35A, B and D, which is mainly constant with the exception of a rounded end, the cylindrical cross section having a second narrower diameter D2 such that D1 is greater than D2. The body engagement portion 741 transitions to the host tissue engagement portion 743 at an intermediate portion 745. As shown in FIG. 35D, the intermediate portion 745 is defined by a shoulder that may be configured to act as a mechanical stop or as a transition to the host tissue engagement portion 743.

Figures 36A, 36B, 36C, 36D, 36E:
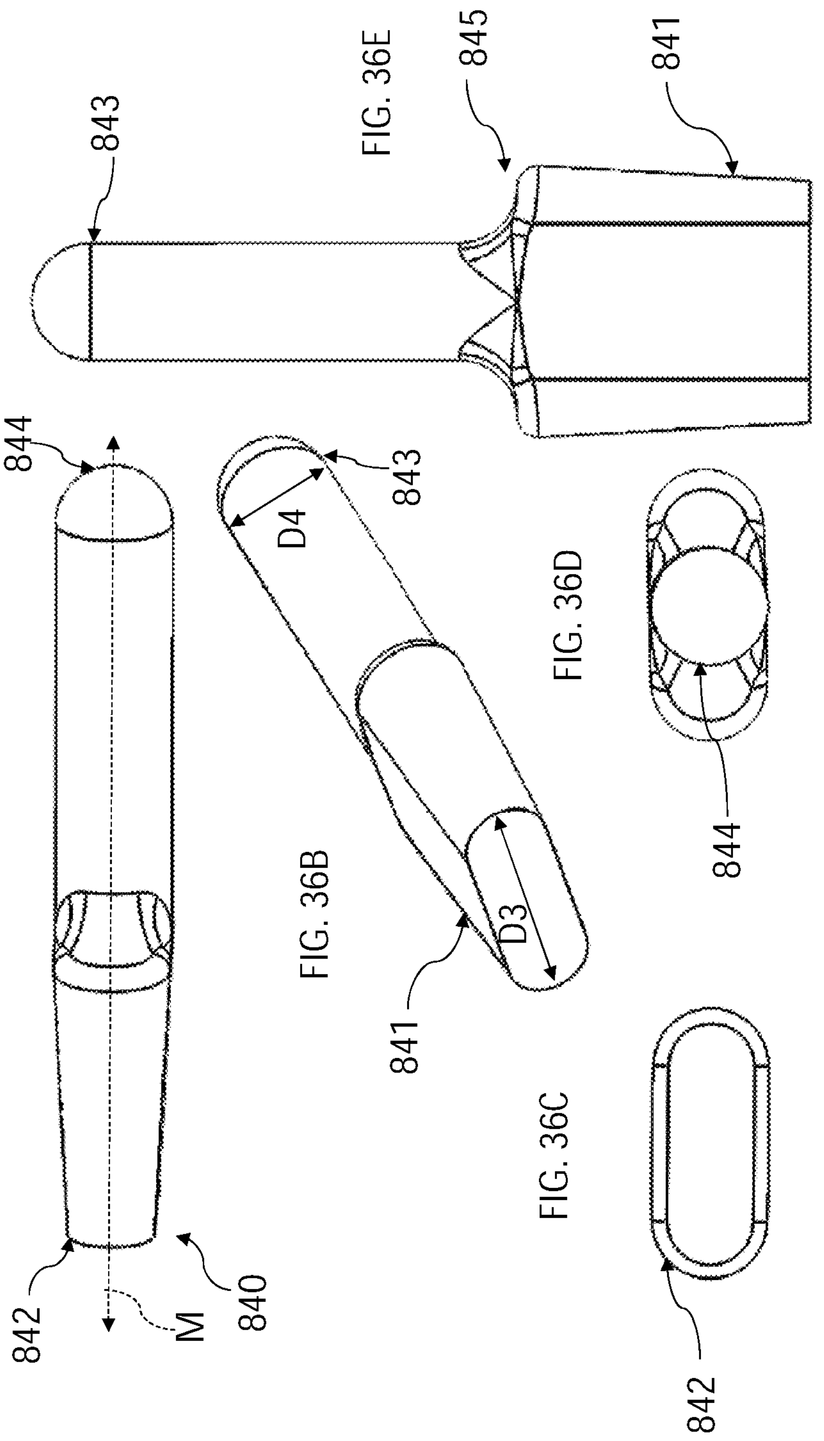
FIG. 36A illustrates a side view of another embodiment of a support made in accordance with aspects of the invention.
FIG. 36B illustrates a top perspective view of the support of FIG. 36A.
FIG. 36C illustrates a top view of the support of FIGS. 36A and 36B.
FIG. 36D illustrates a bottom view of the support of FIGS. 36A-C.
FIG. 36E illustrates a front view of the embodiments of FIGS. 36A-D.

Another exemplary support 840 is shown in FIGS. 36A-E. The support 840 is also defined by an elongate member that extends along a support axis M extending between a first end 842 and a second opposing end 844. As in the prior described version, the first end 842 includes a body engagement portion 841 and the opposing second end 844 includes a host tissue engagement portion 843. As shown in FIGS. 36B and 36C, the body engagement portion 841 is defined by a geometric stadium or discorectangle cross section with the major dimension of the ellipse defining a first diameter D3 and the host tissue engagement portion 843 is a cylindrical portion having a constant cross section with the exception of a rounded end; see FIGS. 36 A, D and E. The cylindrical portion defines a second diameter D4 such that D3 is greater than D4. The body engagement portion 841 transitions to the host tissue engagement portion 843 at an intermediate portion 845. As shown in FIG. 36E, the intermediate portion 845 is defined by a shoulder having a sloped transition with the host tissue engagement portion 843.

Figures 37A, 37B, 37C, 37D, 37E:
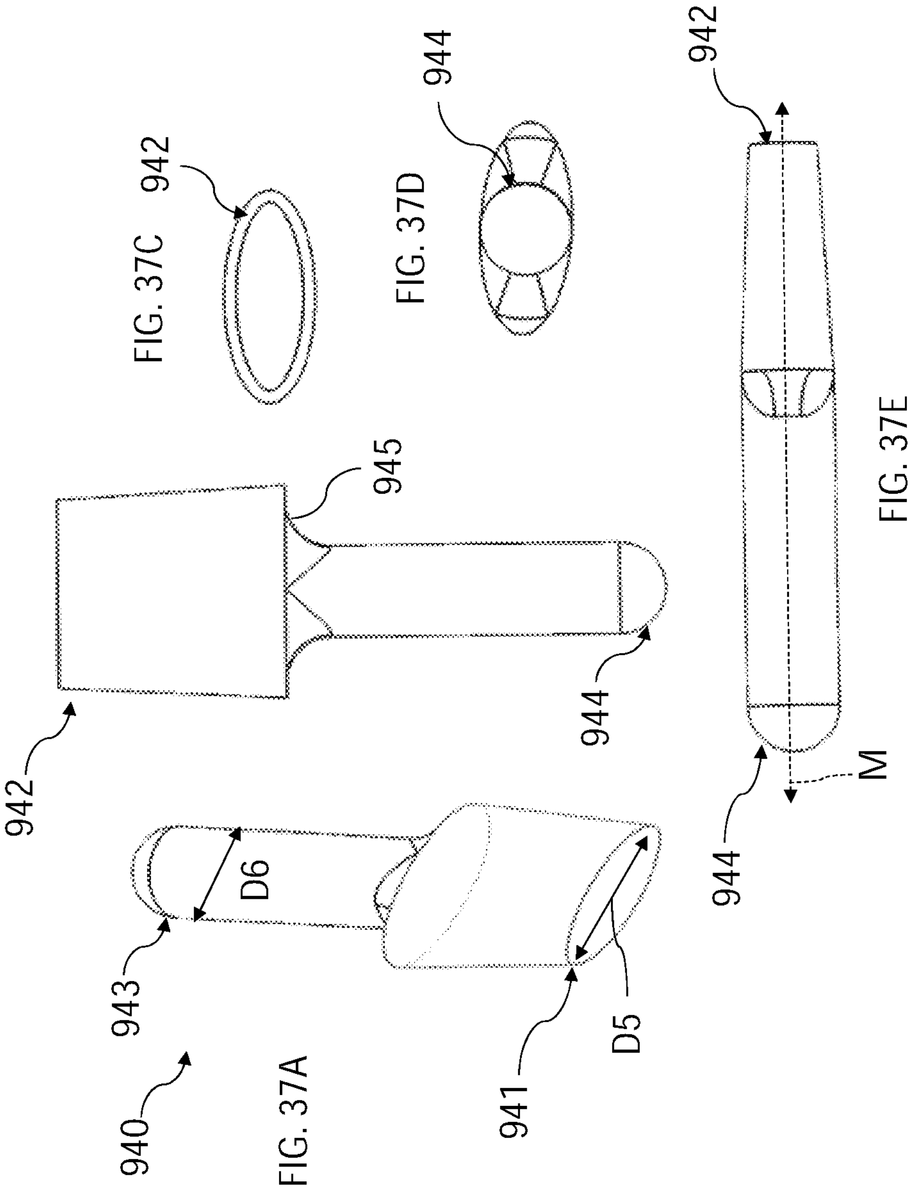
FIG. 37A illustrates a side perspective view of another embodiment of a support made in accordance with aspects of the invention.
FIG. 37B illustrates a front view of the support of FIG. 37A.
FIG. 37C illustrates a top view of the support of FIGS. 37A and 37B.
FIG. 37D illustrates a bottom view of the support of FIGS. 37A-C.
FIG. 37E illustrates a side view of the support of FIGS. 37A-D.

Referring to FIGS. 37A-E, another exemplary support 940 is also an elongate member that extends along a support axis M from a first end 942 to an opposing second end 944. As in the prior described versions, the first end 942 of the support 940 includes a body engagement portion 941 and the second end 944 includes a host tissue engagement portion 943. As shown, the body engagement portion 941 is defined by an elliptical cross section having a major dimension that defines a first diameter D5 and the host tissue engagement portion 943, which is a cylindrical portion having a rounded end is defined by a second diameter D6 such that D5 is greater than D6. The body engagement portion 941 transitions to the host tissue engagement portion 943 at an intermediate portion 945. As shown in FIG. 37E, the intermediate portion 845 is defined by a shoulder, which can be sloped.

Figure 38:
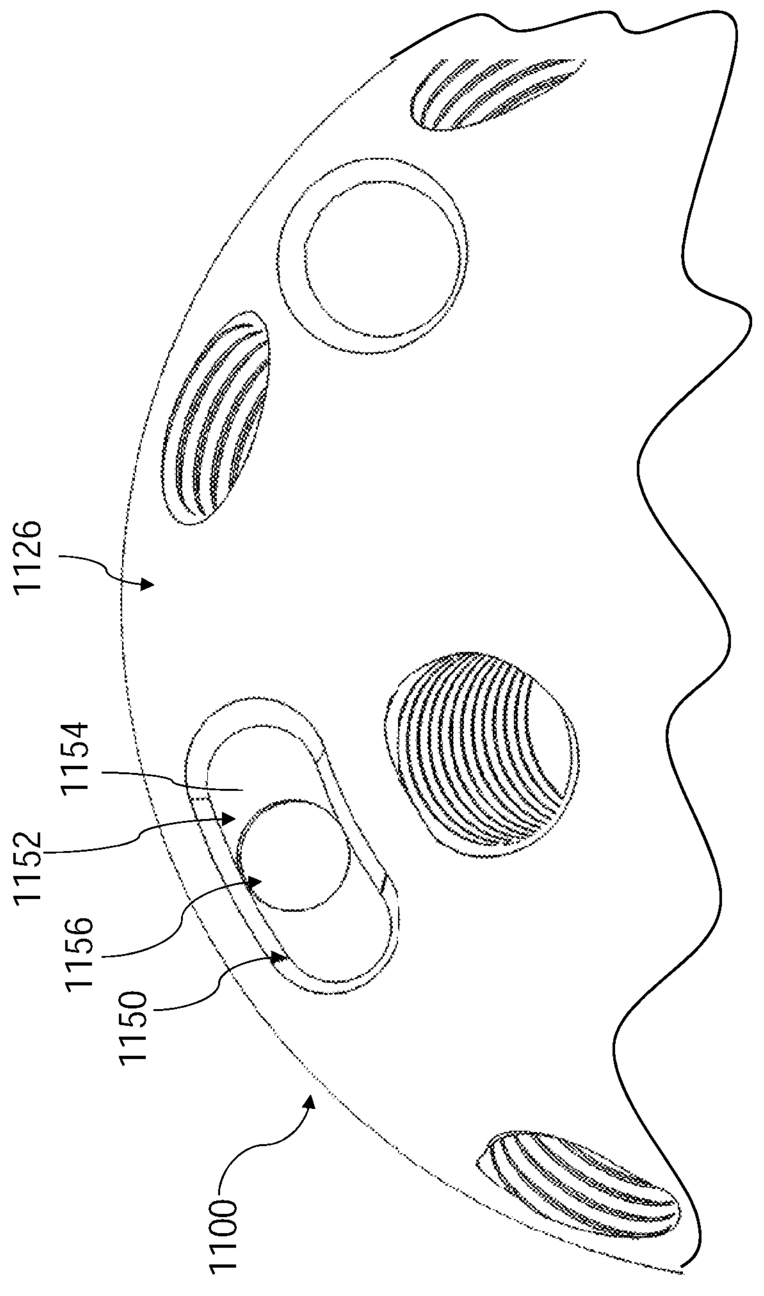
FIG. 38 illustrates a partial bottom view of another embodiment of a body of the hip implant assembly structured to couple with embodiments of the support from FIGS. 35A-D.

FIG. 38 illustrates an embodiment of a body 1100 that is structurally configured to accept the support 740 previously discussed in FIGS. 35A-37E, by way of example. As shown, the body 1100 includes a support engagement interface 1150 formed in the outer convex surface 1126 that is structured to interact or engage with the body engagement portion 743, 843, 943 of the supports 740, 840, 940. In the embodiment shown, the support engagement interface 1150 defines a cavity 1152 formed in the outer convex surface, having a recessed cavity base 1154. An axial bore 1156 is provided in the recessed cavity base 1154 that extends through entirely through the body 1110 and is dimensioned to accept a fastener (not shown), such as those described in previously described embodiments, to further secure one of more of the supports 740 to the body 1110.

Figure 39:
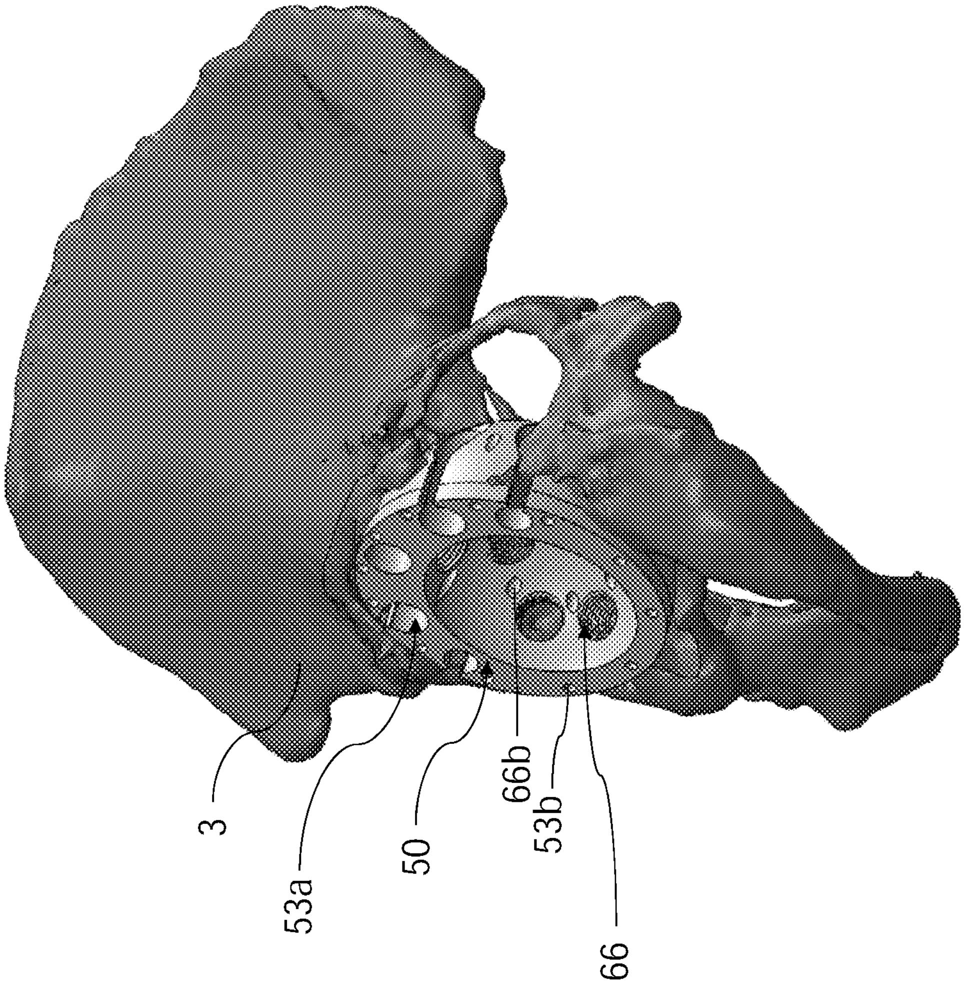
FIG. 39 illustrates a perspective view of an embodiment of the positioning device of the medical implant system positioned relative to bone tissue in the pelvic area.
Figure 40:
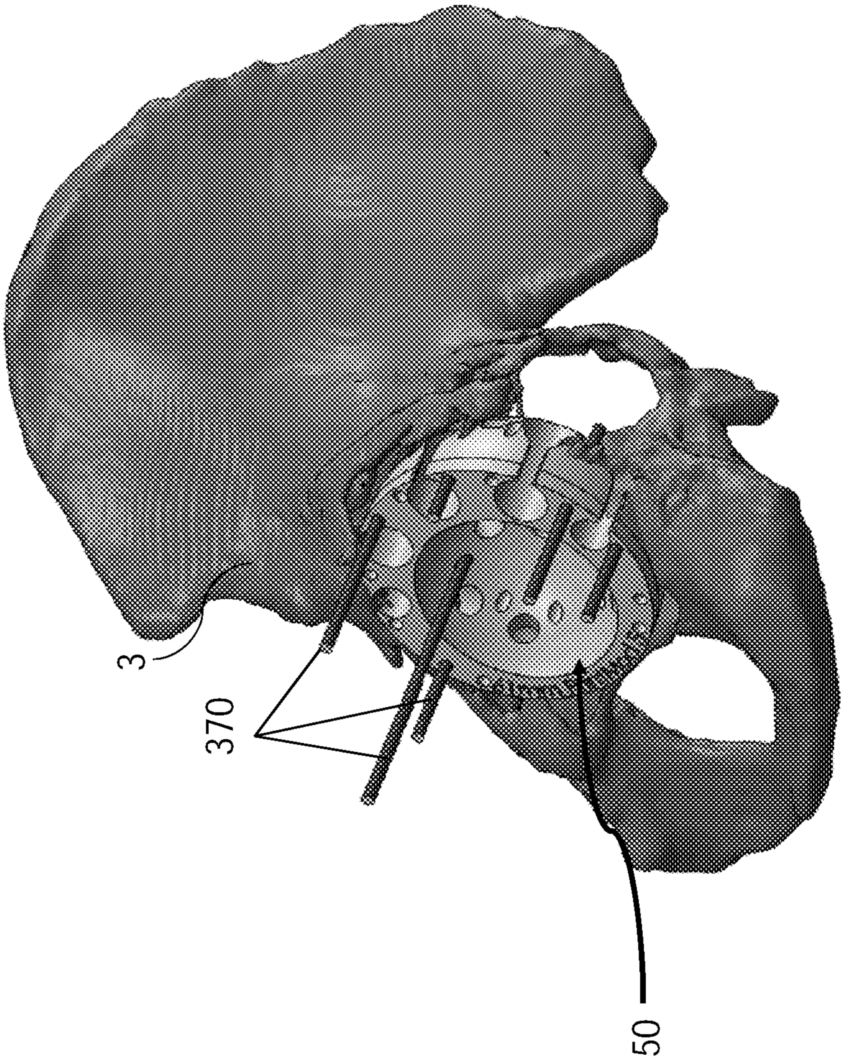
FIG. 40 illustrates a perspective view of the positioning device of FIG. 39 tacked in place relative to the bone tissue using a plurality of pins.
Figure 41:
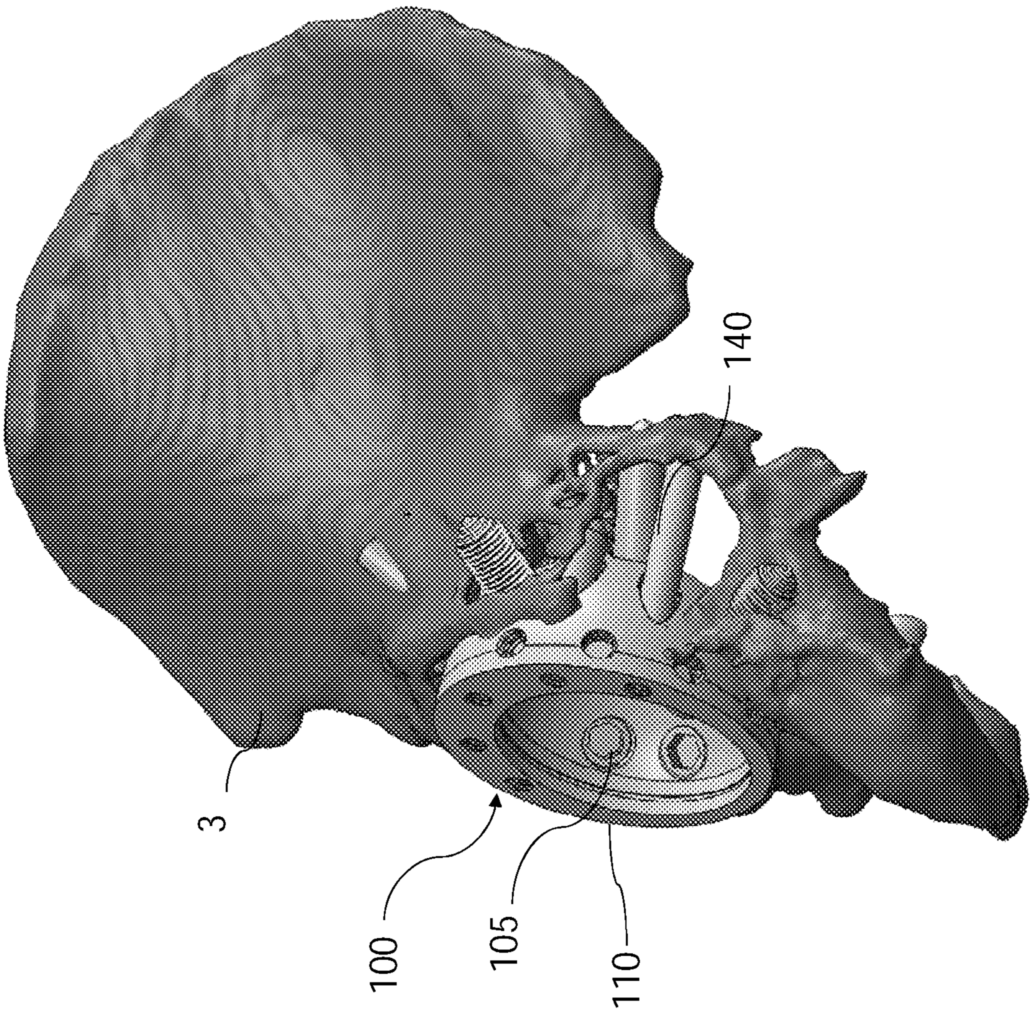
FIG. 41 illustrates a perspective view of an embodiment of the hip implant assembly surgically placed and secured to a portion of highly compromised bone tissue in the pelvic area.

The method of employing the medical implant system 200, in this case the medical implant system 200 for hip implants, will now be discussed with reference to FIGS. 39-41. As a first step, the surgeon removes the failed implant (if not already done) and assesses the bone loss at the implant site. The host bone tissue 3 is then prepared using an appropriate preparation tool such as a hemispherical reamer and/or a handheld burr to enable maximum bone contact with the medical implant assembly 100 (see FIG. 41) if and where possible.

After the host bone tissue 3 is prepared, the positioning or templating device 50 is optimally positioned relative to the host bone tissue 3 using the hemispherical shape of the positioning device 50 (see FIG. 40) as a guide to the appropriate size and location of the medical implant assembly 100. The positioning device 50 is held using tacking fasteners or pins 370 inserted into one or more of the bores 53*b*, 68 of the positioning device 50 to tack the positioning device 50 in place within the surgical site as shown in FIG. 40. In an alternative embodiment, the tacking fasteners 370 are semi-rigid wires. The larger channels 53*a* and the inner openings 66 of the positioning device 50 act as a template to predrill holes or preform seats in the host bone tissue 3 for the supports 140, 240, 340, 440, 540, 640, 740, 840, 940 and/or fasteners 180. The channels or bores 53*a* and the inner openings 66 are configured to engage instrument adapters or guides 70 and 80 respectively, such as drill or mill bushings, to enable preparation of the host bone tissue 3. For example, a drill bushing or guide 70 may engage the channel 53*a* to guide the formation of one or more holes of various shapes in the host bone tissue 3 along a specific plane and to a specific depth. Preparation of the host bone tissue 3 through the channels 53*a* must be done using the templating device 50 so that the medical implant assembly 100 can be at least partially preassembled and positioned in the surgical site. The preparation of the host bone tissue 3 through the inner openings 66 can be done using the positioning device 50 or can be done using the medical implant assembly 100 (see FIG. 41) itself. The use of the positioning device 50 also acts to assess the need and suitability for other supplementary fixation devices as will be described below. These devices include a bone plate (not configured for bone ingrowth necessarily) and the large superior and inferior flanges configured to support the implant assembly 100 (see FIG. 41) on the ilium bone (superior) and the ischium/pubis bones (inferiorly). These flanges are configured so that the face contacting bone supports bone ingrowth and/or ongrowth. The holes in the flanges/plate can be prepared at this time but this preparation is not necessary and can be done using the medical implant assembly 100 once the assembly is placed.

Once the host bone tissue 3 has been suitably prepared, the tacking fasteners 370 (FIG. 40) are removed and the positioning device 50 is removed. The positioning device 50 is used as a guide to at least partially preassembly the medical implant assembly 100. For example, the size of the positioning device 50 is used to determine the proper size of the body 110 to be used and the predrilled holes made in the host bone tissue 3 are used as a guide to preassemble or have available for pre-assembly one or more supports 140, 240, 340 440, 640 onto the body 110. All components of the medical implant assembly 100 are to be received in separate sterile packages. Accordingly, the surgeon can select from differently sized bodies 110, supports 140, 240, 340, 440, 640 and fasteners 180. Once the medical implant assembly 100 is at least partially assembled, the assembly is then placed in the surgical site as shown in FIG. 41. Referring back to FIGS. 33A-B, the body 110 may include a positioning bore 161 that is centrally positioned within the cavity 162 of the body 110 and used to aid in the positioning of the body 110 in the surgical site. For example, the surgeon can removably couple a positioning tool (not shown) to the positioning bore 161 to enable positioning of the body 110 and the application of force to the body 110. As shown in FIG. 41, the preassembled medical implant assembly 100 may include one or more supports 140 secured to the body 110 via the bores 113 such that the preassembled supports 140 extend along parallel axes. These preassembled supports 140 correspond to predrilled or preformed openings in the host bone tissue 3 and are inserted therein. Additional holes are predrilled through one or more inner openings 126 defined in the body 110 and into the host bone tissue 3. Additional supports 440, 540, 640 and/or fasteners 180 and adapters 280 are installed through the inner openings 126 and into the additional holes to further support and secure the body 110 of the medical implant assembly. Since these fasteners/supports extend along axes that are not parallel to the preassembled supports, they must be installed in situ. Once the medical implant assembly 100 is secured or fixed, a bearing liner or insert 4 (see FIG. 1) can be placed in the cavity of the body 110.

Figure 42:
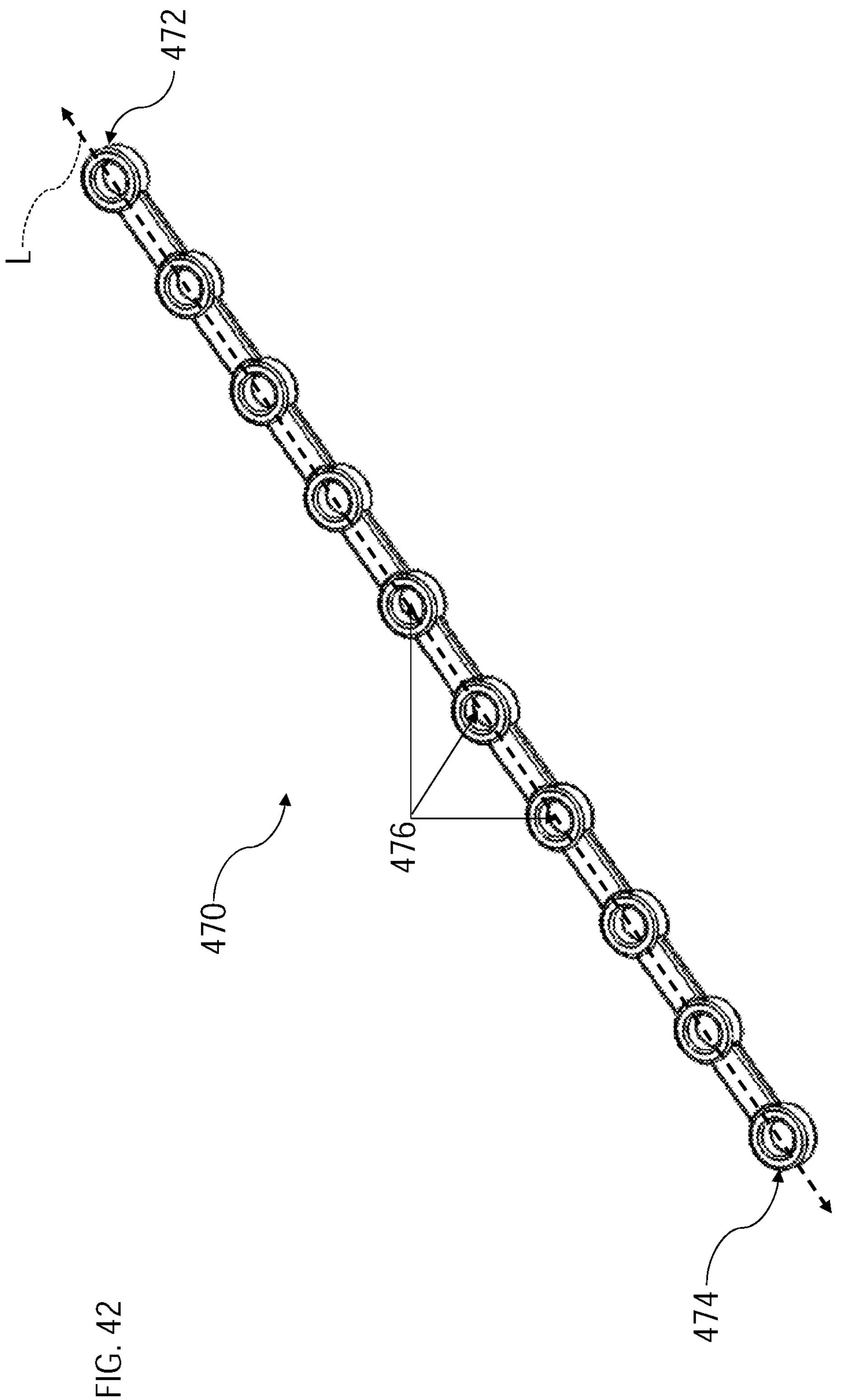
FIG. 42 illustrates a perspective view of an embodiment of a securing member, such as a securing plate, used to further secure the body of the medical implant assembly to a portion of host bone tissue.
Figure 43B:
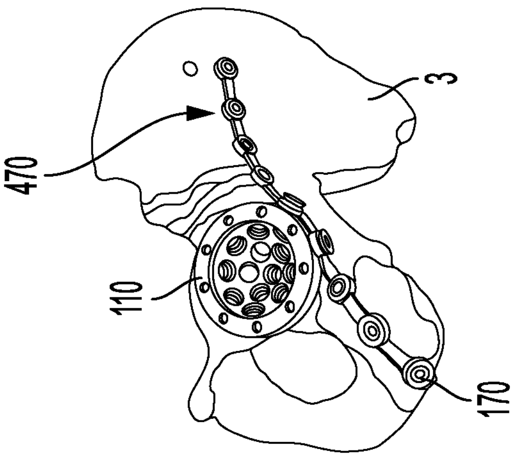
FIG. 43B illustrates a top perspective view of the embodiment of FIG. 43B.
Figure 43A:
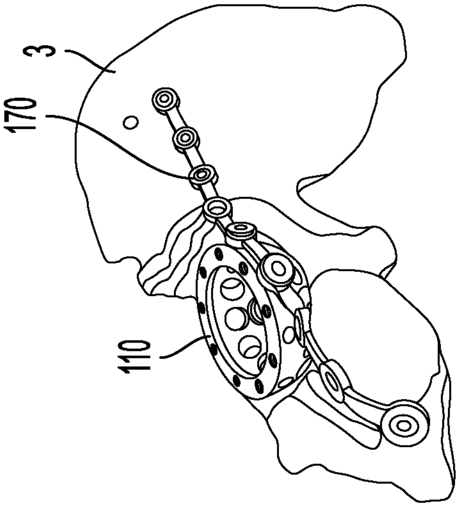
FIG. 43A illustrates a side perspective view of the embodiment of the securing member of FIG. 42 being used to secure a portion of an embodiment of the body of the hip implant assembly to a portion of pelvic bone tissue.

Turning to FIGS. 42-47B, additional securing members 470, 570, 670 may be coupled to the body 110 of the medical implant assembly 100 in order to provide additional support and stability for the body 110. These securing members 470, 570, 670 may be used in addition to or in lieu of the supports 140, 240, 440, 540, 640 previously described, depending on the surgeon's preference and the on the condition of the host bone tissue 3 (see FIGS. 1, 2, 39-41, 43A and 43B). With reference to FIGS. 42-43B, an embodiment of a securing member 470, such as a securing strip, is shown extending along a longitudinal axis L between a first end 472 and a second end 474 and defining a plurality of through holes 476 in equal spaced relation. According to this embodiment, ten holes 476 are provided although the precise number of holes 476 can be suitably varied. With reference to FIGS. 43A-B, the securing member 470 is being used to secure the body 110 of the medical implant assembly 100 to the host bone tissue 3. Fasteners 170, such as screws, are driven through one or more of the corresponding holes 476 in the securing member 470 and into the body 110 or the host bone tissue 3. In an embodiment, other fasteners 180, such as compression bone screws, may be used in conjunction with the securing member 470. As shown, it can be seen that the securing member 470 is somewhat flexible and able to bend and flex relative to the body 110 in order to be brought into contact with host bone tissue 3 that is not opposing the body 110. It should be noted that not every hole 476 requires placement of a fastener 170 as the placement and number of fasteners 170 used can be at the discretion of the surgeon.

Figure 44A:
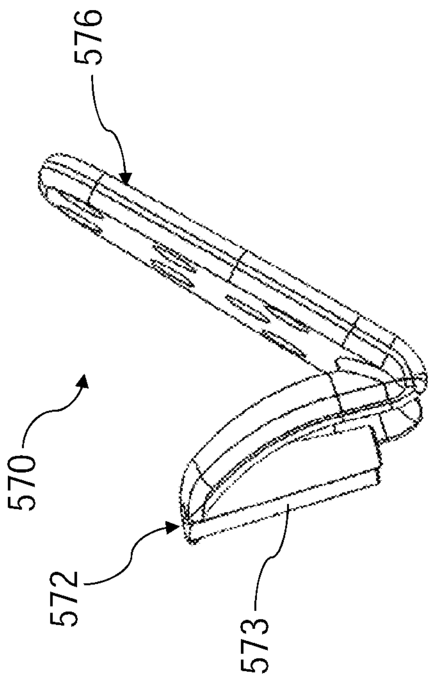
FIG. 44A illustrates a side perspective view of an embodiment of another securing member, such as a bone plate or augment or flange, used to further secure the body of the medical implant assembly to a portion of host bone tissue.
Figure 44B:
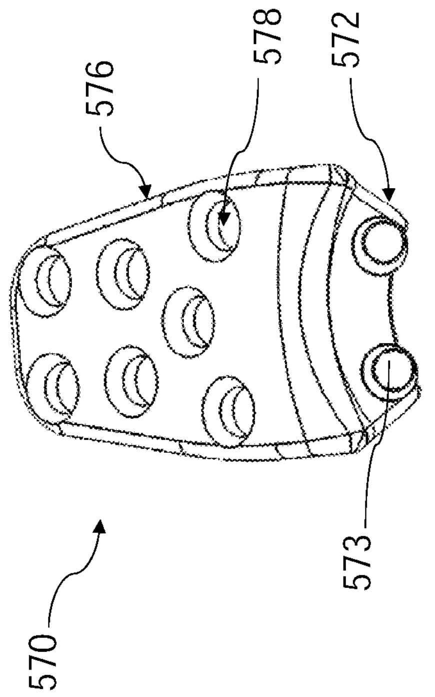
FIG. 44B illustrates a bottom perspective view of the embodiment of the securing member of FIG. 44A.
Figure 44C:
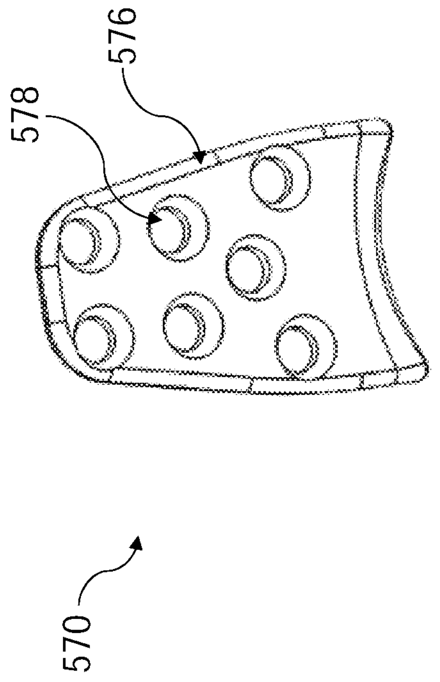
FIG. 44C illustrates a top perspective view of the embodiment of the securing member of FIGS. 44A and 44B.
Figure 44D:
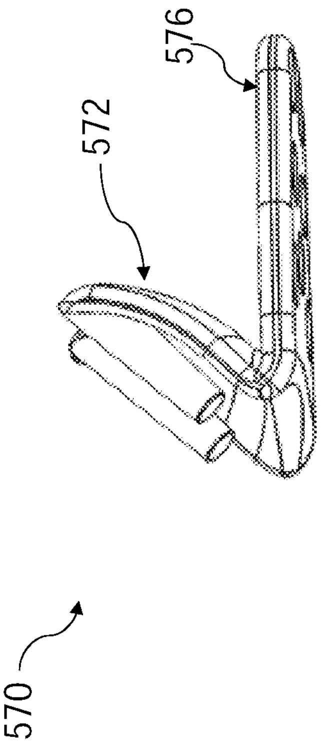
FIG. 44D illustrates another side perspective view of the embodiment of the securing member of FIGS. 44A-C.
Figure 45:
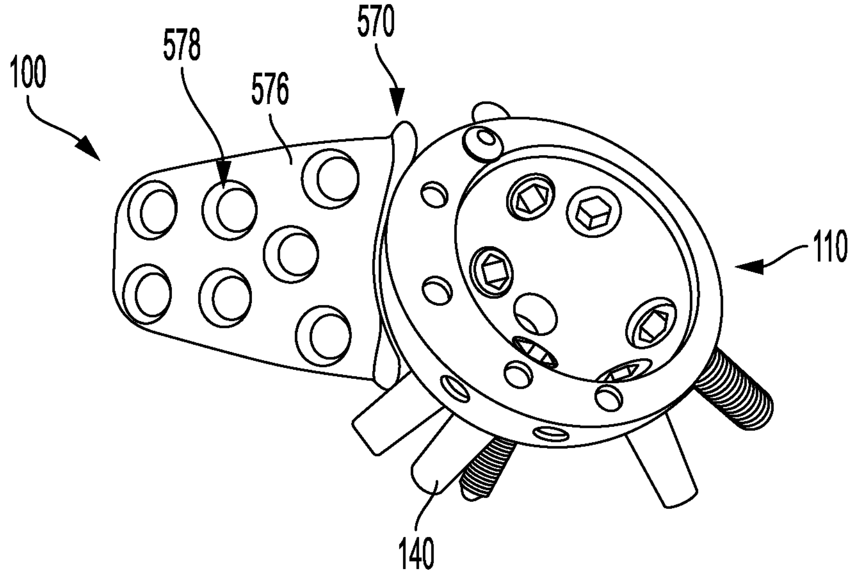
FIG. 45 illustrates a top perspective view of the embodiment of the securing member of FIGS. 44A-D coupled to an embodiment of the body.
Figure 46A:
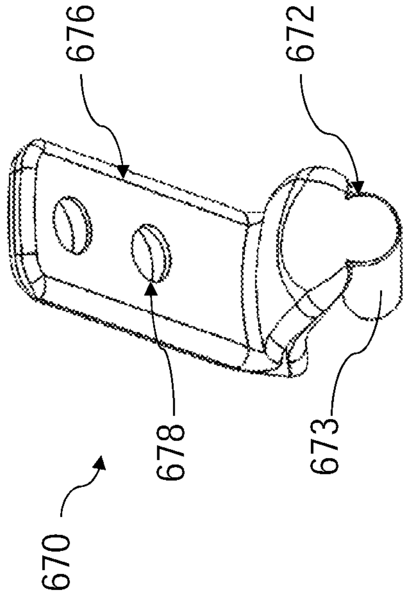
FIG. 46A illustrates a bottom perspective view of another embodiment of a securing member, such as a bone plate, augment or flange.
Figure 46B:
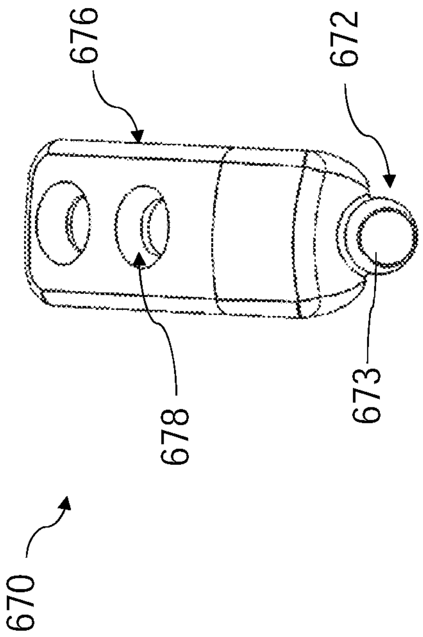
FIG. 46B illustrates a top view of the embodiment of the securing member from FIG. 46A.
Figure 46C:
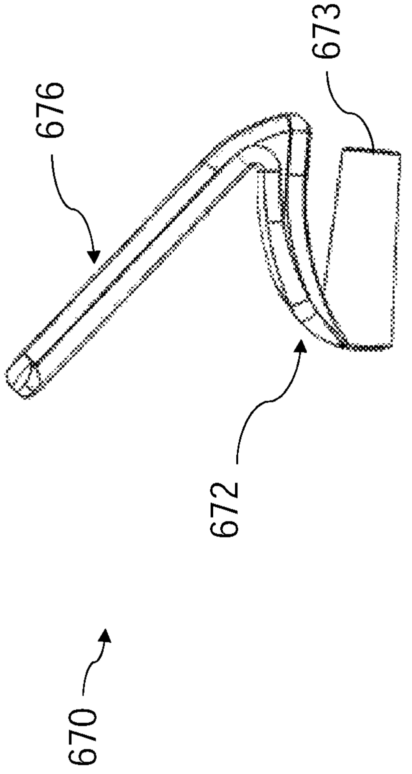
FIG. 46C illustrates a side view of the embodiment of the securing member from FIGS. 46A and 46B.
Figure 46D:
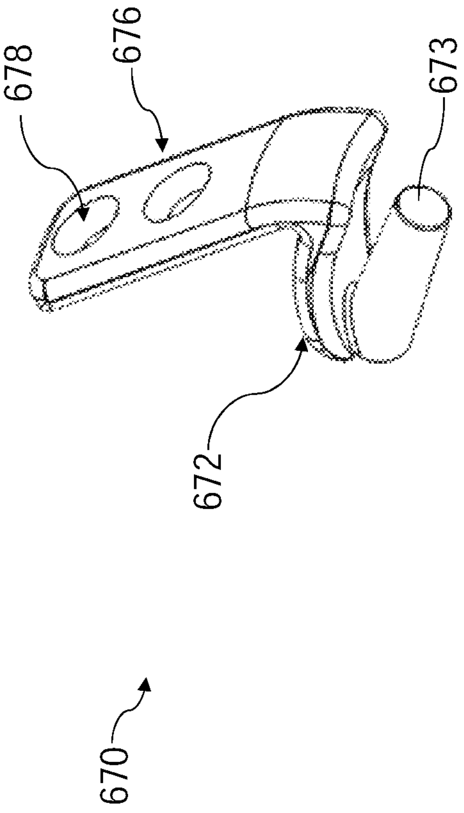
FIG. 46D illustrates a top perspective view of the embodiment of the securing member from FIGS. 46A-C.

Turning to FIGS. 44A-45, another embodiment of a securing member 570, such as a bone plate, flange or augment, is shown. The securing member 570 according to this embodiment is defined by a one piece body that includes a body coupling portion 572 and a tissue coupling portion 576. The body coupling portion 572 is inwardly reflexed in relation to the tissue coupling section, as shown most clearly in FIG. 44D and may include one or more body coupling members 573 that project along the reflexed angle of the section. The tissue coupling portion 576 is defined by a planar section that includes a plurality of spaced openings 578. As shown, the body coupling members 573 are structured to couple to the body 110 through one or more openings in the body 110. In other embodiments, the body coupling portion 572 of the securing member 570 is coupled to the body 110 using one or more fasteners 180.

FIG. 45 illustrates the securing member 570 as coupled to the body 110 of the medical implant assembly 100. As can be seen, the securing member 570 is coupled to the body 110 so that the tissue coupling portion 576 extends away from the body 110 such that one or more fasteners 180 can be inserted through one or more of the plurality of spaced openings 578 to couple or otherwise fix the body 110 to host bone tissue 3 (see FIGS. 1, 2, 40-42, 44A and 44B) that is not in contact with the body 110.

Figure 47B:
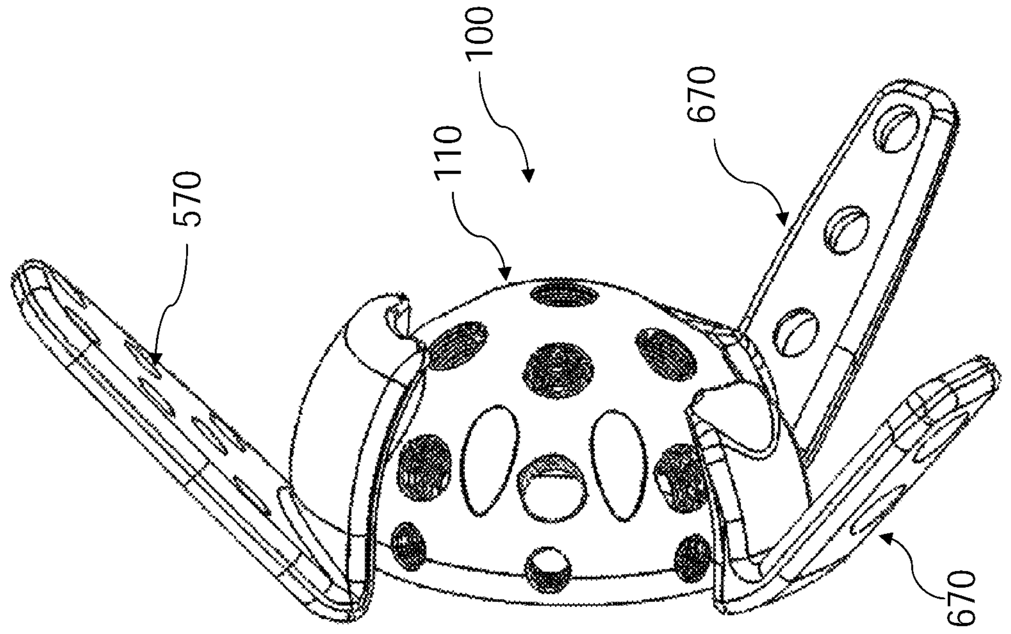
FIG. 47B illustrates a side perspective view of the embodiment of FIG. 47A.
Figure 47A:
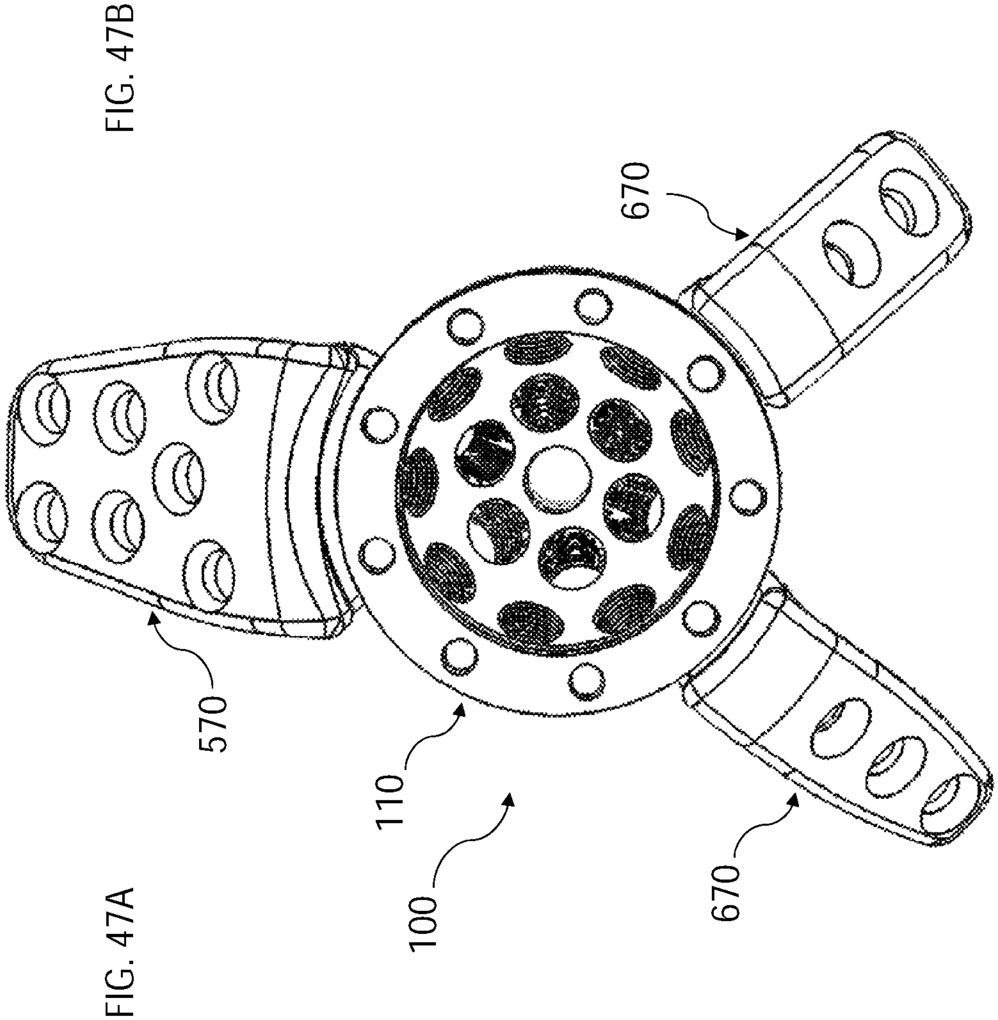
FIG. 47A illustrates a top view of an embodiment of a body of the medical implant assembly with embodiments of the securing members from FIGS. 44A-D and FIGS. 46A-D both attached.

FIGS. 46A-D illustrate the securing member 670, such as a bone plate, flange or augment, which includes two main sections, namely a body coupling portion 672 and a tissue coupling portion 676. The body coupling portion 672 is reflexed from the tissue couple portion 676 and includes at least one body coupling member 673 and the bone coupling portion 676, which is a planar section, defines a plurality of spaced openings 678 that traverse the tissue coupling portion 676. As shown in FIGS. 47A-B, one or more of the securing members 570, 670 can be coupled to the body 110 of the medical implant assembly 100 to aid in fixing the body relative to the host bone tissue 3 (see FIGS. 1, 2, 39-41, 43A and 43B). The securing members 570, 670 are generally preassembled on the body 110 prior to positioning the body 110 in the surgical site. However, securing member 470 may be preassembled to the body 110 prior to positioning in the surgical site or may be coupled to the body 110 after it is positioned in the surgical site.

The foregoing securing members 470, 570, 670 are mere examples of securing members. To that end, other configurations of securing members 470, 570, 670 are envisioned that are configured to couple the body 110 to one or more portions of host bone tissue 3 (see FIGS. 1, 2, 39-41, 43A and 43B) that are not in contact with the body 110. For example and according to at least one variant, one or more of the securing members 470, 570, 670 are flexible such that they can engage and be secured to bodies 110 of varying shapes and sizes as well as host bone tissue 3 (see FIGS. 1, 2, 39-41, 43A and 43B) of various shapes and sizes. In some embodiments, the securing members 470, 570, 670 may be structured to promote and/or allow bone ingrowth or ongrowth on the entirety of the host tissue or only a portion thereof.

In some embodiments, the medical implant assembly 100 is able to be positioned such that a portion of the body 110 contacts the host bone tissue 3 (see FIGS. 1, 2, 39-41, 43A and 43B). In these situations, fasteners 180 (see FIG. 30), such as compression bone screws, may be used to further connect the body 110 directly to host bone tissue 3 (see FIGS. 1, 2, 39-41, 43A and 43B) through the inner openings 126 (see FIG. 32) of the body 110. The additional fasteners/supports 180, 440, 540, 640 (see FIG. 31) must be installed after the medical implant assembly 100 is positioned in the surgical site. The openings in the cavity are threaded and allow a drilling or reaming device to create a prepared hole for the subsequent support 440, 540, 640 if this had not already been prepared using the templating or positioning device 50. In their installed state, the supports 440, 540, 640 (see FIG. 32) are countersunk or flush with the interior concave surface 124 (see FIG. 32) such that they do not interfere with positioning and securing of the insert 4 (see FIG. 1). Such fasteners 180 can be compression screws, locking screws, locking pegs with surfaces that approximate to bone that promote and/or allow bone ingrowth and/or ongrowth to enhance long term stability. The position of the fasteners 180 (see FIG. 30) and the additional supports 440, 540, 640 (see FIG. 32) inhibits fretting of the insert 4 (see FIG. 1), which will help to prolong the overall life of the prosthetic hip 1 (see FIG. 1). In an embodiment, the use of fasteners 170 (see FIG. 30) acts as an additional securing method for the one or more supports 140, 240, 340, 740, 840, 940 even though some of the supports are not depicted with reciprocal threads for simplicity. Additionally a way of providing a system to release these supports using fastener 270 from the body 110 is provided.

One or more components of the medical implant system 200, including the positioning device 50, the medical implant assembly 100 and the securing members or fasteners 170 may be comprised of titanium, titanium alloy, steel, cobalt chromium or another metal or alloy.

Additional embodiments include any one of the embodiments described above, where one or more of its components, functionalities or structures is interchanged with, replaced by or augmented by one or more of the components, functionalities or structures of a different embodiment described above.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure, nor the claims which follow.

The invention claimed is:

1. A hip implant assembly comprising:
- a body comprising,
  - an outer surface,
  - a cavity defined by an inner surface, the cavity having a plurality of inner openings extending between the inner surface and the outer surface,
  - a rim defining an opening of the cavity, and
  - a plurality of bores extending between the rim and the outer surface; and
- one or more supports removably coupled to the body that each comprise,
  - a first end comprising a tapered surface that is configured to enable a friction fit within one of the plurality of bores, and
  - an opposing second end positioned away from the body and configured to be secured to a host bone tissue,
- wherein the first end of the one or more supports is inserted into one of the plurality of bores from the outer surface of the body, and
- wherein the one or more supports are configured to at least partially hold the body away from the host bone tissue and wherein the one or more supports and the body are configured to promote or allow at least one of: (i) bone ingrowth; and (ii) bone ongrowth.

2. The hip implant assembly of claim 1, wherein at least one of the plurality of bores comprises a continuously changing diameter between the rim and the outer surface.

3. The hip implant assembly of claim 1, wherein at least a portion of the one or more supports comprise a circular cross-section.

4. The hip implant assembly of claim 1, wherein at least one of the first end and the opposing second end of the one or more supports comprises a tapered surface.

5. The hip implant assembly of claim 1, wherein the first end of the one or more supports is configured to at least partially receive a fastener.

6. The hip implant assembly of claim 1, wherein the cavity is configured to receive an insert of a prosthetic hip.

7. The hip implant assembly of claim 1, wherein at least one of the first end and the second end of the one or more supports comprises a threaded surface.

8. The hip implant assembly of claim 1, further comprising at least one securing member comprising:
- a first end configured to be removably coupled to the body; and
- a second end defining one or more openings dimensioned to accept a fastener to couple the at least one securing member to the host bone tissue, wherein the host bone tissue is positioned away from the body.

9. The hip implant assembly of claim 1, wherein the one or more supports comprises a shoulder.

10. The hip implant assembly of claim 1, wherein at least one of the inner openings includes a tapered surface configured to enable a friction-fit with the one or more supports.

11. The hip implant assembly of claim 1, wherein the first end of the one or more supports comprises a non-polygonal cross-section.

12. The hip implant assembly of claim 1, wherein at least a portion of the one or more supports comprises a biochemical coating configured to enhance natural bone formation.

13. A medical implant assembly comprising:
- a body comprising,
  - an outer surface,
  - a cavity defined by an inner surface, a rim surrounding a cavity opening and defining a plurality of bores extending from the rim to the outer surface, one or more openings extending between the inner surface and the outer surface; and at least one support removably coupled to the body, the at least one support comprising, a first end comprising a tapered surface that is configured to frictionally fit within one of the plurality of bores, and an opposing second end positioned away from the body and configured to be secured to a host bone tissue, wherein the first end of the one or more supports is inserted into one of the plurality of bores from the outer surface of the body, wherein compression forces act to secure the friction fit between the first end of the at least one support and the one of the plurality of bores, and wherein at least one of: (i) the at least one support; and (ii) the body, are configured for at least one of: (i) bone ingrowth; and (ii) bone ongrowth.

14. The medical implant assembly of claim 13, wherein the cavity is eccentrically positioned in relation to the rim.

15. The medical implant assembly of claim 13, wherein at least one of the plurality of bores comprises a continuously changing diameter between the rim and the outer surface.

16. The medical implant assembly of claim 13, wherein the at least one support is configured to at least partially hold the body away from the host bone tissue.

17. The medical implant assembly of claim 13, wherein at least a portion of the at least one support comprises a circular cross-section.

18. The medical implant assembly of claim 13, wherein at least one of the first end and the opposing second end of the at least one support comprises a tapered surface.

19. The medical implant assembly of claim 13, wherein the first end of the at least one support is configured to receive a fastener to couple the support to the body.

20. The medical implant assembly of claim 13, wherein the cavity is configured to receive an insert of a prosthetic hip.

21. The medical implant assembly of claim 13, wherein at least one of the first end and the opposing second end of the at least one support comprises a threaded surface.

22. The medical implant assembly of claim 13, further comprising at least one securing member comprising:

a first end configured to be removably coupled to the body; and a second end configured to contact the host bone tissue and defining one or more openings dimensioned to accept a fastener to couple the at least one securing member to the host bone tissue, wherein the host bone tissue is positioned away from the body, and wherein the first end.

23. The medical implant assembly of claim 22, wherein the first end of the at least one securing member is inwardly reflexed in relation to the opposing second end.

24. The medical implant assembly of claim 13, wherein the at least one support comprises a shoulder configured to prevent over insertion of the at least one support into the host bone tissue.

25. The medical implant assembly of claim 13, wherein the at least one support comprises a first tapered portion and a second tapered portion, wherein the first tapered portion comprises and increasing diameter from the first end of the at least one support to a circumferential apex and the second tapered portion comprises a decreasing diameter from the circumferential apex to the opposing second end of the at least one support.

26. The medical implant assembly of claim 13, wherein the first end of the at least one support comprises a first diameter and the opposing second end of the at least one support comprises a second diameter that is different than the first diameter.

27. The medical implant assembly of claim 15, wherein the first end of the at least one support comprises a non-polygonal cross-section.

28. The medical implant assembly of claim 27, wherein the non-polygonal cross-section is a discorectangle.

29. The medical implant assembly of claim 13, wherein at least some of the plurality of bores extend along parallel axes.

30. The medical implant assembly of claim 13, wherein at least some of the one or more openings extending between the inner surface and the outer surface extend along intersecting axes.

31. The medical implant assembly of claim 13, wherein at least a portion of the at least one support comprises a biochemical coating configured to enhance natural bone formation.

32. A method of manufacturing a hip implant assembly, comprising:

structuring a body to comprise, an outer surface, a rim defining an opening to a formed cavity;

a plurality of bores extending from the rim to the outer surface, an inner surface defining the formed cavity, and one or more inner openings extending between the inner surface and the outer surface; and structuring one or more supports to comprise, a first end including a tapered surface configured to be inserted into one of the plurality of bores from the outer surface of the body and configured to frictionally fit within the one of the plurality of bores, a second end positioned away from the body and configured to be secured to a host bone tissue, and a portion configured for at least one of: (i) bone ingrowth; and (ii) bone ongrowth.

33. The method of claim 32, further comprising eccentrically positioning the cavity in relation to the rim.

34. The method of claim 32, further comprising structuring at least a portion of the one or more supports to comprise a circular cross-section.

35. The method of claim 32, further comprising structuring the first end of the one or more support to receive a fastener.

36. The method of claim 32, further comprising structuring the cavity to receive an insert of a prosthetic hip.

37. The method of claim 32, further comprising structuring one of the first end and the second end of the one or more supports to comprise a threaded surface.

38. The method of claim 32, further comprising structuring at least one securing member to comprise:

a first end configured to be removably coupled to the body; and a second end defining one or more openings dimensioned to accept a fastener to couple the at least one securing member to the host bone tissue, wherein the host bone tissue is positioned away from the body.

39. The method of claim 32, further comprising structuring the body with a plurality of channels extending between the rim and the outer surface.

40. The method of claim 32, further comprising structuring the one or more supports to include a biochemical coating configured to enhance natural bone formation.

41. A medical implant system comprising:

a templating device comprising a body configured to be positioned in a surgical site and configured to guide a medical instrument for preparing the surgical site; and a medical implant assembly, comprising, a body comprising, an outer surface, a cavity defined by an inner surface, a rim surrounding a cavity opening and defining a plurality of bores extending from the rim to the outer surface, one or more openings extending between the inner surface and the outer surface, and at least one support removably coupled to the body, the at least one support comprising, a first end comprising a tapered surface and configured to frictionally fit within one of the plurality of bores, and an opposing second end positioned away from the body and configured to be secured to a host bone tissue within the surgical site, wherein the first end of the one or more supports is inserted into one of the plurality of bores from the outer surface of the body, wherein compression forces act to secure the friction fit between the first end of the at least one support and the one of the plurality of bores, and wherein at least one of: (i) the at least one support; and (ii) the body, are configured for at least one of: (i) bone ingrowth; and (ii) bone ongrowth.

* * * * *